US009961900B2

(12) United States Patent
Anderson et al.

(10) Patent No.: US 9,961,900 B2
(45) Date of Patent: *May 8, 2018

(54) HERBICIDE FORMULATIONS

(71) Applicant: VIVE CROP PROTECTION INC., Toronto (CA)

(72) Inventors: Darren J. Anderson, Toronto (CA); Anjan Kumar Das, Oakville (CA); Jose Amado Dinglasan, Toronto (CA); Fugang Li, Richmond Hill (CA); Danielle Norton, Toronto (CA)

(73) Assignee: Vive Crop Protection Inc., Toronto, Ontario (CA)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/406,855

(22) PCT Filed: Jun. 11, 2013

(86) PCT No.: PCT/IB2013/054760
§ 371 (c)(1),
(2) Date: Dec. 10, 2014

(87) PCT Pub. No.: WO2013/186695
PCT Pub. Date: Dec. 19, 2013

(65) Prior Publication Data
US 2015/0141249 A1 May 21, 2015

Related U.S. Application Data

(60) Provisional application No. 61/657,946, filed on Jun. 11, 2012, provisional application No. 61/672,459, filed on Jul. 17, 2012, provisional application No. 61/763,160, filed on Feb. 11, 2013.

(51) Int. Cl.
| *A01N 43/90* | (2006.01) |
| *A01N 43/76* | (2006.01) |
| *A01N 43/653* | (2006.01) |
| *A01N 47/36* | (2006.01) |
| *A01N 25/02* | (2006.01) |
| *A01N 25/14* | (2006.01) |
| *A01N 25/22* | (2006.01) |
| *A01N 25/30* | (2006.01) |

(52) U.S. Cl.
CPC ............. *A01N 43/90* (2013.01); *A01N 25/02* (2013.01); *A01N 25/14* (2013.01); *A01N 25/22* (2013.01); *A01N 25/30* (2013.01); *A01N 43/653* (2013.01); *A01N 43/76* (2013.01); *A01N 47/36* (2013.01)

(58) Field of Classification Search
None
See application file for complete search history.

(56) References Cited

U.S. PATENT DOCUMENTS

| 5,292,828 | A | 3/1994 | Jenkins et al. |
| 6,383,500 | B1 | 5/2002 | Wooley et al. |
| 6,383,984 | B1 | 5/2002 | Aven |
| 6,436,421 | B1 | 8/2002 | Schindler et al. |
| 6,604,698 | B2 | 8/2003 | Verhoff et al. |
| 6,616,946 | B1 | 9/2003 | Meier et al. |
| 6,683,129 | B1 | 1/2004 | Eknoian |
| 6,897,253 | B2 | 5/2005 | Schmucker-Castner et al. |
| 6,916,481 | B1 | 7/2005 | Prud'Homme et al. |
| 7,070,795 | B1 | 7/2006 | Botts et al. |
| 7,189,279 | B2 | 3/2007 | Guillet |
| 7,939,601 | B1 | 5/2011 | Bergeron et al. |
| 7,994,227 | B2 | 8/2011 | Koltzenburg et al. |
| 8,029,827 | B2 | 10/2011 | Martin |
| 8,034,888 | B2 | 10/2011 | Nguyen-Kim et al. |
| 8,309,489 | B2 | 11/2012 | Roldan Cuenya et al. |
| 8,372,418 | B2 | 2/2013 | Dujardin et al. |
| 8,974,806 | B2 | 3/2015 | Amrhein et al. |
| 2007/0066481 | A1* | 3/2007 | Ziemer ............... A01N 25/32 504/103 |
| 2007/0212321 | A1 | 9/2007 | Braig et al. |
| 2008/0171658 | A1 | 7/2008 | Dyllick-Brenzinger et al. |
| 2008/0213326 | A1* | 9/2008 | Amrhein ............... A01N 25/04 424/405 |
| 2009/0053272 | A1 | 2/2009 | Wagenblast |
| 2010/0015236 | A1 | 1/2010 | Magdassi et al. |
| 2010/0179198 | A1 | 7/2010 | Mertoglu et al. |
| 2010/0210465 | A1 | 8/2010 | Li et al. |

(Continued)

FOREIGN PATENT DOCUMENTS

| CA | 2203686 A1 | 11/1997 |
| CN | 1491541 A | 4/2004 |
| EP | 0183999 | 6/1986 |
| WO | WO-2010035118 A1 | 4/2010 |
| WO | WO-2011117719 A1 | 9/2011 |
| WO | WO-2013093578 A1 | 6/2013 |

OTHER PUBLICATIONS

International Search Report for PCT/IB2013/054760, 4 pages (dated Oct. 7, 2013).
Written Opinion for PCT/IB2013/054760, 6 pages (dated Oct. 7, 2013).
McMullen, P., Grass Herbicide Efficacy as Influenced by Adjuvant, Spray Solution pH, and Ultraviolet Light, Weed Technology, 10(1):72-77 (1996).
Ng, W. et al., Rheological properties of methacrylic acid/ethyl acrylate co-polymer: comparison between an unmodified and hydrophobically modified system, Polymer, 42:249-259 (2001).

*Primary Examiner* — Alton N Pryor
(74) *Attorney, Agent, or Firm* — Charles E. Lyon; Su Kyung Suh; Choate, Hall & Stewart LLP

(57) ABSTRACT

The present disclosure describes a formulation comprising a nanoparticle including a polymer-associated herbicide, such as fenoxaprop or pyroxsulam with an average diameter of between about 1 nm and about 500 nm; wherein the polymer is a polyelectrolyte and a dispersant or a wetting agent. The disclosure describes various formulations and formulating agents that can be included in the formulations.

19 Claims, 21 Drawing Sheets

(56) References Cited

U.S. PATENT DOCUMENTS

| | | |
|---|---|---|
| 2010/0227761 A1 | 9/2010 | Bruggemann et al. |
| 2011/0045975 A1 | 2/2011 | Ehr et al. |
| 2011/0081555 A1 | 4/2011 | Liu et al. |
| 2011/0189294 A1 | 8/2011 | Keiper et al. |
| 2012/0035054 A1 | 2/2012 | Ehr et al. |
| 2012/0184589 A1 | 7/2012 | Gewehr et al. |
| 2012/0214857 A1 | 8/2012 | Reinhard et al. |
| 2012/0264603 A1 | 10/2012 | Soane et al. |
| 2012/0329648 A1 | 12/2012 | Fowler et al. |
| 2013/0034650 A1 | 2/2013 | Li et al. |
| 2013/0274110 A1 | 10/2013 | Westbye et al. |
| 2013/0338223 A1 | 12/2013 | Reid et al. |
| 2014/0080702 A1 | 3/2014 | Schnabel et al. |
| 2014/0249031 A1 | 9/2014 | Mulqueen et al. |
| 2014/0294968 A1 | 10/2014 | Hofmann et al. |
| 2014/0364310 A1* | 12/2014 | Li .......................... A01N 37/50 504/101 |

\* cited by examiner

| Sample: | Crop 3 | Crop 3 | Crop 3 | Crop 3 |
| --- | --- | --- | --- | --- |
| Dilution: | 1% | 0.1% | 1% | 0.1% |
| Media | DI | DI | 342 ppm | 342 ppm |

HERBICIDE FORMULATIONS

CROSS REFERENCE TO RELATED APPLICATIONS

This application is U.S. National Stage Application filed under 35 U.S.C. § 371 based on International Application No. PCT/IB2013/054760 filed Jun. 11, 2013, which claims priority to U.S. Provisional application No. 61/763,160 filed Feb. 11, 2013, U.S. Provisional application No. 61/672,459 filed Jul. 17, 2012, and U.S. Provisional application No. 61/657,946 filed Jun. 11, 2012, the entire contents of each of which are hereby incorporated herein by reference.

BACKGROUND OF THE INVENTION

Aryloxyphenoxypropionate and cyclohexanedione herbicides have been widely used to control various pestilent annual and perennial grass species. These compounds, which are often applied to target weeds after their emergence, function as inhibitors of acetyl CoA carboxylase (ACCase), an integral enzyme in the biosynthesis of fatty acids. Susceptible grasses suffer compromised cell membrane function, inhibition of growth, and necrosis.

Some triazolinone herbicides, such as carfentrazone-ethyl, function as inhibitors of protoporphyrinogen oxidase. The inhibition of this enzyme leads to an accumulation of its substrate Protox in plastids. Through cellular and light mediated oxidation pathways, Protogen produces reactive species such as singlet oxygen that are capable of initiating lipid auto-oxidation. Susceptible plants suffer compromised cell membrane function and necrosis. Triazolinone inhibitors of protoporphyrinogen oxidase are often applied as post-emergent herbicides for the control of broad-leaved weeds.

Sulfonylureas are also very common herbicides used with all major agronomic crops (e.g., cereals, corn, and soybeans) as well as in pasture, forestry and vegetation management applications. Sulfonamides (also referred to as triazolopyarimidines), which have a similar mode of action and related chemical structure as sulfonylureas are also frequently used in crop protection applications (e.g., soybeans, corn and cereals). The primary mode of action of sulfonylureas and sulfonamides is by inhibiting acetohydroxyacid synthase (AHAS), also referred to as acetolactic synthase (ALS). The AHAS/ALS enzyme functions in the synthetic pathway for the production of branched chain amino acids. Specifically this enzyme catalyzes reactions to lead to the formation of valine and leucine. Applications of sulfonylureas and sulfonamides almost instantly halt growth, leading to yellowing and/or reddening of the leaves, shoot death and eventual plant death.

Other herbicides with similar modes of action include imidazolinones (e.g., imazapyr), pyrimidinylcarbonxylate, sulfonanilides and sulfonylaminocarbonyl-triazolinones, though chemical structures among these compounds may vary dramatically.

The physical and chemical properties of the aforementioned classes of herbicides present challenges to their effective use. For example, some of their members are highly non-polar, substantially water insoluble, susceptible to hydrolysis under alkaline or acidic conditions, and unstable to light. Formulations are developed to improve efficacy and to, in part, compensate for the limitations of some of these herbicides.

SUMMARY OF THE INVENTION

The present invention provides formulations of herbicidal compounds comprising nanoparticles of polymer-associated herbicides. In some embodiments, the herbicide is selected from the group consisting of aryloxyphenoxypropionate herbicides, cyclohexanedione herbicides, triazolinone inhibitors of protoporphyrinogen oxidase, sulfonamides and sulfonylureas. In some embodiments the formulation includes various formulating agents (e.g., dispersants, wetting agents, inert fillers, solvents, surfactants, anti-freezing agents, anti-settling agents or thickeners, disintegrants, safeners, and preservatives, among others. In some embodiments, the present invention includes methods of using these formulations.

DEFINITIONS

Figure 1:
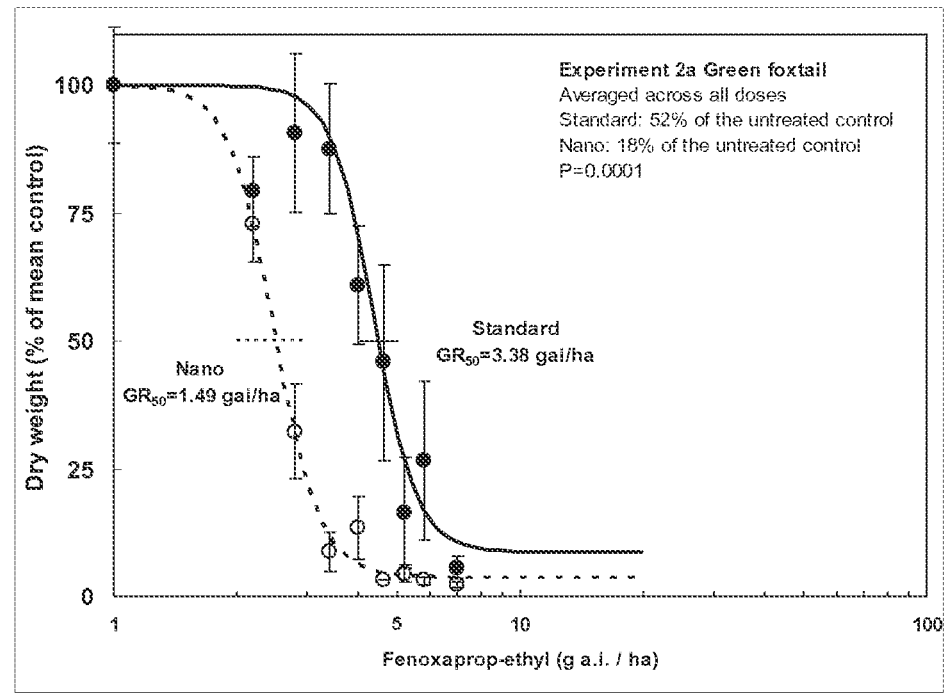
FIGS. 1 (upper) & 2 (lower): Dose response and $GR_{50}$ (50% growth reduction) of green foxtail with standard and nano-formulations of fenoxaprop-P-ethyl. Averaged across all herbicide doses the standard and nano-formulations reduced dry wt. of green foxtail to 52 and 18% of the untreated control, respectively in FIG. 1, and 59 and 37%, respectively in FIG. 2.

As used herein, the term "inoculation" refers to a method used to administer or apply a formulation of the present invention to a target area of a plant or pest. The inoculation method can be, but is not limited to, aerosol spray, pressure spray, direct watering, and dipping. Target areas of a plant could include, but are not limited to, the leaves, roots, stems, buds, flowers, fruit, and seed. Target areas of a pest (e.g., insect) could include, but are not limited to, the head, eyes, maxilla, mandible, antennae, thorax, leg, wings, and abdomen. Inoculation can include a method wherein a plant is treated in one area (e.g., the root zone or foliage) and another area of the plant becomes protected (e.g., foliage when applied in the root zone or new growth when applied to foliage).

As used herein, the term "wettable granule", also referred to herein as "WG", and "dispersible granule," and "water dispersible granules" refers to a solid granular formulation that is prepared by a granulation process and that contains nanoparticles of polymer-associated active ingredient and optionally herbicide safener, or aggregates of the same, a wetting agent and/or a dispersant, optionally an inert filler, and optionally a herbicide safener. Wettable granules can be stored as a formulation, and can be provided to the market and/or end user without further processing. In some embodiments, they can be placed in a water-soluble bag for ease of use by the end user. In practical application, wettable granules are prepared for application by the end user. The wettable granules are mixed with water in the end user's spray tank to the proper dilution for the particular application. Dilution can vary by crop, pest, time of year, geography, local regulations, and intensity of infestation among other factors. Once properly diluted, the solution can be applied by spraying.

As used herein, the term "wettable powder" also referred to herein as "WP", "water dispersible powder" and "dispersible powder", refers to a solid powdered formulation that contains nanoparticles of polymer-associated active ingredient and optionally herbicide safener, or aggregates of the same, and optionally a dispersant, optionally a wetting agent, optionally an inert filler, and optionally an herbicide safener. Wettable powders can be stored as a formulation, and can be provided to the market and/or end user without further processing. In some embodiments, they can be placed in a water-soluble bag for ease of use by the end user. In practical application, a wettable powder is prepared for application by the end user. The wettable powder is mixed with water in the end user's spray tank to the proper dilution for the particular application. Dilution can vary by crop, pest, time of year, geography, local regulations, and intensity of infestation among other factors. Once properly diluted, the solution can be applied by spraying.

As used herein, the term "high solids liquid suspension" also referred to herein as "HSLS" refers to a liquid formulation that contains nanoparticles of polymer-associated active ingredient and optionally herbicide safener, or aggregates of the same, a wetting agent and/or a dispersant, an anti-freezing agent, optionally an anti-settling agent or thickener, optionally a preservative, optionally a herbicide safener, and water. High solids liquid suspensions can be stored as a formulation, and can be provided to the market and/or end user without further processing. In practical application, high solids liquid suspensions are prepared for application by the end user. The high solids liquid suspensions are mixed with water in the end user's spray tank to the proper dilution for the particular application. Dilution can vary by crop, pest, time of year, geography, local regulations, and intensity of infestation among other factors. Once properly diluted, the solution can be applied by spraying.

As used herein, the term "weed", also referred to herein as "pestilent plant" refers to any unwanted vegetation. As used herein, the abbreviations "AI" and "ai" refer to "active ingredient".

As used herein, "$DT_{50}$" refers to the amount of time required for 50 percent of the active ingredient to degrade.

DESCRIPTION OF VARIOUS EMBODIMENTS OF THE INVENTION

The physical and chemical properties aryloxyphenoxypropionate herbicides (AOPPs, FOPs), cyclohexanedione herbicides (CHDs, DIMs) and triazolinone inhibitors of protoporphyrinogen oxidase (PPO) present challenges to their effective use. For example, many of these herbicides are highly non-polar, substantially water insoluble, and susceptible to hydrolysis under alkaline or acidic conditions.

Different formulation techniques have been developed in an attempt to address the difficulties associated with using these compounds as herbicides. In addition to sufficiently remedying these issues, an ideal formulation would have adequate loading of the active ingredient, be non-odorous, non-caking, non-foaming, stable under extreme conditions for extended periods of time, disperse rapidly upon addition to a spray tank, be compatible with a range of secondary additives and other agricultural products (fertilizer, fungicide, pesticides, herbicide safeners, other herbicides, and other formulations) added to a spray tank, pourable or flowable, and non-dusty (for solid formulations), and have sufficient/superior rainfast properties after application.

Solubility

Aryloxyphenoxypropionate (AOPP) herbicides, also known as "FOPS," have been widely used for the control of various pestilent annual and perennial grass species. AOPPs are often applied to target weeds soon after emergence, and are thus considered post-emergence herbicides. AOPPs function as inhibitors of acetyl CoA carboxylase (ACCase), an integral enzyme in the biosynthesis of fatty acids. Susceptible grasses are compromised in their ability to form lipids in their roots and growing portions, and suffer reduced cell membrane function and general necrosis.

AOPPs are generally formulated and applied to weeds as esters (e.g. alkyl esters, propargyl esters), as it is known that the esters are more plant-permeable their parent acids. Upon uptake, the esters are hydrolyzed to the corresponding propionic acids and translocate to various portions of the plant. Along with other classes of ACCase inhibitors such as cyclohexanediones (DIMs), AOPPs constitute the Group 1 herbicides.

Many AOPP herbicides have low solubility in water but generally higher solubility in organic solvents such as aromatic solvents (e.g. benzene, toluene), acetone, and dichloromethane. Table 1 provides exemplary solubility properties of various AOPPs, including their octanol-water partition coefficients (P). Values were obtained from the e-pesticide manual, Ver. 5. British Crop Protection Council and the Pesticide Properties Database, University of Hertfordshire.

solvent in the presence of surfactants. When the EC is dispersed into a spray tank and agitated, the surfactants emulsify the organic solvent into water, and the active ingredient is delivered in the organic solvent phase to the pestilent plant.

A suspension concentrate (SC) is a high solids concentrate in water. The active ingredient is milled into particles that are 1-10 microns (Alan Knowles, *Agrow Reports: New Developments in Crop Protection Product Formulation*. London: Agrow Reports May 2005). These solid particles are then dispersed into water at high concentration using surfactants. After adding the SC into the spray tank, the surfactant-stabilized particles disperse into water and are applied (still as solid particles) to the pestilent plant.

Solid formulation techniques that are currently used include the preparation of water dispersible granules or wettable powders, in which the active ingredient is absorbed to a dispersible carrier that is provided dry to the end user. When mixed into a spray tank, the carrier disperses into the water, carrying the active ingredient with it. Particle sizes for these carriers can be anywhere in the range of 1-10 microns (Alan Knowles, *Agrow Reports: New Developments in Crop Protection Product Formulation*. London: Agrow Reports May 2005).

TABLE 1

Solubility properties and octanol-water partition coefficients of various AOPPs

| Aryloxyphen-oxypropionate (AOPP) | Solubility | Octanol-water partition coefficient (P) |
|---|---|---|
| quizalofop-ethyl | Water: 0.3 mg/L (20° C.) benzene 290 g/L; xylene 120 g/L; acetone 111 g/L; ethanol 9 g/L; hexane 2.6 g/L (all at 20° C.) + | log P = 4.28 (23 ± 1° C.) distilled water + |
| diclofop-methyl | Water: 0.39 mg/L (20° C.) In acetone, toluene, dichloromethane, 500,000 mg/L; in n-Hexane: 49,700 mg/L (all at 20° C.) ++ | log P = 4.8 (pH 7, 20° C.) ++ |
| diclofop | Water: 0.453 g/L at pH 5, 122.7 g/L at pH 7, 127.4 g/L at pH 9 (all at 20° C.) + | log P = 2.81 (pH 5) log P = 1.61 (pH 7) + |
| propaquizafop | Water: 0.63 g/m3 at pH 6.8 (20° C.) In acetone, dichloromethane, ethyl acetate, toluene, >500 g/L; n-hexane 11 g/L; methanol 76 g/L; n-octanol 30 (all at 25° C.) + | log P = 4.78 (25° C.) + |
| haloxyfop-p-methyl | Water: 9.1 mg/L (unbuffered), 6.9 mg/L at pH 5, 7.9 mg/L at pH 7 (all at 25° C.) In acetone, dichloromethane, ethyl acetate, toluene, >500 g/L; n-hexane 11 g/L, methanol 76 g/L; n-octanol 30 (all at 25° C.) + | log P = 4.0 (20° C.) + |
| fluazifop-butyl | Water: 1 mg/L at pH 6.5 Miscible with acetone, hexane, methanol, dichloromethane, and xylene. Propylene glycol, 24 g/L at 20° C. + | log P = 4.5 (20° C.) + |
| fenthiaprop-ethyl | Water: 0.8 mg/L In acetone, ethyl acetate, toluene, >500 g/kg; cyclohexane >40 g/kg; ethanol, n-octanol, >50 g/L + | — |
| fenoxaprop-p-ethyl | Water: 0.7 mg/L at pH 5.8 (25° C.) In acetone, ethyl acetate, toluene, >200 g/L; methanol 43 g/L (all at 20° C.) + | log P = 4.58 + |
| clodinafop-propargyl | Water: 4.0 mg/L at pH 7 (25° C.) Methanol, 180 g/L; acetone, toluene, >500 g/L; n-hexane, 7.5 g/L; n-octanol, 21 g/L (all at 25° C.) + | log P = 3.9 (25° C.) + |
| cyhalofop-butyl | Water: 0.44 mg/L (20° C.) In methanol, acetone, xylene, 250,000 mg/L; in n-heptane: 6060 mg/L (all at 20° C.) ++ | log P = 4.8 (pH 7, 20° C.) ++ |

+ The e-pesticide manual, Ver. 5. British Crop Protection Council

++ The PPDB: Pesticide Properties Database (PPDB), University of Hertfordshire, http://sitem.herts.ac.uk/aeru/footprint/en/index.htm Due to the low water solubility of many AOPPs, they need to be formulated to disperse in water before they can be applied to pestilent species. Two liquid formulation techniques currently employed involve preparing concentrates, namely suspension concentrates, and more commonly, emulsifiable concentrates of the AOPP active.

An emulsifiable concentrate (EC) is a formulation in which the active ingredient is dissolved in a suitable organic Like AOPPs, various cyclohexanedione herbicides and triazolinone inhibitors of PPO have low water solubility, necessitating their incorporation into formulations for end use applications. Table 2 highlights the solubility properties of some members of these classes.

TABLE 2

Solubility properties and octanol-water partition coefficients of cyclohexanedione herbicides and triazolinone inhibitors of PPO

| Herbicide | Solubility | Octanol-water partition coefficient (P) |
|---|---|---|
| tralkoxydim (cyclohexanedione) | In water:<br>6.7 mg/L at 22° C. (pH 5.2)<br>6.1 mg/L at 22° C. (pH 6.5)<br>9820 mg/L at 22° C. (pH 9.0)<br>Acetone 89 g/L; dichloromethane >500 g/L; ethyl acetate 110 g/L;<br>hexane 18 g/L; methanol 18 g/L;<br>Toluene 213 g/L[+] | — |
| carfentrazone-ethyl (triazolinone) | Water: 22 mg/L (20° C.)<br>Acetone 2000 g/L; toluene, 900 g/L;<br>Hexane 30 g/L; ethanol 2000 g/L<br>(all at 20° C.) [++] | $\log P = 3.36$<br>(pH 7, 20° C.) [++] |
| azafenidin (triazolinone) | Water: 16 mg/L (20° C.) [++] | $\log P = 2.7$<br>(pH 7, 20° C.) [++] |

[+] EFSA Scientific Report (2008) 139, 1-78, Conclusion on the peer review of tralkoxydim
[++] The PPDB: Pesticide Properties Database (PPDB), University of Hertfordshire, http://sitem.herts.ac.uk/aeru/footprint/en/index.htm As discussed in more detail below, there remains a need for alternative formulations that can be used to disperse AOPPs, DIMs, and triazolinones in water. In addition, there remains a need for methods to disperse these herbicides in water.

Sulfonylureas and sulfonamides are typically more soluble in water than AOPPs and DIMs described above. Generally the recommended application concentration for sulfonamides and sulfonylureas is below the solubility limit in water, reducing the need for some adjuvants in some applications. An exemplary list of sulfonylureas and sulfonamides with their respective solubilities in water and select solvents are described in Table 3 below.

TABLE 3

Solubility properties and octanol-water partition coefficients of sulfonylureas and sulfonamides (AHAS/ALS inhibitors)

| Herbicide | Solubility | Octanol-water partition coefficient (P) |
|---|---|---|
| penoxsulam | Water: 408 mg/L (at 20° C.)<br>Acetone: 20300 mg/L<br>Methanol: 1480 mg/L | $2.5 \times 10^{-1}$<br>log P: −0.602 |
| pyroxsulam | Water: 3200 mg/L<br>Methanol: 1010 mg/L | $P: 9.77 \times 10^{-2}$<br>log P: −1.01 |
| metosulam | Water: 700 mg/L<br>Acetone: 7800 mg/L<br>Methanol: 1900 mg/L | P: 1.58<br>log P: 0.2 |
| florasulam | Water: 6360 mg/L<br>Acetone: 123,000 mg/L<br>Methanol: 9810 | P: 0.0603<br>log P: −1.22 |
| flumetsulam | Water: 5650 mg/L<br>Acetone: 1600 mg/L | P: 1.62<br>log P: 0.21 |
| nicosulfuron | Water: 7500 mg/L<br>Acetone: 8900 mg/L<br>Methanol: 400 mg/L | P: 4.07<br>log P: 0.61 |
| metsulfuron-methyl | Water: 2790 mg/L<br>Acetone: 37000 mg/L<br>Methanol: 7630 mg/L | P: 0.02<br>log P: −1.7 |
| tribenuron-methyl | Water: 2040 mg/L<br>Acetone: 39100 mg/L | P: 6.02<br>log P: 0.78 |
| chlorsulfuron | Water: 12500 mg/L | P: 0.1<br>log P: −0.99 |

Though the solubilities in water are above the typical application rates for sulfonylureas and sulfonamides, formulations of sulfonylureas and sulfonamides, as described below, exhibited improved efficacy and improvements as compared to current commercial formulations.

Hydrolysis

AOPPs are generally resistant to hydrolysis under neutral and acidic conditions, but become more susceptible in basic aqueous media. Table 4 provides stability data for various AOPPs in aqueous media of different pHs. Values were obtained from the e-pesticide manual, Ver. 5. British Crop Protection Council and The Pesticide Properties Database (PPDB), University of Hertfordshire. For certain applications, it would be desirable to develop formulations that increase the resistance of AOPPs to hydrolysis.

TABLE 4

Stability properties of AOPPs in various aqueous media

| Aryloxyphenoxypropionate (AOPP) | Stability properties |
|---|---|
| quizalofop-ethyl | Stable at pH 3-7 [+] |
| quizalofop-P-tefuryl | Aqueous hydrolysis $DT_{50}$ at 20° C. and pH 7: 18.2 days (Non-persistent)<br>$DT_{50}$ at pH 5.1: 8.2 days; at pH 9.2 7.2 hours<br>(all at 22° C.) [++] |
| diclofop-methyl | Aqueous hydrolysis $DT_{50}$ (days)<br>at 20° C. and pH 7: 31.7<br>DT50 at pH 5: 363 days, at pH 7: 31.7, at pH 9: 0.52 days (all at 25° C., darkness) [++] |
| propaquizafop | Hydrolytic $DT_{50}$: 10.5 d (pH 5), 32.0 d (pH 7), 12.9 h (pH 9) (all at 25° C.) [+] |
| haloxyfop-P-methyl | $DT_{50}$: 3 d (natural water), stable (pH 4), 43 d (pH 7) 0.63 d (pH 9) (all at 20° C.) [+] |
| fluazifop-P-butyl | Aqueous hydrolysis $DT_{50}$ (days) at 20° C. and pH 7: 78 Stable at pH 5, 29 hours at pH 9 (all at 25° C. darkness) [++] |
| haloxyfop | Aqueous hydrolysis $DT_{50}$ (days) at 20° C. and pH 7: Stable |
| fenoxaprop-P-ethyl | Hydrolytic $DT_{50}$: 2.8 d (pH 4), 19.2 d (pH 5), 23.2 d (pH 7), 0.6 d (pH 9) (all at 25° C.) [+] |
| clodinafop-propargyl | Relatively stable in acidic media at 50° C., hydrolyzes in alkaline media, $DT_{50}$ at 25° C.: 4.8 d (pH 7), 0.07 d (pH 9) [+] |
| cyhalofop-butyl | Aqueous hydrolysis DT50 at 20° C. and pH 7: 97 days Stable at pH 4, DT50 2 days at pH 9 (25° C.) [++] |

[+] The e-pesticide manual, Ver. 5. British Crop Protection Council
[++] The PPDB: Pesticide Properties Database (PPDB), University of Hertfordshire, http://sitem.herts.ac.uk/aeru/footprint/en/index.htm Data describing the aqueous hydrolysis of carfentrazone-ethyl and tralkoxydim, a triazolinone PPO inhibitor and CHD herbicide, respectively, are presented in Table 5. As can be seen, members of these classes of herbicides are unstable to hydrolysis in some aqueous media. For example, the triazolinone carfentrazone-ethyl is classified as non-persistent at pH 7, and undergoes rapid hydrolysis at pH 9. It would be desirable to develop formulations that increase the stability of cyclohexanedione herbicides and triazolinone inhibitors of PPO that are susceptible to hydrolysis under various conditions (e.g. increased or decreased pH).

TABLE 5

Stability properties of carfentrazone-ethyl and tralkoxydim in aqueous media

| Herbicide | Stability properties |
|---|---|
| carfentrazone-ethyl (a triazolinone) | Aqueous hydrolysis $DT_{50}$ (days) at 20° C. and pH 7: 13.7 (non-persistent) pH sensitive: stable at pH 5, $DT_{50}$ 5.1 hours at pH 9, (20° C.)[+] |
| tralkoxydim (a cyclohexanedione) | Aqueous hydrolysis $DT_{50}$ (days) at 20° C. and pH 7: 140 days (persistent) pH sensitive: $DT_{50}$ 9 days at pH 5, stable at pH 9, all at 25° C.[+] |

[+]The PPDB: Pesticide Properties Database (PPDB), University of Hertfordshire, http://sitem.herts.ac.uk/aeru/footprint/en/index.htm Sulfonamides are also generally resistant to hydrolysis in a wide range of conditions. Sulfonylureas are susceptible to more rapid degradation in acidic conditions, as noted below. Sulfonylureas are generally stable under basic and neutral conditions.

TABLE 6

Hydrolytic Stability of exemplary Sulfonamide and Sulfonylureas

| Herbicide | Aqueous hydrolysis |
|---|---|
| penoxsulam | Stable (at pH 7 and 20° C.) |
| pyroxsulam | Stable ("") |
| metosulam | Stable |
| florasulam | Stable |
| flumetsulam | Not Available |
| nicosulfuron | Stable at pH 7; 15 d at pH 5 |
| metsulfuron-methyl | Stable at pH 7; 2 d at pH 5 |
| tribenuron-methyl | DT50: 16 at pH 7; 2.2 d at pH 5 |
| chlorsulfuron | Stable at pH 7; 1 d at pH 5 |

For certain applications, it would thus be desirable to develop formulations that increase the hydrolytic stability of these herbicides.

UV Stability

As discussed above, cyclohexanedione herbicides (CHDs, DIMs) exert their phytotoxic effects through the inhibition of ACCase. These herbicides exhibit a range of susceptibilities to degradation in sunlight, as demonstrated by the $DT_{50}$ values presented in Table 7 (Data obtained from the Pesticide Properties Database (PPDB), University of Hertfordshire). The photo-instability of susceptible CHDs leads to a number of challenges related to their formulation, storage, handling, application, and persistence. For example, it is known that UV exposure can have a detrimental effect on the efficacy of members of this class of herbicide. McMullan reported that filtering UV light from treated grasses for 4 hours after the application of clethodim or tralkoxydim led to an increase of efficacy of 13-55% as compared to treatments in which UV light was not filtered (*Weed Technology* 1996, 35:72-77). Photolytic instability often necessitates the incorporation of a UV-blocker or UV-absorber into formulations of CHDs. UV-blockers can complicate formulations, as they themselves also need to be soluble or dispersible in the matrix in which the active is formulated. It is often recommended to apply CHDs in the evening or at night to avoid sunlight-mediated degradation. It would thus be desirable to develop formulations that increase the photolytic stability of the CHDs, and to provide formulations that do not require UV-blockers.

TABLE 7

Photolytic stabilities of CHD herbicides

| Cyclohexanedione (CHD) | Photolytic stability |
|---|---|
| clethodim | Aqueous photolysis $DT_{50}$ at pH 7: 5.45 days (25° C.) pH sensitive: $DT_{50}$ at pH 5: 1.6 days; at pH 9 7.79 days (all at 25° C.) [+] |
| tralkoxydim | Aqueous photolysis $DT_{50}$ at pH 7: 5.8 days 5.8 [+] |
| aloxydim | Aqueous photolysis $DT_{50}$ at pH 7: 0.22 days [+] |
| cycloxydim | Aqueous photolysis $DT_{50}$ at pH 7: 0.05 days [+] |
| sethoxydim | Aqueous photolysis $DT_{50}$ at pH 7: 0.02 days [+] |

[+] The PPDB: Pesticide Properties Database (PPDB), University of Hertfordshire, http://sitem.herts.ac.uk/aeru/footprint/en/index.htm.

Table 8 provides data related to photolytic stability of AOPPs, which display a range of susceptibilities to light-mediated degradation (data obtained from the e-pesticide manual, Ver. 5. British Crop Protection Council and the Pesticide Properties Database). Some AOPPs, such as haloxyfop-P, quizalofop-P-tefuryl and fluazifop-P-butyl, are degraded quickly or moderately quickly in the presence of light. The triazolinone azafenidin undergoes rapid aqueous photolysis ($DT_{50}$ 0.5 days, Pesticide Properties Database). For certain applications, it would thus be desirable to develop formulations that increase the photolytic stability of these herbicides.

TABLE 8

Photolytic stabilities of various AOPPs

| Aryloxyphenoxypropionate (AOPP) | Photolytic stability |
|---|---|
| quizalofop-ethyl | Unstable to light ($DT_{50}$ 10-30 days)[+] |
| diclofop-methyl | Aqueous photolysis $DT_{50}$ at pH 7: 22 days[++] |
| Propaquizafop | Stable to UV light[+] |
| haloxyfop-P-methyl | Aqueous photolysis $DT_{50}$ at pH 7: 20 days[++] |
| fluazifop-P-butyl | Aqueous photolysis $DT_{50}$ at pH 7: 6 days (moderately fast)[++] |
| Haloxyfop | Aqueous photolysis $DT_{50}$ at pH 7: 12 days (moderately fast)[++] |
| haloxyfop-P | Aqueous photolysis $DT_{50}$ at pH 7: 12 days (moderately fast)[++] |
| fenoxaprop-P-ethyl | Not sensitive to light[+] Aqueous photolysis $DT_{50}$ at pH 7: 105 days (stable)[++] |
| clodinafop-propargyl | Aqueous photolysis $DT_{50}$ at pH 7: 24 days (stable)[++] |
| quizalofop-P-tefuryl | Aqueous photolysis $DT_{50}$ at pH 7: 1.0 days (moderately fast)[++] |

[+]The e-pesticide manual, Ver. 5. British Crop Protection Council
[++]The PPDB: Pesticide Properties Database (PPDB), University of Hertfordshire, http://sitem.herts.ac.uk/aeru/footprint/en/index.htm Similarly, sulfonamide and sulfonylureas exhibit a wide array of UV stability values. Some sulfonamides (e.g., pyroxsulam) being very sensitive to light while other sulfonamides are stable. For certain applications, it would thus be desirable to develop formulations that increase the photolytic stability of these herbicides.

TABLE 9

Photolytic Stability of Exemplary Sulfonamides and Sulfonylureas

| Herbicide | Photolytic stability |
|---|---|
| penoxsulam | DT50: 2 d (at pH 7) |
| pyroxsulam | DT50: 3.2 d ("") |
| metosulam | DT50: 31.1 d |

TABLE 9-continued

Photolytic Stability of Exemplary Sulfonamides and Sulfonylureas

| Herbicide | Photolytic stability |
|---|---|
| florasulam | DT50: 156 d |
| flumetsulam | DT50: 270 d |
| nicosulfuron | DT50: 202 d |
| metsulfuron-methyl | Stable |
| tribenuron-methyl | Stable |
| chlorsulfuron | DT50: 18.8 d |

Improved Foliar Uptake

Upon foliar inoculation of a pestilent plant, the applied herbicide must absorb into the plant's tissues and reach its target site to exert its phytotoxic effects. It follows that one method of increasing the efficacy of an active ingredient is improving its foliar uptake. A slow or less that optimal rate of uptake could potentially lead to degradation of the active (e.g. hydrolysis or light-mediated degradation of AOPPs, CHDs and triazolinones, as described above) prior to absorption. In addition, a recurrent concern in the application of herbicides is loss of the active ingredient via run-off, which leads to undesired contamination of systems that have not been inoculated. An increased rate of foliar uptake is one strategy for improving localization of the applied herbicide and decreasing contamination. It would thus be desirable to develop formulations of AOPPs, CHDs and triazolinones that impart improved absorption properties to the active, such as more rapid absorption. Furthermore, it would be desirable to develop formulations that impart both improved stability properties (e.g. increased hydrolytic stability) and increased foliar absorption. Improving the uptake of the active ingredient and reducing its degradation prior to uptake is an excellent method of improving net efficacy.

Suspension Concentrates

Most commercially available liquid formulations of AOPPs are ECs, which, as discussed above, are formulations in which the active ingredient is dissolved in an organic solvent and emulsified into water with surfactants. The incorporation of surfactants and organic solvents into ECs is one of their inherent disadvantages. For example, storage, handling, transportation and application concerns arise due to the toxicity (e.g. phytotoxicity, dermal toxicity) and physical properties (e.g. flammability) of organic solvents. In addition, ECs are known to destabilize via a number of mechanisms such as coalescence upon storage or heating.

In contrast to ECs, SCs are high-solids concentrates of suspended active ingredient in water, and as such, do not have disadvantages related to the incorporation of organic solvents. While it would thus be desirable to provide formulations of herbicides as SCs, there are a number of issues that complicate their preparation. For example, low-melting point actives melt due to the heat generated during the milling process, and suspension concentrates of liquid active ingredients are traditionally very difficult to prepare. In addition, suspension concentrates have their own issues related to stability and storage. For example, degradation of sensitive active ingredients (e.g. hydrolysis of AOPPs) can occur during formulation or storage, and many SCs display sensitivity to increased temperature and temperature cycling. In the absence of sufficiently effective stabilizing agents, phase separation of the active ingredient in the concentrate can also occur. Moderately or highly water-soluble active ingredients are not generally suitable for formulation into SCs, as they tend to destabilize via recrystallization.

Thus, it would be desirable to provide SCs or concentrated aqueous suspension formulations of AOPPs, CHDs, triazolinone inhibitors of PPOs, sulfonamides and sulfonylureas particularly formulations that exhibit enhanced stability properties. In addition, there remains a need to develop methods that facilitate the preparation of such concentrates of these herbicides.

High Salt Formulations

In many cases, formulations of herbicides are mixed with other agricultural products such as concentrated fertilizer mix, exposed to high salt or ion conditions (e.g. used in or with hard waters), mixed with other formulations (other pesticides, fungicides, and herbicides), or mixed with tank-mix adjutants. These types of applications can be beneficial to the end user, as they allow for multiple agricultural products to be applied in a single application. It would thus be desirable to develop formulations of AOPPs, CHDs, triazolinone inhibitors of PPOs, sulfonamides and sulfonylureas that are stable under high-salt conditions.

Formulations—Testing and Properties

After producing granulated, powdered, and high-concentration liquid suspension formulations, biological activities were evaluated. The Examples provide a detailed description of the experiments that were performed. Here we provide a summary.

In one example, a wettable powder formulation of nanoparticles of polymer associated fenoxaprop-P-ethyl prepared according to the present invention (also referred to herein as the nano-formulation) and a commercial formulation of fenoxaprop-P-ethyl were compared for efficacy against green foxtail, corn, and oat under controlled environmental conditions. Briefly, the nanoparticle formulation and commercial formulation were applied to plants at a various active ingredient doses using a sprayer. Approximately 14 days after treatment (DAT), shoots were clipped at the soil surface, and plant biomass was compared to an untreated control. The dose required by both formulations to reduce green foxtail, corn, and oat seedling growth by 50% ($GR_{50}$) was then determined.

We found that our nanoparticle formulation of fenoxaprop-P-ethyl had greater efficacy consistently on green foxtail and corn than the commercial formulation. For green foxtail and corn, the dose of the nanoparticle formulation required to reduce plant biomass by 50% ($GR_{50}$) was approximately 50% of that of the commercial formulation of fenoxaprop-P-ethyl. In addition, the nanoparticle formulation of fenoxaprop-P-ethyl was equal to or better for the control of the more tolerant oat species compared to the standard commercial formulation.

In other examples, wettable powder formulation of nanoparticles of polymer associated pyroxsulam were compared to commercial formulations of pyroxsulam and tested against several species of weeds. The formulations were applied by foliar spray as several different application rates. Control of the weed species were evaluated at various times between 14 and 87 days after application. It was found that nano-formulations produced equal or enhanced control of weed species. Such improvements were not expected due to the solubility of pyroxsulam due to the solubility of pyroxsulam in water relative to the application rates.

Formulations—Components

In various aspects, the present invention provides formulations that comprise nanoparticles (optionally in aggregate form) of polymer-associated active ingredient along with various formulating agents.

Active Ingredient As used herein, the terms "active ingredient" and "herbicide" refer to herbicidal chemical compounds selected from the group consisting of Aryloxyphenoxypropionate herbicides (AOPPs, FOPs), cyclohexanedione herbicides (CHDs, DIMs), and triazolinones and combinations thereof.

In some embodiments the active ingredient is an Aryloxyphenoxypropionate (AOPP) herbicide. In some embodiments, AOPPs are esters derived from their parent free acids, which are themselves AOPPs. Exemplary substructures of AOPPs are shown below:

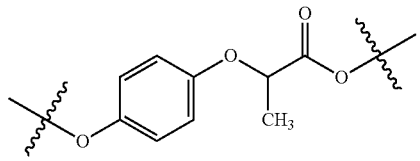

and the (R) enantiomers:

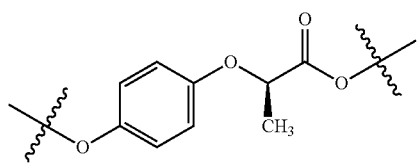

Non-limiting examples of AOPPs are: quizalofop, (RS)-2-[4-(6-chloroquinoxalin-2-yloxy)phenoxy]propionic acid; quizalofop-ethyl, ethyl (2RS)-2-[4-(6-chloroquinoxalin-2-yloxy)phenoxy]propionate; quizalofop-P-ethyl, ethyl (2R)-2-[4-(6-chloroquinoxalin-2-yloxy)phenoxy]propionate; clodinafop, (R)-2-[4-(5-chloro-3-fluoro-2-pyridyloxy)phenoxy]propionic acid; clodinafop-propargyl, prop-2-ynyl (R)-2-[4-(5-chloro-3-fluoro-2-pyridyloxy)phenoxy]propionate; quizalofop, (RS)-2-[4-(6-chloroquinoxalin-2-yloxy)phenoxy]propionic acid; quizalofop-P, (R)-2-[4-(6-chloroquinoxalin-2-yloxy)phenoxy]propionic acid; quizalofop-ethyl, (2RS)-2-[4-(6-chloroquinoxalin-2-yloxy)phenoxy]propionate; quizalofop-P-ethyl, ethyl (2R)-2-[4-(6-chloroquinoxalin-2-yloxy)phenoxy]propionate; clofop, (RS)-2-[4-(4-chlorophenoxy)phenoxy]propionic acid; clofop-isobutyl, (RS)-2-[4-(4-chlorophenoxy)phenoxy]propionate; cyhalofop, (R)-2-[4-(4-cyano-2-fluorophenoxy)phenoxy]propionic acid; cyhalofop-butyl, butyl (R)-2-[4-(4-cyano-2-fluorophenoxy)phenoxy]propionate; diclofop, (RS)-2-[4-(2,4-dichlorophenoxy)phenoxy]propionic acid, diclofop-methyl, methyl (RS)-2-[4-(2,4-dichlorophenoxy)phenoxy]propionate; diclofop-P-methyl, methyl (R)-2-[4-(2,4-dichlorophenoxy)phenoxy]propionate; propaquizafop, 2-isopropylideneaminooxyethyl (R)-2-[4-(6-chloroquinoxalin-2-yloxy)phenoxy]propionate; trifop, (RS)-2-[4-(α,α,α-trifluoro-p-tolyloxy)phenoxy]propionic acid; trifop-methyl, methyl (RS)-2-[4-(α,α,α-trifluoro-p-tolyloxy)phenoxy]propionate and; haloxyfop, (RS)-2-{4-[3-chloro-5-(trifluoromethyl)-2-pyridyloxy]phenoxy}propionic acid; haloxyfop-P, (R)-2-{4-[3-chloro-5-(trifluoromethyl)-2-pyridyloxy]phenoxy}propionic acid; haloxyfop-methyl, methyl (RS)-2-{4-[3-chloro-5-(trifluoromethyl)-2-pyridyloxy]phenoxy}propionate; haloxyfop-P-methyl methyl (R)-2-{4-[3-chloro-5-(trifluoromethyl)-2-pyridyloxy]phenoxy}propionate; fluazifop, (RS)-2-{4-[5-(trifluoromethyl)-2-pyridyloxy]phenoxy}propionic acid, fluazifop-P, (R)-2-{4-[5-(trifluoromethyl)-2-pyridyloxy]phenoxy}propionic acid; fluazifop-butyl, butyl (RS)-2-{4-[5-(trifluoromethyl)-2-pyridyloxy]phenoxy}propionate; fluazifop-P-butyl, butyl (R)-2-{4-[5-(trifluoromethyl)-2-pyridyloxy]phenoxy}propionate; fenthiaprop, (RS)-2-[4-(6-chloro-1,3-benzothiazol-2-yloxy)phenoxy]propionic acid or (RS)-2-[4-(6-chlorobenzothiazol-2-yloxy)phenoxy]propionic acid; fenthiaprop-ethyl, ethyl (RS)-2-[4-(6-chloro-1,3-benzothiazol-2-yloxy)phenoxy]propionate or ethyl (RS)-2-[4-(6-chlorobenzothiazol-2-yloxy)phenoxy]propionate; fenoxaprop, (RS)-2-[4-(6-chloro-1,3-benzoxazol-2-yloxy)phenoxy]propionic acid or (RS)-2-[4-(6-chlorobenzoxazol-2-yloxy)phenoxy]propionic acid; fenoxaprop-P, (R)-2-[4-(6-chloro-1,3-benzoxazol-2-yloxy)phenoxy]propionic acid or (R)-2-[4-(6-chlorobenzoxazol-2-yloxy)phenoxy]propionic acid; fenoxaprop-ethyl, ethyl (RS)-2-[4-(6-chloro-1,3-benzoxazol-2-yloxy)phenoxy]propionate or ethyl (RS)-2-[4-(6-chlorobenzoxazol-2-yloxy)phenoxy]propionate; fenoxaprop-P-ethyl, ethyl (R)-2-[4-(6-chloro-1,3-benzoxazol-2-yloxy)phenoxy]propionate or ethyl (R)-2-[4-(6-chlorobenzoxazol-2-yloxy)phenoxy]propionate; metamifop, (R)-2-[4-(6-chloro-1,3-benzoxazol-2-yloxy)phenoxy]-2'-fluoro-N-methylpropionanilide. In some embodiments, the active ingredient of the present invention is an agriculturally acceptable salt of an AOPP herbicide.

In some embodiments, the active ingredient of the present invention is a cyclohexanedione herbicide (CHD, DIM). An exemplary substructure of a cyclohexanedione is shown below:

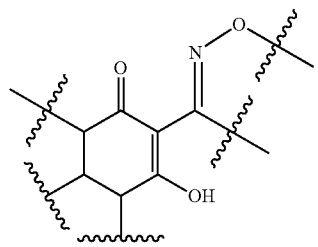 [SMILES: *O/N=C(\*)C1=C(O)C(*)C(*)C(*)C1=O]

Non-limiting examples of cyclohexanedione herbicides are: alloxydim, methyl (1RS)-3-[(E)-1-(allyloxyimino)butyl]-4-hydroxy-6,6-dimethyl-2-oxocyclohex-3-enecarboxylate; butroxydim, (5RS)-5-(3-butyryl-2,4,6-trimethylphenyl)-2-[(EZ)-1-(ethoxyimino)propyl]-3-hydroxycyclohex-2-en-1-one; clethodim, (5RS)-2-{(1EZ)-1-[(2E)-3-chloroallyloxyimino]propyl}-5-[(2RS)-2-(ethylthio)propyl]-3-hydroxycyclohex-2-en-1-one; cloproxydim, (5RS)-2-{(EZ)-1-[(2EZ)-3-chloroallyloxyimino]butyl}-5-[(2RS)-2-(ethylthio)propyl]-3-hydroxycyclohex-2-en-1-one; cycloxydim, (5RS)-2-[(EZ)-1-(ethoxyimino)butyl]-3-hydroxy-5-[(3RS)-thian-3-yl]cyclohex-2-en-1-one; profoxydim, (5RS)-2-{(EZ)-1-[(2RS)-2-(4-chlorophenoxy)propoxyimino]butyl}-3-hydroxy-5-[(3RS)-thian-3-yl]cyclohex-2-en-1-one; sethoxydim, (5RS)-2-[(EZ)-1-(ethoxyimino)butyl]-5-[(2RS)-2-(ethylthio)propyl]-3-hydroxycyclohex-2-en-1-one; tepraloxydim, (5RS)-2-{(EZ)-1-[(2E)-3-chloroallyloxyimino]propyl}-3-hydroxy-5-perhydropyran-4-ylcyclohex-2-en-1-one; tralkoxydim, (RS)-2-[(EZ)-1-(ethoxyimino)propyl]-3-hydroxy-5-mesitylcyclohex-2-en-1-one. In some embodiments, the active ingredient of the present invention is an agriculturally acceptable salt of a cyclohexanedione herbicide.

In some embodiments, the active ingredient of the present invention is a triazolinone herbicide. More preferably, in some embodiments, the active ingredient of the current invention is a triazolinone or more specifically a triazolinone inhibitor of protoporphyrinogen oxidase (PPO). An exemplary substructure of a triazolinone is shown below:

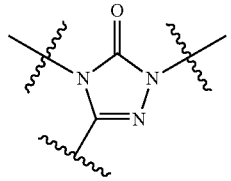 [SMILES: *c1nn(*)c(=O)n1*]

Non-limiting examples of triazolinone inhibitors of PPO are: azafenidin, 2-(2,4-dichloro-5-prop-2-ynyloxyphenyl)-5,6,7,8-tetrahydro-1,2,4-triazolo[4,3-a]pyridin-3(2H)-one; carfentrazone, (RS)-2-chloro-3-{2-chloro-5-[4-(difluoromethyl)-4,5-dihydro-3-methyl-5-oxo-1H-1,2,4-triazol-1-yl]-4-fluorophenyl}propionic acid; carfentrazone-ethyl, ethyl (RS)-2-chloro-3-{2-chloro-5-[4-(difluoromethyl)-4,5-dihydro-3-methyl-5-oxo-1H-1,2,4-triazol-1-yl]-4-fluorophenyl}propionate; sulfentrazone, 2',4'-dichloro-5'-(4-difluoromethyl-4,5-dihydro-3-methyl-5-oxo-1H-1,2,4-triazol-1-yl)methanesulfonanilide. In some embodiments, the active ingredient of the present invention is an agriculturally acceptable salt of a triazolinone inhibitor of protoporphyrinogen oxidase.

In some embodiments, the active ingredient of the present invention is a sulfonamide herbicide. More preferably, in some embodiments, the active ingredient of the current invention is a sulfonamide or more specifically a sulfonamide inhibitor of ALS. An exemplary substructure of a sulfonamide is shown below:

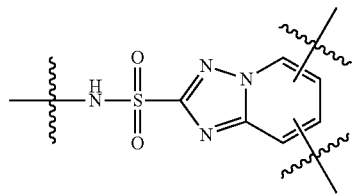

Non-limiting examples of sulfonamides include: pyroxsulam, asulam, carbasulam, fenasulam, oryzalin, and penoxsulam.

In some embodiments, the active ingredient of the present invention is a sulfonylurea herbicide. More preferably, in some embodiments, the active ingredient of the current invention is a sulfonylurea or more specifically a sulfonylurea inhibitor of ALS. An exemplary substructure of a sulfonylurea is shown below:

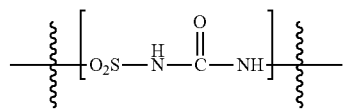

Non-limiting examples of sulfonylurea herbicides include: amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, methiopyrisulfuron, monosulfuron, nicosulfuron, orthosulfamuron, oxasulfuron, primisulfuron, propyrisulfuron, pyrazosulfuron, rimsulfuron, sulfometuron, sulfosulfuron, and trifloxysulfuron.

In some embodiments, the active ingredient of the present invention has a solubility of not more than 100,000 mg/L in water at 20° C. In some embodiments, the active ingredient of the present invention has a solubility of not more than 10,000 mg/L in water at 20° C. In some embodiments, the active ingredient of the present invention has a solubility of not more than 5000 mg/L in water at 20° C. In some embodiments, the active ingredient of the present invention has a solubility of not more than 1000 mg/L in water at 20° C. In some embodiments, the active ingredient of the present invention has a solubility of not more than 500 mg/L in water at 20° C. In some embodiments, the active ingredient of the present invention has a solubility of not more than 300 mg/L in water at 20° C. In some embodiments, the active ingredient of the present invention has a solubility of not more than 200 mg/L in water at 20° C. In some embodiments, the active ingredient of the present invention has a solubility of not more than 100 mg/L in water at 20° C. In some embodiments, the active ingredient of the present invention has a solubility of not more than 50 mg/L in water at 20° C. In some embodiments, the active ingredient of the present invention has a solubility of not more than 30 mg/L in water at 20° C. In some embodiments, the active ingredient of the present invention has a solubility of not more than 20 mg/L in water at 20° C. In some embodiments, the active ingredient of the present invention has a solubility of not more than 10 mg/L in water at 20° C. In some embodiments, the active ingredient of the present invention has a solubility of not more than 5 mg/L in water at 20° C. In some embodiments, the active ingredient of the present invention has a solubility of not more than 2 mg/L in water at 20° C. In some embodiments, the active ingredient of the present invention has a solubility of not more than 1 mg/L in water at 20° C. In some embodiments the solubility of the active ingredient in water can also be adjusted by adjusting pH or other solution conditions in water.

In some embodiments, the active ingredient is a thiadiazole herbicide. Non-limiting examples of thiadiazole herbicides include fluthiacet, {2-chloro-4-fluoro-5-[(EZ)-5,6,7,8-tetrahydro-3-oxo-1H,3H-[1,3,4]thiadiazolo[3,4-a]pyridazin-1-ylideneamino]phenylthio}acetic acid and fluthiacet-methyl, methyl{2-chloro-4-fluoro-5-[(EZ)-5,6,7,8-tetrahydro-3-oxo-1H,3H-[1,3,4]thiadiazolo[3,4-a]pyridazin-1-ylideneamino]phenylthio}acetate. In some embodiments, the active ingredient of the present invention is an agriculturally acceptable salt of a thiadiazole.

Herbicide Safeners

In some embodiments, a formulation may include a herbicide safener. Herbicide safeners reduce or eliminate the phytotoxic effects of the active ingredient against non-target plant species (e.g. crops), while maintaining acceptable levels of efficacy against target species (e.g. weeds). Examples of herbicide safeners include, but are not limited to benoxacor, (RS)-4-dichloroacetyl-3,4-dihydro-3-methyl-2H-1,4-benzoxazine; cloquintocet, (5-chloroquinolin-8-yloxy)acetic acid; cloquintocet-mexyl, (RS)-1-methylhexyl (5-chloroquinolin-8-yloxy)acetate; cyometrinil, (Z)-cyanomethoxyimino(phenyl)acetonitrile; cyprosulfamide, N-[4-(cyclopropylcarbamoyl)phenylsulfonyl]-o-anisamide or N-[4-(cyclopropylcarbamoyl)phenylsulfonyl]-2-methoxybenzamide; dichlormid, N,N-diallyl-2,2-dichloroacetamide; dicyclonon, (RS)-1-dichloroacetyl-3,3,8a-trimethylperhydropyrrolo[1,2-a]pyrimidin-6-one; dietholate, O,O-diethyl O-phenyl phosphorothioate; fenchlorazole, 1-(2,4-dichlorophenyl)-5-trichloromethyl-1H-1,2,4-triazole-3-carboxylic acid; fenchlorazole-ethyl, ethyl 1-(2,4-dichlorophenyl)-5-trichloromethyl-1H-1,2,4-triazole-3-carboxylate; fenclorim, 1-(2,4-dichlorophenyl)-5-trichloromethyl-1H-1,2,4-triazole-3-carboxylic acid; flurazole, benzyl 2-chloro-4-trifluoromethyl-1,3-thiazole-5-carboxylate or benzyl 2-chloro-4-trifluoromethylthiazole-5-carboxylate; fluxofenim, 4'-chloro-2,2,2-trifluoroacetophenone (EZ)—O-1,3-dioxolan-2-ylmethyloxime; furilazole, (RS)-3-dichloroacetyl-5-(2-furanyl)-2,2-dimethyl-1,3-oxazolidine; isoxadifen, 4,5-dihydro-5,5-diphenyl-1,2-oxazole-3-carboxylic acid; isoxadifen-ethyl, ethyl 4,5-dihydro-5,5-diphenyl-1,2-oxazole-3-carboxylate; jiecaowan, 2-(dichloromethyl)-2-methyl-1,3-dioxolane; jiecaoxi, N-allyl-N-(allylcarbamoylmethyl)-2,2-dichloroacetamide; mephenate, 4-chlorophenyl methylcarbamate; naphthalic anhydride, naphthalene-1,8-dicarboxylic anhydride; oxabetrinil, (Z)-1,3-dioxolan-2-ylmethoxyimino(phenyl)acetonitrile; mefenpyr, (RS)-1-(2,4-dichlorophenyl)-5-methyl-2-pyrazoline-3,5-dicarboxylic acid; mefenpyr-diethyl, diethyl (RS)-1-(2,4-dichlorophenyl)-5-methyl-2-pyrazoline-3,5-dicarboxylate, MG-191, 2-(dichloromethyl)-2-methyl-1,3-dioxolane and combinations thereof; (names of most of the tabulated safeners were obtained from http://www.alanwood.net, "Compendium of Pesticide Common Names").

In some embodiments, the herbicide safener is an agriculturally acceptable salt of cloquintocet, fenchlorazole and mefenpyr, isoxadifen, combinations thereof, or combinations of one or more of these salts with any of the safeners listed above.

In preferred embodiments, the herbicide safener is selected from the group consisting of mefenpyr-diethyl, isoxadifen-ethyl and cloquintocet-mexyl.

In some embodiments, formulations of the present invention comprising AOPP herbicides include a safener that is selected from the group consisting of of mefenpyr-diethyl, isoxadifen-ethyl and cloquintocet-mexyl.

The ratio of active ingredient to herbicide safener can vary widely depending on the characteristics of the active ingredient, safener, formulation, and particular application. In some embodiments, the ratio of active ingredient to herbicide safener (by weight) can be between 100:1 and 1:100, 100:1 and 1:50, 100:1 and 1:20, 100:1 and 1:10, 100:1 and 1:1, 100:1 and 100:10, 50:1 and 1:100, 20:1 and 1:100, 10:1 and 1:100, 1:1 and 1:100, or 1:10 and 1:100. In some embodiments, the ratio of active ingredient to herbicide safener (by weight) can be between 50:1 and 1:50, 50:1 and 1:20, 50:1 and 1:10, 50:1 and 1:1, 20:1 and 1:50, 10:1 and 1:50, or 1:1 and 1:50. In some embodiments, the ratio of active ingredient to herbicide safener (by weight) can be between 20:1 and 1:20, 20:1 and 1:10, 20:1 and 1:1, 10:1 and 1:20, 1:1 and 1:20, 10:1 and 1:10, 10:1 and 1:1, 1:1 and 1:10, or 5:1 and 1:5.

Nanoparticles of Polymer-Associated Active Ingredient and Optionally Herbicide Safener As used herein, the terms "nanoparticles of polymer-associated active ingredient" and "active ingredient associated with polymer nanoparticles" refer to nanoparticles comprising one or more collapsed polymers that are associated with the active ingredient. In some embodiments the collapsed polymers are cross-linked. As discussed below, in some embodiments, our formulations may include aggregates of nanoparticles. Exemplary polymers and methods of preparing nanoparticles of polymer-associated active ingredient are described more fully below.

In some embodiments, the active ingredient is associated with preformed polymer nanoparticles. The associating step may involve dispersing the polymer nanoparticles in a first solvent and then dissolving or dispersing the active ingredient in a second solvent that is miscible or partially miscible with the first solvent, which may or may not be different than the first solvent, mixing the two dispersions and then either removing the second or first solvent from the final mixture. In some embodiments, all of the solvent is removed by vacuum evaporation, freeze drying or spray drying. The associating step may also involve dispersing both the polymer nanoparticles and active ingredients in a common solvent and removing all or a portion of the common solvent from the final mixture. The associating step may also involve dispersing both the polymer nanoparticles and active ingredients in a common solvent system comprising two solvents, and removing all or a portion of either of the solvents, or all or a portion of the common solvent system from the final mixture.

In some embodiments, the associating step may involve comminution of the active ingredient in the presence of pre-formed nanoparticles. In comminution processes, solid materials are reduced in size (e.g. reduced in size to small particles). Size reduction can be achieved by a variety of mechanical methods including grinding, crushing and milling. In preferred embodiments, the associating step may involve wet or dry milling of the active ingredient in the presence of pre-formed nanoparticles. In milling processes, size reduction occurs via collisions of the solid active ingredient with the milling media, which leads to breakage and fracturing. Non-limiting examples of milling methods can be found in U.S. Pat. No. 6,604,698 and include ball milling, bead milling, jet milling, media milling, and homogenization, as well as other milling methods capable of comminution of the active ingredient. Non-limiting examples of mills that can be used for the comminution process include attritor mills, ball mills, colloid mills, high pressure homogenizers, horizontal mills, jet mills, swinging mills, and vibratory mills. In some embodiments, the associating step may involve milling the active ingredient in the presence of pre-formed polymer nanoparticles and an aqueous phase.

In general, the active ingredient may be associated with regions of the polymer nanoparticle that elicit a chemical or physical interaction with the active ingredient. Chemical interactions can include hydrophobic interactions, affinity pair interactions, H-bonding, and van der Waals forces. Physical interactions can include entanglement in polymer chains and inclusion within the polymer nanoparticle structure. The active ingredient can be associated in the interior of the polymer nanoparticle, on the surface of the polymer nanoparticle, or both the surface and the interior of the polymer nanoparticle. Furthermore, the type of association interactions between the active ingredient and the polymer nanoparticle can be probed using spectroscopic techniques such as NMR, IR, UV-vis, and emission spectroscopies, or any of variety of other analytical techniques known to those skilled in the art. For example, in cases where the active ingredient is normally crystalline when not associated with the polymer nanoparticles, the nanoparticles of polymer-associated AOPP compounds show a reduced endothermic melting peak of the pure crystalline active ingredient as seen in differential thermal analysis (DTA) or differential scanning calorimetry (DSC) measurements.

In some embodiments, active ingredient and herbicide safener are associated with pre-formed nanoparticles. Thus, in some embodiments, the invention provides nanoparticles of active ingredients and herbicide safeners. As used herein, the term "nanoparticles of polymer-associated active ingredient and herbicide safener", "nanoparticles of polymer-associated AOPP compound and herbicide safener" or "active ingredient and herbicide safener associated with polymer nanoparticles" refer to nanoparticles comprising one or more collapsed polymers that are associated with the active ingredient and herbicide safener. In some embodiments the collapsed polymers are cross-linked. As discussed below, in some embodiments, our formulations may include aggregates of nanoparticles. Exemplary polymers and methods of preparing nanoparticles of polymer-associated active ingredient and herbicide safener are described more fully below.

In some embodiments, the active ingredient and herbicide safener are associated with preformed polymer nanoparticles. The associating step may involve dispersing the polymer nanoparticles in a first solvent and then dissolving or dispersing the active ingredient and herbicide safener in a second solvent that is miscible or partially miscible with the first solvent, and which may or may not be different than the first solvent, mixing the two dispersions and then either removing the second or first solvent from the final mixture. In some embodiments, all the solvent is removed by vacuum evaporation, freeze drying or spray drying. The associating step may also involve dispersing the polymer nanoparticles, active ingredients and herbicide safener in a common solvent and removing all or a portion of the common solvent from the final mixture. The associating step may also involve dispersing the polymer nanoparticles, herbicide safener, and active ingredients in a common solvent system comprising two solvents, and removing all or a portion of either of the solvents, or all or a portion of the common solvent system from the final mixture.

In some embodiments, the associating step may involve comminution of the active ingredient and herbicide safener in the presence of pre-formed nanoparticles. In some embodiments, the associating step may involve comminution of the active ingredient in the presence of herbicide safener and pre-formed nanoparticles. In some embodiments, the associating step may involve comminution of the herbicide safener in the presence of active ingredient and pre-formed nanoparticles. In preferred embodiments, the associating step may involve wet or dry milling of the active ingredient and herbicide safener in the presence of pre-formed nanoparticles. In milling processes, size reduction occurs via collisions of the solid active ingredient with the milling media, which leads to breakage and fracturing. Non-limiting examples of milling methods can be found in U.S. Pat. No. 6,604,698 and include ball milling, bead milling, jet milling, media milling, and homogenization, as well as other milling methods capable of comminution of the active ingredient. Non-limiting examples of mills that can be used for the comminution process include attritor mills, ball mills, colloid mills, high pressure homogenizers, horizontal mills, jet mills, swinging mills, and vibratory mills. In some embodiments, the associating step may involve milling the active ingredient and herbicide safener in the presence of pre-formed polymer nanoparticles and an aqueous phase.

Nanoparticles of polymer-associated active ingredients and optionally herbicide safeners, can be prepared with a range of average diameters, e.g., between about 1 nm and about 500 nm. The size of the nanoparticles can be adjusted in part by varying the size and number of polymers that are included in the nanoparticles. In some embodiments, the average diameter ranges from about 1 nm to about 10 nm, from about 1 nm to about 20 nm, from about 1 nm to about 30 nm, from about 1 nm to about 50 nm, from about 10 nm to about 50 nm, from about 10 nm to about 100 nm, from about 20 nm to about 100 nm, from about 20 nm to about 100 nm, from about 50 nm to about 200 nm, from about 50 nm to about 250 nm, from about 50 nm to about 300 nm, from about 100 nm to about 250 nm, from about 100 nm to about 300 nm, from about 200 nm to about 300 nm, from about 200 nm to about 500 nm, from about 250 nm to about 500 nm, and from about 300 nm to about 500 nm. These and other average diameters described herein are based on volume average particle sizes that were measured in solution by dynamic light scattering on a Malvern Zetasizer ZS in CIPAC D water, 0.1M NaCl, or in deionized water at 200 ppm active concentration. Various forms of microscopies can also be used to visualize the sizes of the nanoparticles such as atomic force microscopy (AFM), transmission electron microscopy (TEM), scanning electron microscopy (SEM) and optical microscopy.

As mentioned above, in some embodiments, the formulation may comprise aggregates of nanoparticles comprising polymer-associated active ingredients and optionally herbicide safeners. In some embodiments, these aggregates can be loose aggregates that can be separated into isolated nanoparticles by vigorous mixing, sonication, dilution, etc. In some embodiments, these aggregates are hard aggregates that cannot be separated using simple physical techniques. In some embodiments, the aggregates are aggregated due to interactions between active ingredients exposed on the surfaces of the nanoparticles. In some embodiments, the aggregates have an average particle size between about 10 nm and about 5,000 nm when dispersed in water under suitable conditions. In some embodiments, the aggregates have an average particle size between about 10 nm and about 1,000 nm. In some embodiments, the aggregates have an average particle size between about 10 nm and about 500 nm. In some embodiments, the aggregates have an average particle size between about 10 nm and about 300 nm. In some embodiments, the aggregates have an average particle size between about 10 nm and about 200 nm. In some embodiments, the aggregates have an average particle size between about 50 nm and about 5,000 nm. In some embodiments, the aggregates have an average particle size between about 50 nm and about 1,000 nm. In some embodiments, the aggregates have an average particle size between about 50 nm and about 500 nm. In some embodiments, the aggregates have an average particle size between about 50 nm and about 300 nm. In some embodiments, the aggregates have an average particle size between about 50 nm and about 200 nm. In some embodiments, the aggregates have an average particle size between about 100 nm and about 5,000 nm. In some embodiments, the aggregates have an average particle size between about 100 nm and about 1,000 nm. In some embodiments, the aggregates have an average particle size between about 100 nm and about 500 nm. In some embodiments, the aggregates have an average particle size between about 100 nm and about 300 nm. In some embodiments, the aggregates have an average particle size between about 100 nm and about 200 nm. In some embodiments, the aggregates have an average particle size between about 500 nm and about 5000 nm. In some embodiments, the aggregates have an average particle size between about 500 nm and about 1000 nm. In some embodiments, the aggregates have an average particle size between about 1000 nm and about 5000 nm. Particle size can be measured by dynamic light scattering as described above.

In some embodiments, the nanoparticles are prepared using a polymer that is a polyelectrolyte. Polyelectrolytes are polymers that contain monomer units of ionized or ionizable functional groups, they can be linear, branched, hyperbranched or dendrimeric, and they can be synthetic or naturally occurring. Ionizable functional groups are functional groups that can be rendered charged by adjusting solution conditions, while ionized functional group refers to chemical functional groups that are charged regardless of solution conditions. The ionized or ionizable functional group can be cationic or anionic, and can be continuous along the entire polymer chain (e.g., in a homopolymer), or can have different functional groups dispersed along the polymer chain, as in the case of a co-polymer (e.g., a random co-polymer). In some embodiments, the polymer can be made up of monomer units that contain functional groups that are either anionic, cationic, both anionic and cationic, and can also include other monomer units that impart a specific desirable property to the polymer.

In some embodiments, the polyelectrolyte is a homopolymer. Non limiting examples of homopolymer polyelectrolytes are: poly(acrylic acid), poly(methacrylic acid), poly(styrene sulfonate), poly(ethyleneimine), chitosan, poly(dimethylammonium chloride), poly(allylamine hydrochloride), and carboxymethyl cellulose.

In some embodiments, the polyelectrolyte is a co-polymer. In some embodiments, the polyelectrolyte co-polymer is poly(methacrylic acid-co-ethyl acrylate); poly(methacrylic acid-co-styrene); poly(methacrylic acid-co-butylmethacrylate); poly(ethylene glycol methyl ether methacrylate); or poly(n-butylmethacrylcate-co-methacrylic acid).

In some embodiments, the polyelectrolyte can be made from one or more monomer units to form homopolymers, copolymers or graft copolymers of: carboxylic acids including acrylic acid, methacrylic acid, itaconic acid, and maleic acid; polyoxyethylenes or polyethyleneoxide; and unsaturated ethylenic mono or dicarboxylic acids; lactic acids; amino acids; amines including dimethlyammonium chloride, allylamine hydrochloride; along with other monomers such including methacrylic acid; ethyleneimine; ethylene; ethylene glycol; ethylene oxide acrylates including methyl acrylate, ethyl acrylate, propyl acrylate, n-butyl acrylate ("BA"), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate and partially hydrolyzed poly(vinyl acetate), vinylversatate, vinylpropionate, vinylformamide, vinylacetamide, vinylpyridines, and vinyllimidazole; vinylnapthalene, vinylnaphthalene sulfonate, vinylpyrrolidone, vinyl alcohol; aminoalkyls including aminoalkylacrylates, aminoalkylmethacrylates, and aminoalkyl(meth)acrylamides; styrenes including styrene sulfonate; 2-Acrylamido-2-methylpropane sulfonic acid; d-glucosamine; glucaronic acid-N-acetylglucosamine; N-isopropylacrylamide; vinyl amine. In some embodiments, the polyelectrolyte polymer can include groups derived from polysaccharides such as dextran, gums, cellulose, or carboxymethyl cellulose In some embodiments, the mass ratio of methacrylic acid to ethyl acrylate in the poly(methacrylic acid-co-ethyl acrylate)polymer is between 50:50 and 95:5. In some embodiments, the mass ratio of methacrylic acid to ethyl acrylate in the poly(methacrylic acid-co-ethyl acrylate)polymer is between 70:30 and 95:5. In some embodiments, the mass ratio of methacrylic acid to ethyl acrylate in the poly(methacrylic acid-co-ethyl acrylate)polymer is between 80:20 and 95:5. In some embodiments, the mass ratio of methacrylic acid to ethyl acrylate in the poly(methacrylic acid-co-ethyl acrylate)polymer is between 85:15 and 95:5.

In some embodiments, the mass ratio of methacrylic acid to styrene in the poly(methacrylic acid-co-styrene)polymer is between 50:50 and 95:5. In some embodiments, the mass ratio of methacrylic acid to styrene in the poly(methacrylic acid-co-styrene)polymer is between 70:30 and 95:5. In some embodiments, the mass ratio of methacrylic acid to styrene in the poly(methacrylic acid-co-styrene)polymer is between 80:20 and 95:5. In some embodiments, the mass ratio of methacrylic acid to styrene in the poly(methacrylic acid-co-styrene)polymer is between 85:15 and 95:5.

In some embodiments, the mass ratio of methacrylic acid to butyl methacrylate in the poly(methacrylic acid-co-butylmethacrylate)polymer is between 50:50 and 95:5. In some embodiments, the mass ratio of methacrylic acid to butyl methacrylate in the poly(methacrylic acid-co-butylmethacrylate)polymer is between 70:30 and 95:5. In some embodiments, the mass ratio of methacrylic acid to butyl methacrylate in the poly(methacrylic acid-co-butylmethacrylate)polymer is between 80:20 and 95:5. In some embodiments, the mass ratio of methacrylic acid to butyl methacrylate in the poly(methacrylic acid-co-butylmethacrylate)polymer is between 85:15 and 95:5.

In some embodiments, the homo or co-polymer is water soluble. In some embodiments, the polymer has solubility in water above 1 weight %. In some embodiments, the polymer has solubility in water above 2 weight %. In some embodiments, the polymer has solubility in water above 3 weight %. In some embodiments, the polymer has solubility in water above 4 weight %. In some embodiments, the polymer has solubility in water above 5 weight %. In some embodiments, the polymer has solubility in water above 10 weight %. In some embodiments, the polymer has solubility in water above 20 weight %. In some embodiments, the polymer has solubility in water above 30 weight %. In some embodiments, the polymer has solubility in water between 1 and 30 weight %. In some embodiments, the polymer has solubility in water between 1 and 10 weight %. In some embodiments, the polymer has solubility in water between 5 and 10 weight %. In some embodiments, the polymer has solubility in water between 10 and 30 weight %. In some embodiments the solubility of the polymer in water can also be adjusted by adjusting pH or other solution conditions in water.

In some embodiments, the polyelectrolyte polymer has a weight average ($M_w$) molecular weight between 10,000-4,000,000 Daltons. In some embodiments, the polyelectrolyte polymer has a weight average molecular weight of 10,000-2,000,000 Daltons. In some embodiments, the polyelectrolyte polymer has a weight average molecular weight of 100,000-1,000,000 Daltons. In some embodiments, the polyelectrolyte polymer has a weight average molecular weight of 100,000-750,000 Daltons. In some embodiments, the polyelectrolyte polymer has a weight average molecular weight of 100,000-500,000 Daltons. In some embodiments, the polyelectrolyte polymer has a weight average molecular weight of 100,000-200,000 Daltons. In some embodiments, the polyelectrolyte polymer has a weight average molecular weight of 200,000-2,000,000 Daltons. In some embodiments, the polyelectrolyte polymer has a weight average molecular weight of 200,000-1,000,000 Daltons. In some embodiments, the polyelectrolyte polymer has a weight average molecular weight of 200,000-500,000 Daltons. In some embodiments, the polyelectrolyte polymer has a weight average molecular weight of 300,000-2,000,000 Daltons. In some embodiments, the polyelectrolyte polymer has a weight average molecular weight of 300,000-1,000,000 Daltons. In some embodiments, the polyelectrolyte polymer has a weight average molecular weight of 300,000-500,000 Daltons.

Nanoparticles of polymer-associated active ingredients and optionally herbicide safeners and/or aggregates of these nanoparticles can be part of a formulation in different amounts. The final amount will depend on many factors including the type of formulation (e.g., liquid or solid, granule or powder, concentrated or not, etc.). In some instances the nanoparticles (including the polymer, active ingredient, and optionally herbicide safener components) make up between about 1 and about 98 weight % of the total formulation. In some embodiments, the nanoparticles make up between 1 and 90 weight % of the total formulation. In some embodiments, the nanoparticles make up between 1 and 75 weight % of the total formulation. In some embodiments, the nanoparticles make up between 1 and 50 weight % of the total formulation. In some embodiments, the nanoparticles make up between 1 and 30 weight % of the total formulation. In some embodiments, the nanoparticles make up between 1 and 25 weight % of the total formulation. In some embodiments, the nanoparticles make up between 1 and 10 weight % of the total formulation. In some embodiments, the nanoparticles make up between 10 and 25 weight % of the total formulation. In some embodiments, the nanoparticles make up between 10 and 30 weight % of the total formulation. In some embodiments, the nanoparticles make up between 10 and 50 weight % of the total formulation. In some embodiments, the nanoparticles make up between 10 and 75 weight % of the total formulation. In some embodiments, the nanoparticles make up between 10 and 90 weight % of the total formulation. In some embodiments, the nanoparticles make up between 10 and 98 weight % of the total formulation. In some embodiments, the nanoparticles make up between 25 and 50 weight % of the total formulation. In some embodiments, the nanoparticles make up between 25 and 75 weight % of the total formulation. In some embodiments, the nanoparticles make up between 25 and 90 weight % of the total formulation. In some embodiments, the nanoparticles make up between 30 and 98 weight % of the total formulation. In some embodiments, the nanoparticles make up between 50 and 90 weight % of the total formulation. In some embodiments, the nanoparticles make up between 50 and 98 weight % of the total formulation. In some embodiments, the nanoparticles make up between 75 and 90 weight % of the total formulation. In some embodiments, the nanoparticles make up between 75 and 98 weight % of the total formulation.

In some embodiments, the nanoparticles of polymer-associated active ingredients are prepared according to a method disclosed in United States Patent Application Publication No. 20100210465, the entire contents of which are incorporated herein by reference. In some embodiments, polymer nanoparticles without active ingredients are made by collapse of a polyelectrolyte with a collapsing agent and then rendering the collapsed conformation permanent by intra-particle cross-linking. The active ingredient is then associated with this preformed polymer nanoparticle. In some embodiments, the formulation contains the same amount (by weight) of active ingredient and polymer, while in other embodiments the ratio of active ingredient to polymer (by weight) can be between 1:10 and 10:1, between 1:10 and 1:5, between 1:5 and 1:4, between 1:4 and 1:3, between 1:3 and 1:2, between 1:2 and 1:1, between 1:5 and 1:1, between 5:1 and 1:1, between 2:1 and 1:1, between 3:1 and 2:1, between 4:1 and 3:1, between 5:1 and 4:1, between 10:1 and 5:1, between 1:3 and 3:1, between 5:1 and 1:1, between 1:5 and 5:1, or between 1:2 and 2:1.

As noted above, in some embodiments, the associating step may involve dispersing the polymer nanoparticles in a first solvent, dispersing the active ingredient and optionally herbicide safener in a second solvent that is miscible or partially miscible with the first solvent, mixing the two dispersions and then either removing the second or first solvent from the final mixture. Alternatively, in some embodiments, the associating step may involve dispersing the polymer nanoparticles, active ingredient and optionally herbicide safener in a common solvent and removing all or a portion of the common solvent from the final mixture. The final form of the nanoparticles of polymer-associated active ingredient and optionally herbicide safener can be either a dispersion in a common solvent or a dried solid. The common solvent is typically one that is capable of swelling the polymer nanoparticles as well as dissolving the active ingredient and herbicide safener at a concentration of at least 10 mg/mL, e.g., at least 20 mg/mL. The polymer nanoparticles are typically dispersed in the common solvent at a concentration of at least 10 mg/mL, e.g., at least 20 mg/mL. In some embodiments, the common solvent is an alcohol (either long or short chain), preferably methanol or ethanol. In some embodiments the common solvent is selected from alkenes, alkanes, alkynes, phenols, hydrocarbons, chlorinated hydrocarbons, ketones, and ethers. In some embodiments, the common solvent is a mixture of two or more different solvents that are miscible or partially miscible with each other. Some or all of the common solvent is removed from the dispersion of polymer nanoparticles and active ingredients by either direct evaporation or evaporation under reduced pressure. The dispersion can be dried by a range of processes known by a practitioner of the art such as lyophilization (freeze-drying), spray-drying, tray-drying, evaporation, jet drying, or other methods to obtain the nanoparticles of polymers-associated with active ingredients and optionally herbicide safeners. In general, the amount of solvent that is removed from the dispersion described above will depend on the final type of formulation that is desired. This is illustrated further in the Examples and in the general description of specific formulations.

Formulating Agents

As used herein, the term "formulating agents" refers to other materials used in the formulation other than the nanoparticles of polymer-associated active ingredient and optionally herbicide safener. Formulating agents can include, but are not limited to, compounds that can act as a dispersants or wetting agents, inert fillers, solvents, surfactants, anti-freezing agents, anti-settling agents or thickeners, disintegrants, preservatives, and herbicide safeners. In some embodiments, one or more formulating agents may be present during the association step between pre-formed nanoparticles and active ingredient.

In some embodiments, a formulation may include a dispersant or wetting agent or both. In some embodiments the same compound may act as both a dispersant and a wetting agent. A dispersant is a compound that helps the nanoparticles disperse in water. Without wishing to be bound by any theory, dispersants are thought to achieve this result by absorbing on to the surface of the nanoparticles and thereby limiting re-aggregation. Wetting agents increase the spreading or penetration power of a liquid such as water onto a powder or granular formulation. Without wishing to be bound by any theory, wetting agents are thought to achieve this result by reducing the interfacial tension between the liquid and the substrate surface.

In some embodiments, a dispersant or wetting agent is selected from organosilicones (e.g., Sylgard 309 from Dow Corning Corporation or Silwet L77 from Union Carbide Corporation) including polyalkylene oxide modified polydimethylsiloxane (Silwet L7607 from Union Carbide Corporation), methylated seed oil, and ethylated seed oil (e.g., Scoil from Agsco or Hasten from Wilfarm), alkylpolyoxyethylene ethers (e.g., Activator 90), alkylarylalolates (e.g., APSA 20), alkylphenol ethoxylate and alcohol alkoxylate surfactants (e.g., products sold by Huntsman), fatty acid, fatty ester and fatty amine ethoxylates (e.g., products sold by Huntsman), products sold by Cognis such as sorbitan and ethoxylated sorbitan esters, ethoxylated vegetable oils, alkyl, glycol and glycerol esters and glycol ethers, tristyrylphenol ethoxylates, anionic surfactants such as sulphonates, such as sulphosuccinates, alkylaryl sulphonates, alkyl naphthalene sulphonates (e.g., products sold by Adjuvants Unlimited), calcium alkyl benzene sulphonates, and phosphate esters (e.g., products sold by Huntsman Chemical or BASF), as salts of sodium, potassium, ammonium, magnesium, triethanolamine (TEA), etc. Other specific examples of the above sulfates include ammonium lauryl sulfate, magnesium lauryl sulfate, sodium 2-ethyl-hexyl sulfate, sodium actyl sulfate, sodium oleyl sulfate, sodium tridecyl sulfate, triethanolamine lauryl sulfate, ammonium linear alcohol, ether sulfate ammonium nonylphenol ether sulfate, and ammonium monoxynol-4-sulfate. Other examples of dispersants and wetting agents include, sulfo succinamates, disodium N-octadecylsulfo-succinamate; tetrasodium N-(1, 2-dicarboxyethyl)-N-octadecylsulfo-succinamate; diamyl ester of sodium sulfosuccinic acid; dihexyl ester of sodium sulfosuccinic acid; and dioctyl esters of sodium sulfosuccinic acid; dihexyl ester of sodium sulfosuccinic acid; and dioctyl esters of sodium sulfosuccinic acid; castor oil and fatty amine ethoxylates, including sodium, potassium, magnesium or ammonium salts thereof. Dispersants and wetting agents also include natural emulsifiers, such as lecithin, fatty acids (including sodium, potassium or ammonium salts thereof) and ethanolamides and glycerides of fatty acids, such as coconut diethanolamide and coconut mono- and diglycerides. Dispersants and wetting agents also include sodium polycarboxylate; sodium salt of naphthalene sulfonate condensate; sodium lignosulfonates; aliphatic alcohol ethoxylates; tristyrylphenol ethoxylates and esters; ethylene oxide-propylene oxide block copolymers. Examples of dispersants and wetting agents include, but are not limited to, sodium dodecylbenzene sulfonate; N-oleyl N-methyl taurate; 1,4-dioctoxy-1,4-dioxo-butane-2-sulfonic acid; sodium lauryl sulphate; sodium dioctyl sulphosuccinate; aliphatic alcohol ethoxylates; nonylphenol ethoxylates. Dispersants and wetting agents also include sodium taurates; and sodium or ammonium salts of maleic anhydride copolymers, lignosulfonic acid formulations or condensed sulfonate sodium, potassium, magnesium or ammonium salts, polyvinylpyrrolidone (available commercially as Polyplasdone XL-10 from International Specialty Products or as Kollidon C1 M-10 from BASF Corporation), polyvinyl alcohols, modified or unmodified starches, methylcellulose, hydroxyethyl or hydroxypropyl methylcellulose, carboxymethyl methylcellulose, or combinations, such as a mixture of either lignosulfonic acid formulations or condensed sulfonate sodium, potassium, magnesium or ammonium salts with polyvinylpyrrolidone (PVP).

In some embodiments, the dispersants and wetting agents can combine to make up between about 1 and about 30 weight % of the formulation. For example, dispersants and wetting agents can make up between about 1 and about 20 weight %, about 1 and about 10 weight %, between about 1 and about 5 weight %, between about 1 and about 3 weight %, between about 2 and about 30 weight %, between about 2 and about 20 weight %, between about 2 and about 10 weight %, between about 3 and about 30 weight %, between about 3 and about 20 weight %, between about 3 and about 10 weight %, between about 3 and about 5 weight %, between about 5 and about 30 weight %, between about 5 and about 20 weight %, between about 5 and about 10 weight % of the formulation. In some embodiments, dispersants or wetting agents can make up between about 0.1 and 1 weight % of the formulation.

In some embodiments, a formulation may include an inert filler. For example, an inert filler may be included to produce or promote cohesion in forming a wettable granule formulation. An inert filler may also be included to give the formulation a certain active loading, density, or other similar physical properties. Non limiting examples of inert fillers that may be used in a formulation include bentonite clay, carbohydrates, proteins, lipids synthetic polymers, glycolipids, glycoproteins, lipoproteins, lignin, lignin derivatives, and combinations thereof. In a preferred embodiment the inert filler is a lignin derivative and is optionally calcium lignosulfonate. In some embodiments, the inert filler is selected from the group consisting of: monosaccharides, disaccharides, oligosaccharides, polysaccharides and combinations thereof. Specific carbohydrate inert fillers illustratively include glucose, mannose, fructose, galactose, sucrose, lactose, maltose, xylose, arabinose, trehalose and mixtures thereof such as corn syrup; celluloses such as carboxymethylcellulose, ethylcellulose, hydroxyethylcellulose, hydroxy-methylethylcellulose, hydroxyethylpropylcellulose, methylhydroxyethylcellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; vegetable oils such as corn, soybean, peanut, canola, olive and cotton seed; complex organic substances such as lignin and nitrolignin; derivatives of lignin such as lignosulfonate salts illustratively including calcium lignosulfonate and sodium lignosulfonate and complex carbohydrate-based formulations containing organic and inorganic ingredients such as molasses. Suitable protein inert fillers illustratively include soy extract, zein, protamine, collagen, and casein. Inert fillers operative herein also include synthetic organic polymers capable of promoting or producing cohesion of particle components and such inert fillers illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex.

In some embodiments, a formulation contains between about 1 and about 90 weight % inert filler, e.g., between 1-80 weight %, between 1-60 weight %, between 1-40 weight %, between 1-25 weight %, between 1-10 weight %, between 10-90 weight %, between 10-80 weight %, between 10-60 weight %, between 10-40 weight %, between 10-25 weight %, between 25-90 weight %, between 25-80 weight %, between 25-60 weight %, between 25-40 weight %, between 40-90 weight %, between 40-80 weight %, or between 60-90 weight %.

In some embodiments, a formulation may include a solvent or a mixture of solvents that can be used to assist in controlling the solubility of the active ingredient itself, the nanoparticles of polymer-associated active ingredients, or other components of the formulation. For example, the solvent can be chosen from water, alcohols, alkenes, alkanes, alkynes, phenols, hydrocarbons, chlorinated hydrocarbons, ketones, ethers, and mixtures thereof. In some embodiments, the formulation contains a solvent or a mixture of solvents that makes up about 0.1 to about 90 weight % of the formulation. In some embodiments, a formulation contains between about 0.1 and about 90 weight % solvent, e.g., between 1-80 weight %, between 1-60 weight %, between 1-40 weight %, between 1-25 weight %, between 1-10 weight %, between 10-90 weight %, between 10-80 weight %, between 10-60 weight %, between 10-40 weight %, between 10-25 weight %, between 25-90 weight %, between 25-80 weight %, between 25-60 weight %, between 25-40 weight %, between 40-90 weight %, between 40-80 weight %, or between 60-90 weight %, 0.1-10 weight %, 0.1-5 weight %, 0.1-3 weight %, 0.1-1 weight %, 0.5-20 weight %, 0.5-10 weight %, 0.5-5 weight %, 0.5-3 weight %, 0.5-1 weight %, 1-20 weight %, 1-10 weight %, 1-5 weight %, 1-3 weight %, 5-20 weight %, 5-10 weight %, 10-20 weight %.

In some embodiments, a formulation may include a surfactant. When included in formulations, surfactants can function as wetting agents, dispersants, emulsifying agents, solubilizing agents and bioenhancing agents. Without limitation, particular surfactants may be anionic surfactants, cationic surfactants, nonionic surfactants, amphoteric surfactants, silicone surfactants, and fluorosurfactants. Exemplary anionic surfactants include alkylbenzene sulfonates, alkyl sulfonates and ethoxylates, sulfosuccinates, phosphate esters, taurates, alkylnaphthalene sulfonates and polymers lignosulfonates. Exemplary nonionic surfactants include alkylphenol ethoxylates, aliphatic alcohol ethoxylates, aliphatic alkylamine ethoxylates, sorbitan esters and their ethoxylates, castor oil ethoxylates, ethylene oxide/propylene oxide copolymers and polymeric surfactants. In some embodiments, surfactants can make up between about 1 about 20 weight % of the formulation, e.g., 1-15 weight %, 1-10 weight %, 1-8 weight %, 1-6 weight %, 1-4 weight %, 3-20 weight %, 3-15 weight %, 3-10 weight %, 3-8 weight %, 3-6 weight %, 5-15 weight %, 5-10 weight %, 5-8 weight %, or 10-15 weight %. In some embodiments, a surfactant (e.g., a non-ionic surfactant) may be added to a formulation by the end user, e.g., in a spray tank. Indeed, when a formulation is added to the spray tank it becomes diluted and, in some embodiments, it may be advantageous to add additional surfactant in order to maintain the nanoparticles in dispersed form.

In some embodiments, a formulation may include an anti-settling agent or thickener that can help provide stability to a liquid formulation or modify the rheology of the formulation. Examples of anti-settling agents or thickeners include, but are not limited to, guar gum; locust bean gum; xanthan gum; carrageenan; alginates; methyl cellulose; sodium carboxymethyl cellulose; hydroxyethyl cellulose; modified starches; polysaccharides and other modified polysaccharides; polyvinyl alcohol; glycerol alkyd resins such as Latron B-1956 from Rohm & Haas Co., plant oil based materials (cocodithalymide) with emulsifiers; polymeric terpenes; microcrystalline cellulose; methacrylates; poly(vinylpyrrolidone), syrups, and polyethylene oxide. In some embodiments, anti-settling agents or thickeners can make up between about 0.05 and about 5 weight % of the formulation, e.g., 0.05 to 3 weight %, 0.05 to 1 weight %, 0.05 to 0.5 weight %, 0.05 to 0.1 weight %, 0.1 to 5 weight %, 0.1 to 3 weight %, 0.1 to 1 weight %, 0.1 to 0.5 weight %, 0.5 to 5 weight %, 0.5 to 3 weight %, 0.5 to 1 weight %, 1 to 5 weight %, or 1 to 3 weight %. In some embodiments, it is explicitly contemplated that a formulation of the present invention does not include a compound whose primary function is to act as an anti-settling or thickener. In some embodiments, compounds included in a formulation may have some anti-settling or thickening functionality, in addition to other, primary functionality, so anti-settling or thickening functionality is not a necessary condition for exclusion, however, formulation agents used primarily or exclusively as anti-settling agents or thickeners may be expressly omitted from the formulations.

In some embodiments, a formulation may include one or more preservatives that prevent microbial or fungal degradation of the product during storage. Examples of preservatives include but are not limited to, tocopherol, ascorbyl palmitate, propyl gallate, butylated hydroxyanisole (BHA), butylated hydroxytoluene (BHT), propionic acid and its sodium salt; sorbic acid and its sodium or potassium salts; benzoic acid and its sodium salt; p-hydroxy benzoic acid sodium salt; methyl p-hydroxy benzoate; 1,2-benzisothiazalin-3-one, and combinations thereof. In some embodiments, preservatives can make up about 0.01 to about 0.2 weight % of the formulation, e.g., 0.01-0.1 weight %, 0.01-0.05 weight %, 0.01-0.02 weight %, 0.02-0.2 weight %, 0.02-0.1 weight %, 0.02-0.05 weight %, 0.05-0.2 weight %, 0.05-0.1 weight %, or 0.1-0.2 weight %.

In some embodiments, a formulation may include anti-freezing agents, anti-foaming agents, and/or anti-caking agents that help stabilize the formulation against freezing during storage, foaming during use, or caking during storage. Examples of anti-freezing agents include, but are not limited to, ethylene glycol, propylene glycol, and urea. In certain embodiment a formulation may include between about 0.5 and about 10 weight % anti-freezing agents, e.g., 0.5-5 weight %, 0.5-3 weight %, 0.5-2 weight %, 0.5-1 weight %, 1-10 weight %, 1-5 weight %, 1-3 weight %, 1-2 weight %, 2-10 weight %, 3-10 weight %, or 5-10 weight %. Examples of anti-foaming agents include, but are not limited to, silicone based anti-foaming agents (aqueous emulsions of dimethyl polysiloxane), and non-silicone based anti-foaming agents such as octanol, nonanol, and silica. In some embodiments a formulation may include between about 0.05 and about 5 weight % of anti-foaming agents, e.g., 0.05-0.5 weight %, 0.05-1 weight %, 0.05-0.2 weight %, 0.1-0.2 weight %, 0.1-0.5 weight %, 0.1-1 weight %, or 0.2-1 weight %. Examples of anti-caking agents include sodium or ammonium phosphates, sodium carbonate or bicarbonate, sodium acetate, sodium metasilicate, magnesium or zinc sulfates, magnesium hydroxide (all optionally as hydrates), sodium alkylsulfosuccinates, silicious compounds, magnesium compounds, C10-C22 fatty acid polyvalent metal salt compounds, and the like. Illustrative of anti-caking ingredients are attapulgite clay, kieselguhr, silica aerogel, silica xerogel, perlite, talc, vermiculite, sodium aluminosilicate, zirconium oxychloride, starch, sodium or potassium phthalate, calcium silicate, calcium phosphate, calcium nitride, aluminum nitride, copper oxide, magnesium carbonate, magnesium silicate, magnesium nitride, magnesium phosphate, magnesium oxide, magnesium nitrate, magnesium sulfate, magnesium chloride, and the magnesium and aluminum salts of C10-C22 fatty acids such as palmitic acid, stearic acid and oleic acid. Anti-caking agents also include refined kaolin clay, amorphous precipitated silica dioxide, such as Hi Sil 233 available from PPG Industries, or refined clay, such as Hubersil available from Huber Chemical Company. In some embodiments, a formulation may include between about 0.05 and about 5 weight % anti-caking agents, e.g., 0.05-3 weight %, 0.05-2 weight %, 0.05-1 weight %, 0.05-0.5 weight %, 0.05-0.1 weight %, 0.1-5 weight %, 0.1-3 weight %, 0.1-2 weight %, 0.1-1 weight %, 0.1-0.5 weight %, 0.5-5 weight %, 0.5-3 weight %, 0.5-2 weight %, 0.5-1 weight %, or 1-5 weight %.

In some embodiments, a formulation may include a UV-blocking compound that can help protect the active ingredient from degradation due to UV irradiation. Examples of UV-blocking compounds include ingredients commonly found in sunscreens such as benzophenones, benzotriazoles, homosalates, alkyl cinnamates, salicylates such as octyl salicylate, dibenzoylmethanes, anthranilates, methylbenzylidenes, octyl triazones, 2-phenylbenzimidazole-5-sulfonic acid, octocrylene, triazines, cinnamates, cyanoacrylates, dicyano ethylenes, etocrilene, drometrizole trisiloxane, bisethylhexyloxyphenol methoxyphenol triazine, drometrizole, dioctyl butamido triazone, terephthalylidene dicamphor sulfonic acid and para-aminobenzoates as well as ester derivatives thereof, UV-absorbing metal oxides such as titanium dioxide, zinc oxide, and cerium oxide, and nickel organic compounds such as nickel bis (octylphenol) sulfide, etc. Additional examples of each of these classes of UV-blockers may be found in Kirk-Othmer, Encyclopedia of Chemical Technology. In some embodiments, a formulation may include between about 0.01 and about 2 weight % UV-blockers, e.g., 0.01-1 weight %, 0.01-0.5 weight %, 0.01-0.2 weight %, 0.01-0.1 weight %, 0.01-0.05 weight %, 0.05 weight %-1 weight %, 0.05-0.5 weight %, 0.05-0.2 weight %, 0.05-0.1 weight %, 0.1-1 weight %, 0.1-0.5 weight %, 0.1-0.2 weight %, 0.2-1 weight %, 0.2-0.5 weight %, or 0.5-1 weight %. In some embodiments, it is explicitly contemplated that a formulation of the present invention does not include a compound whose primary function is to act as a UV-blocker. In some embodiments, compounds included in a formulation may have some UV-blocking functionality, in addition to other, primary functionality, so UV-blocking is not a necessary condition for exclusion, however, formulation agents used primarily or exclusively as UV-blockers may be expressly omitted from the formulations.

In some embodiments, a formulation may include a disintegrant that can help a solid formulation break apart when added to water. Examples of suitable disintegrants include cross-linked polyvinyl pyrrolidone, modified cellulose gum, pregelatinized starch, cornstarch, modified corn starch (e.g., Starch 1500) and sodium carboxymethyl starch (e.g., Explotab or Primojel), microcrystalline cellulose, sodium starch glycolate, sodium carboxymethyl cellulose, carmellose, carmellose calcium, carmellose sodium, croscarmellose sodium, carmellose calcium, carboxymethylstarch sodium, low-substituted hydroxypropyl cellulose, hydroxypropyl methylcellulose, hydroxypropyl cellulose, soy polysaccharides (e.g., EMCOSOY), alkylcelullose, hydroxyalkylcellulose, alginates (e.g., Satialgine), dextrans and poly(alkylene oxide) and an effervescent couple (citric or ascorbic acid plus bicarbonate), lactose, anhydrous dibasic calcium phosphate, dibasic calcium phosphate, magnesium aluminometasilicate, synthesized hydrotalcite, silicic anhydride and synthesized aluminum silicate. In some embodiments disintegrants can make up between about 1 about 20 weight % of the formulation, e.g., 1-15 weight %, 1-10 weight %, 1-8 weight %, 1-6 weight %, 1-4 weight %, 3-20 weight %, 3-15 weight %, 3-10 weight %, 3-8 weight %, 3-6 weight %, 5-15 weight %, 5-10 weight %, 5-8 weight %, or 10-15 weight %.

In some embodiments, a formulation may include herbicide safener. As mentioned above, herbicide safeners reduce or eliminate the phytotoxic effects of the active ingredient against non-target plant species (eg. crops), while maintaining acceptable levels of efficacy against target species (e.g. weeds). As discussed previously, in some embodiments, active ingredient and herbicide safener are associated with pre-formed nanoparticles, thereby providing nanoparticles of active ingredients and herbicide safeners. As described above, in some embodiments, the herbicide safener may be present during the association step between pre-formed nanoparticles and active ingredient. In some embodiments, the formulation includes a herbicide safener that is not present during the association between pre-formed nanoparticles and active ingredient. Examples of herbicide safeners include, but are not limited to any of the aforementioned herbicide safeners listed above in the section titled Herbicide Safeners. In some embodiments, a herbicide safener may be added to a formulation by the end user, e.g., in a spray tank.

As described above, the ratio of active ingredient to herbicide safener can vary widely depending on the characteristics of the active ingredient, the safener, formulation, and particular application. In some embodiments, the ratio of active ingredient to herbicide safener (by weight) can be between 100:1 and 1:100, 100:1 and 1:50, 100:1 and 1:20, 100:1 and 1:10, 100:1 and 1:1, 100:1 and 100:10, 50:1 and 1:100, 20:1 and 1:100, 10:1 and 1:100, 1:1 and 1:100, or 1:10 and 1:100. In some embodiments, the ratio of active ingredient to herbicide safener (by weight) can be between 50:1 and 1:50, 50:1 and 1:20, 50:1 and 1:10, 50:1 and 1:1, 20:1 and 1:50, 10:1 and 1:50, or 1:1 and 1:50. In some embodiments, the ratio of active ingredient to herbicide safener (by weight) can be between 20:1 and 1:20, 20:1 and 1:10, 20:1 and 1:1, 10:1 and 1:20, 1:1 and 1:20, 10:1 and 1:10, 10:1 and 1:1, 1:1 and 1:10, or 5:1 and 1:5.

In some embodiments herbicide safeners can make up between about 0.001 to about 90 weight % of the formulation, e.g. between about 0.001 and about 90 weight %, about 0.001 and about 60 weight %, about 0.001 and about 40 weight %, about 0.001 and about 25 weight %, about 0.001 and about 10 weight %, about 0.01 and about 90 weight %, about 0.01 and about 60 weight %, about 0.01 and about 40 weight % about 0.01 and about 25 weight %, about 0.01 and about 10 weight %, about 0.1 and about 90 weight %, about 0.1 and about 60 weight %, about 0.1 and about 40 weight %, about 0.1 and about 25 weight %, about 0.1 and about 10 weight %, about 1 and about 90 weight %, about 1 and about 60 weight %, about 1 and about 40 weight %, about 1 and about 30 weight %, about 1 and about 20 weight %, about 1 and about 10 weight %, about 1 and about 5 weight %, about 5 and about 90 weight %, about 5 and about 60 weight %, about 5 and about 50 weight %, about 5 and about 40 weight %, about 5 and about 30 weight %, about 5 and about 20 weight %, about 5 and about 15 weight %, about 10 and about 90 weight %, about 10 and about 60 weight %, about 10 and about 40 weight %, about 10 and about 25 weight %, about 20 and about 90 weight %, about 20 and about 60 weight %.

Formulations

As described above, the nanoparticles of polymer-associated active ingredient can be formulated into different types of formulations for different applications. For example, the types of formulations can include wettable granules, wettable powders, and high solid liquid suspensions. Furthermore, as discussed above, formulation agents can include, but are not limited to dispersants, wetting agents, surfactants, anti-settling agents or thickeners, preservatives, anti-freezing agents, anti-foaming agents, anti-caking agents, inert fillers, and UV-blockers, and herbicide safeners.

In some embodiments, a dispersion of polymer nanoparticles and active ingredient in a common solvent is dried (e.g., spray dried) to form a solid containing nanoparticles (optionally in aggregate form) of polymer-associated active ingredients. The spray dried solid can then be used as is or incorporated into a formulation containing other formulating agents to make a wettable granule (WG), wettable powder (WP), or a high solids liquid suspension (HSLS). In some embodiments, the drying step may be performed in the presence of one or more formulating agents.

In some embodiments, active ingredient is milled in the presence of pre-formed polymer nanoparticles to form a solid containing nanoparticles (optionally in aggregate form) of polymer-associated active ingredients. The solid can then be used as is or incorporated into a formulation containing other formulating agents to make a wettable granule (WG), wettable powder (WP), or a high solids liquid suspension (HSLS). In some embodiments, the milling step may be performed in the presence of one or more formulating agents. In some embodiments, the milling step may be performed in the presence of an aqueous phase.

In some embodiments, a dispersion of polymer nanoparticles, active ingredient and herbicide safener in a common solvent is dried (e.g., spray dried) to form a solid containing nanoparticles (optionally in aggregate form) of polymer-associated active ingredients and herbicide safener. The spray dried solid can then be used as is or incorporated into a formulation containing other formulating agents to make a wettable granule (WG), wettable powder (WP), or a high solids liquid suspension (HSLS). In some embodiments, the drying step may be performed in the presence of one or more formulating agents.

In some embodiments, a dispersion polymer nanoparticles in a first solvent, and a solution or dispersion of active ingredient and optionally herbicide safener in a second solvent, which may be the same or different from the first solvent and which is miscible with the first solvent, are mixed and dried (e.g., spray dried) to form a solid containing nanoparticles (optionally in aggregate form) of polymer-associated active ingredients and optionally herbicide safeners. The spray dried solid can then be used as is or incorporated into a formulation containing other formulating agents to make a water dispersible granule (WG), wettable powder (WP), or a high solids liquid suspension (HSLS). In some embodiments, the drying step may be performed in the presence of one or more formulating agents.

In some embodiments the active ingredient and herbicide safener are milled in the presence of pre-formed polymer nanoparticles to form a solid containing nanoparticles (optionally in aggregate form) of polymer-associated active ingredients and herbicide safener. The solid can then be used as is or incorporated into a formulation containing other formulating agents to make a wettable granule (WG), wettable powder (WP), or a high solids liquid suspension (HSLS). In some embodiments, the milling step may be performed in the presence of one or more formulating agents. In some embodiments, the milling step may be performed in the presence of an aqueous phase.

Wettable Granules (WG)

In some embodiments, the dried solid can be made into a formulation that is a wettable granule (WG) by adding other formulating agents and by extruding the formulation to form granules. In some embodiments, a WG formulation may be made by mixing together a dried (e.g., spray-dried, freeze dried, etc.) or milled solid comprising nanoparticles of polymer-associated active ingredient and optionally herbicide safener, or (aggregates thereof), a wetting agent (e.g., a surfactant such as sodium dodecylbenzene sulfonate) and/or a dispersant (e.g., a lignosulfonate such as Reax 88B, etc.) and an inert filler (e.g., lactose). In some embodiments a WG can be made using a wetting agent (e.g., a surfactant such as sodium dodecylbenzene sulfonate) and a dispersant (e.g., a lignosulfonate such as Reax 88B, etc.).

In some embodiments, the components of the WG formulation are all mixed in a vessel, moistened with about 30 to about 50% equivalent mass of water, and the resulting semi-solid is extruded to make granules. In some embodiments, the formulation of the final WG can be (by weight): 0-5% dispersant, 0-5% wetting agent, 5-80% nanoparticles of polymer-associated active ingredient and optionally a herbicide safener (optionally in aggregate form), and inert filler to 100%. In some embodiments, the formulation of the final WG can be (by weight): 0.5-5% dispersant, 0.5%-5% wetting agent, 5-80% nanoparticles of polymer-associated active ingredient and optionally herbicide safener, and inert filler to 100%.

In some embodiments, a WG formulation comprising nanoparticles of polymer-associated active ingredients (optionally in aggregate form) may be made by using a dispersion of polymer nanoparticles and active ingredient and optionally a herbicide safener in a common solvent, preferably methanol. In some embodiments, a WG formulation can be made by adding the dispersion in common solvent into an aqueous solution containing a wetting agent (e.g., a surfactant such as sodium dodecylbenzene sulfonate) and/or a dispersant (e.g., a lignosulfonate such as Reax 88B, etc.) and an inert filler (e.g., lactose), and optionally a herbicide safener, drying (freeze drying, spray drying, etc.) the resulting mixture to from a solid and then granulating the solid to obtain a WG formulation comprising nanoparticles of polymer-associated active ingredients (optionally in aggregate form). In some embodiments a WG can be made using a wetting agent (e.g., a surfactant such as sodium dodecylbenzene sulfonate) and a dispersant (e.g., a lignosulfonate such as Reax 88B, etc.).

In some embodiments, the polymer nanoparticles are made from a co-polymer of methacrylic acid and ethyl acrylate at a 90:10 mass ratio. In some embodiments, the polymer nanoparticles are made from a co-polymer of methacrylic acid and ethyl acrylate at a 75:25 mass ratio. In some embodiments, the polymer nanoparticles are made from a co-polymer of methacrylic acid and styrene at a 90:10 mass ratio. In some embodiments, the polymer nanoparticles are made from a co-polymer of methacrylic acid and styrene at a 75:25 mass ratio. In some embodiments, the polymer nanoparticles are made from a co-polymer of methacrylic acid and butylmethacrylate at a 75:25 mass ratio. In some embodiments, the polymer nanoparticles are dispersed in a common solvent, in some cases at a concentration of 20 mg/mL or higher.

In some embodiments, the active ingredient is selected from Aryloxyphenoxypropionate herbicides, cyclohexanedione herbicides, sulfonylurea herbicides, sulfonamide herbicides, triazolinones and triazolinone inhibitors of PPO. In some embodiments, the active ingredient is fenoxaprop-P-ethyl. In some embodiments, the active ingredient is mixed with the nanoparticle dispersion at a concentration of 20 mg/mL or higher. In some embodiments, the ratio of active ingredient to polymer nanoparticle is 1:1, 2:1, 3:1, 4:1 or 5:1, a range between these values or another range as listed above.

In some embodiments, the dispersion of polymer nanoparticles, active ingredient, and optionally an herbicide safener in a common solvent is slowly added to a vessel containing a second solvent, preferably water. In some embodiments, the second solvent is at least 20 times larger in volume than the common solvent containing the polymer nanoparticles and active ingredient. In some embodiments, the second solvent contains a dispersant, preferably but not limited to a lignosulfonate such as Reax 88B and/or a wetting agent, preferably but not limited to a surfactant such as sodium dodecylbenzene sulfonate and an inert filler, preferably but not limited to lactose, and optionally an herbicide safener. In some embodiments a WG can be made using a wetting agent (e.g., a surfactant such as sodium dodecylbenzene sulfonate) and a dispersant (e.g., a lignosulfonate such as Reax 88B, etc.).

In some embodiments, after the dispersion in a common solvent is mixed with the second solvent the solvents are removed by drying. In some embodiments, the solvents are removed by freeze drying. In some embodiments, the solvents are removed by spray drying. The resulting solid formulation is then moistened with about 30 to about 50% equivalent mass of water and is then extruded to form granules. In some embodiments, the granules are formed by hypodermic syringe extrusion. In some embodiments, the granules are formed through extrusion granulation, pan granulation, fluid bed granulation, spray drying granulation, or high shear granulation.

In some embodiments, the granules disperse in solution in 30 seconds or less. In some case the WG formulation has low friability. In some embodiments, the WG formulation has low dustiness. In some embodiments, when the WG formulation is dispersed in water, the dispersion results in particles with an average size within about 100 nm to about 200 nm, or in some cases, within about 100 nm to about 150 nm. In some embodiments, a dispersion of the WG formulation in water creates minimal foam. In some embodiments, the WG formulation containing fenoxaprop-P-ethyl has minimal skin irritating effects. In some embodiments, the WG formulation is stable after 1-2 months of continuous temperature cycling between −5° C. and 45° C.

Wettable Powder (WP)

In some embodiments, the dried solid can be made into a formulation that is a wettable powder (WP). In some embodiments, a WP formulation comprising nanoparticles of polymer-associated active ingredients (optionally in aggregate form) can be made from a dried (e.g., spray dried, freeze dried, etc.) dispersion of polymer nanoparticles and active ingredient. In some embodiments, a WP formulation comprising nanoparticles of polymer-associated active ingredients (optionally in aggregate form) can be made from a milled solid comprising polymer nanoparticles of active ingredient. In some embodiments, a WP is made by mixing the dried solid or milled solid with a dispersant and/or a wetting agent. In some embodiments, a WP is made by mixing the dried or milled solid with a dispersant and a wetting agent. In some embodiments, the formulation of the final WP can be (by weight): up to about 98% nanoparticles of polymer-associated active ingredients (including both the active ingredient and the polymer, optionally in aggregate form). In some embodiments, the WP formulation includes (by weight): 0-5% dispersant, 0-5% wetting agent, 5-98% nanoparticles of polymer-associated active ingredients (optionally in aggregate form), and inert filler to 100%. In some embodiments, the formulation of the final WP can be (by weight): 0.5-5% dispersant, 0.5%-5% wetting agent, 5-98% nanoparticles of polymer-associated active ingredients (optionally in aggregate form), and inert filler to 100%.

In some embodiments, a WP formulation comprising nanoparticles of polymer-associated active ingredients and herbicide safeners (optionally in aggregate form) can be made from a dried (e.g., spray dried, freeze dried, etc.) dispersion of polymer nanoparticles of active ingredient and herbicide safener. In some embodiments, a WP formulation comprising nanoparticles of polymer-associated active ingredients (optionally in aggregate form) can be made from a milled solid comprising polymer nanoparticles of active ingredient and herbicide safener. In some embodiments, a WP is made by mixing the dried or milled solid with a dispersant and/or a wetting agent. In some embodiments, a WP is made by mixing the dried or milled solid with a dispersant and a wetting agent. In some embodiments, the formulation of the final WP can be (by weight): up to about 98% nanoparticles of polymer-associated active ingredients and herbicide safeners (including the active ingredient, herbicide safener, and the polymer, optionally in aggregate form). In some embodiments, the WP formulation includes (by weight): 0-5% dispersant, 0-5% wetting agent, 5-98% nanoparticles of polymer-associated active ingredients and herbicide safener (optionally in aggregate form), and inert filler to 100%. In some embodiments, the formulation of the final WP can be (by weight): 0.5-5% dispersant, 0.5%-5% wetting agent, 5-98% nanoparticles of polymer-associated active ingredients and herbicide safener (optionally in aggregate form), and inert filler to 100%.

In some embodiments, a WP formulation comprising nanoparticles of polymer-associated active ingredients (optionally in aggregate form) may be made from a dispersion of polymer nanoparticles and active ingredient in a common solvent, preferably methanol. In some embodiments, a WP formulation can be made by adding the dispersion in common solvent into an aqueous solution containing a wetting agent (e.g., a surfactant such as sodium dodecylbenzene sulfonate) and/or a dispersant (e.g., a lignosulfonate such as Reax 88B, etc.) and optionally an inert filler (e.g., lactose), and then drying (e.g., freeze drying, spray drying, etc.) the resulting mixture to from a solid powder. In some embodiments a WP can be made using a wetting agent (e.g., a surfactant such as sodium dodecylbenzene sulfonate) and a dispersant (e.g., a lignosulfonate such as Reax 88B, etc.).

In some embodiments, a WP formulation comprising nanoparticles of polymer-associated active ingredients and herbicide safeners (optionally in aggregate form) may be made from a dispersion of polymer nanoparticles, active ingredient and herbicide safener in a common solvent, preferably methanol. In some embodiments, a WP formulation can be made by adding the dispersion in common solvent into an aqueous solution containing a wetting agent (e.g., a surfactant such as sodium dodecylbenzene sulfonate) and/or a dispersant (e.g., a lignosulfonate such as Reax 88B, etc.) and optionally an inert filler (e.g., lactose), and then drying (e.g., freeze drying, spray drying, etc.) the resulting mixture to from a solid powder. In some embodiments a WP can be made using a wetting agent (e.g., a surfactant such as sodium dodecylbenzene sulfonate) and a dispersant (e.g., a lignosulfonate such as Reax 88B, etc.).

In some embodiments, the polymer nanoparticles are made from a co-polymer of methacrylic acid and ethyl acrylate at a 90:10 mass ratio. In some embodiments, the polymer nanoparticles are made from a co-polymer of methacrylic acid and ethyl acrylate at a 75:25 mass ratio. In some embodiments, the polymer nanoparticles are made from a co-polymer of methacrylic acid and styrene at a 90:10 mass ratio. In some embodiments, the polymer nanoparticles are made from a co-polymer of methacrylic acid and styrene at a 75:25 mass ratio. In some embodiments, the polymer nanoparticles are made from a co-polymer of methacrylic acid and butylmethacrylate at a 75:25 mass ratio. In some embodiments, the polymer nanoparticles are dispersed in a common solvent, in some cases at a concentration of 20 mg/mL or higher.

In some embodiments, the active ingredient is selected from Aryloxyphenoxypropionate herbicides, cyclohexanedione herbicides, sulfonylurea herbicides, sulfonamide herbicides, triazolinones and triazolinone inhibitors of PPO. In some embodiments, the active ingredient is fenoxaprop-P-ethyl. In some embodiments, the active ingredient is mixed into the polymer nanoparticle dispersion at a concentration of 20 mg/mL.

In some embodiments, the dispersion of polymer nanoparticles and active ingredient and optionally herbicide safener is then slowly added into a vessel containing a second solvent, preferably water. In some embodiments, the second solvent is at least 20 times larger in volume than the common solvent containing the polymer nanoparticles and active ingredient. In some embodiments, the second solvent contains a dispersant, preferably a lignosulfonate such as Reax 88B and/or a wetting agent, preferably a surfactant such as sodium dodecylbenzene sulfonate. In some embodiments a WP can be made using a wetting agent (e.g., a surfactant such as sodium dodecylbenzene sulfonate) and a dispersant (e.g., a lignosulfonate such as Reax 88B, etc.).

In some embodiments, after the dispersion of polymer nanoparticles and active ingredient and optionally herbicide safener in a common solvent is mixed with a second solvent containing dispersant and/or wetting agent, the final mixture is dried (e.g., freeze dried) to obtain a solid powdered formulation containing nanoparticles of polymer-associated active ingredients (optionally in aggregate form).

High Solids Liquid Suspension (HSLS)

In some embodiments, a HSLS comprising nanoparticles of polymer-associated active ingredient (optionally in aggregate form) can be made from a dispersion of polymer nanoparticles and active ingredient in a common solvent or from a dried form of the dispersion (e.g., spray dried). In some embodiments, a HSLS formulation comprising nanoparticles of polymer-associated active ingredients (optionally in aggregate form) can be made from a milled solid comprising polymer nanoparticles of active ingredient.

In some embodiments, a HSLS is made by mixing the dried dispersion of polymer-associated active ingredient (e.g., spray dried) with a wetting agent, preferably a surfactant such as sodium dodecylbenzene sulfonate, a solvent, preferably but not limited to water, and/or a dispersant, preferably, but not limited to a lignosulfonate such as Reax 88B, and an anti-freezing agent, preferably but not limited to ethylene glycol, in a high sheer mixer until a stable HSLS is obtained. In some embodiments a wetting agent, preferably a surfactant such as sodium dodecylbenzene sulfonate, a solvent, preferably but not limited to water, and a dispersant, preferably, but not limited to a lignosulfonate such as Reax 88B are included. In some embodiments, a preservative, preferably propionic acid and an anti-settling agent or thickener, preferably but not limited to a water dispersible agent like xanthan gum, are also included. In some embodiments, a herbicide safener is included.

In some embodiments, the formulation of the HSLS can be (by weight): 5-80% nanoparticles of polymer-associated active ingredients (including both polymer and active ingredient optionally in aggregate form), 0.5-5% wetting agent and/or dispersant, 1-10% anti-freezing agent, 0.2-2% anti-settling agent or thickener, 0.01-0.1% preservative, and water up to 100%.

In some embodiments, a HSLS is made by reconstituting the dried dispersion (e.g., freeze dried) of nanoparticles of polymer-associated active ingredients in water to obtain a formulation that is more than 60% solids by weight and then adding an anti-freezing agent (and optionally a thickening agent and a preservative) to the final mixture. In some embodiments, a HSLS is made by reconstituting the milled (e.g. ball-milled) solid of nanoparticles of polymer-associated active ingredients in water to obtain a formulation that is more than 60% solids by weight and then adding an anti-freezing agent (and optionally a thickening agent and a preservative) to the final mixture. In some embodiments, the HSLS is made by homogenizing all the components together. In some embodiments the HSLS is made by milling all the components together.

In some embodiments, a HSLS comprising nanoparticles of polymer-associated active ingredient and herbicide safener (optionally in aggregate form) can be made from a dispersion of polymer nanoparticles, active ingredient and herbicide safener in a common solvent or from a dried form of the dispersion (e.g., spray dried). In some embodiments, a HSLS formulation comprising nanoparticles of polymer-associated active ingredients and herbicide safener (optionally in aggregate form) can be made from a milled solid comprising polymer nanoparticles of active ingredient and herbicide safener.

In some embodiments, a HSLS is made by mixing the dried dispersion of polymer-associated active ingredient and herbicide safener (e.g., spray dried) with a wetting agent, preferably a surfactant such as sodium dodecylbenzene sulfonate, a solvent, preferably but not limited to water, and/or a dispersant, preferably, but not limited to a lignosulfonate such as Reax 88B, and an anti-freezing agent, preferably but not limited to ethylene glycol, in a high sheer mixer until a stable HSLS is obtained. In some embodiments a wetting agent, preferably a surfactant such as sodium dodecylbenzene sulfonate, a solvent, preferably but not limited to water, and a dispersant, preferably, but not limited to a lignosulfonate such as Reax 88B are included. In some embodiments, a preservative, preferably propionic acid and an anti-settling agent or thickener, preferably but not limited to a water dispersible agent like xanthan gum, are also included.

In some embodiments, the formulation of the HSLS can be (by weight): 5-80% nanoparticles of polymer-associated active ingredients and herbicide safener (including the polymer, active ingredient and herbicide safener, optionally in aggregate form), 0.5-5% wetting agent and/or dispersant, 1-10% anti-freezing agent, 0.2-2% anti-settling agent or thickener, 0.01-0.1% preservative, and water up to 100%.

In some embodiments, a HSLS is made by reconstituting the dried dispersion (e.g., freeze dried) of polymer-associated active ingredients and herbicide safener in water to obtain a formulation that is more than 60% solids by weight and then adding an anti-freezing agent (and optionally a thickening agent and a preservative) to the final mixture. In some embodiments, a HSLS is made by reconstituting the milled (e.g. ball-milled) solid of nanoparticles of polymer-associated active ingredient and herbicide safener in water to obtain a formulation that is more than 60% solids by weight and then adding an anti-freezing agent (and optionally a thickening agent and a preservative) to the final mixture. In some embodiments, the HSLS is made by homogenizing all the components together. In some embodiments the HSLS is made by milling all the components together.

In some embodiments, a HSLS formulation comprising nanoparticles of polymer-associated active ingredient and optionally a herbicide safener (optionally in aggregate form) can be made from the dispersion of polymer nanoparticles and active ingredient in a common solvent, preferably methanol. In some embodiments, the dispersion is added to an aqueous solution containing a wetting agent and a dispersant, an anti-freezing agent (and optionally an anti-settling agent or thickener and a preservative, and optionally a herbicide safener). The mixture is then concentrated by removing solvent, e.g., by drying, until the desired high solids formulation is attained.

In some embodiments, the polymer nanoparticles are made from a co-polymer of methacrylic acid and ethyl acrylate at a 90:10 mass ratio. In some embodiments, the polymer nanoparticles are made from a co-polymer of methacrylic acid and ethyl acrylate at a 75:25 mass ratio. In some embodiments, the polymer nanoparticles are made from a co-polymer of methacrylic acid and styrene at a 90:10 mass ratio. In some embodiments, the polymer nanoparticles are made from a co-polymer of methacrylic acid and styrene at a 75:25 mass ratio. In some embodiments, the polymer nanoparticles are made from a co-polymer of methacrylic acid and butylmethacrylate at a 75:25 mass ratio. In some embodiments, the polymer nanoparticles are dispersed in the common solvent, preferably at a concentration of 20 mg/mL. In some embodiments, the active ingredient is fenoxaprop-P-ethyl and is mixed into the nanoparticle dispersion at a concentration of 20 mg/mL.

In some embodiments, the dispersion of polymer nanoparticles and active ingredient and optionally herbicide safener in a common solvent is slowly added into a vessel containing a second solvent, preferably water. In some embodiments, the second solvent is at least 20 times larger in volume than the common solvent containing the polymer nanoparticles and active ingredient. In some embodiments, the second solvent contains a dispersant, preferably a lignosulfonate such as Reax 88B and/or a wetting agent, preferably a surfactant such as sodium dodecylbenzene sulfonate. In some embodiments a HSLS can be made using a wetting agent (e.g., a surfactant such as sodium dodecylbenzene sulfonate) and a dispersant (e.g., a lignosulfonate such as Reax 88B, etc.).

In some embodiments, after the dispersion of polymer nanoparticles and active ingredient and optionally herbicide safener in a common solvent is mixed with a second solvent containing a wetting agent and/or dispersant and an anti-freezing agent (optionally with an anti-settling agent or thickener and a preservative), the final mixture is concentrated by removing most of the common solvent and second solvent until a final formulation of at least 60% solids is left. In some embodiments, the method used to concentrate the solution is vacuum evaporation. In some embodiments, a second solvent containing a wetting agent and/or dispersant and an anti-freezing agent (optionally with an anti-settling agent or thickener and a preservative) are added after the mixture has already been concentrated.

In some embodiments, the dispersion of polymer nanoparticles and active ingredient in a common solvent is added to a second solvent to form a solution of nanoparticles of polymer-associated active ingredients (optionally in aggregate form). The second solvent is typically miscible with the common solvent and is usually water, but in some embodiments, the second solvent can also be a mixture of water with a third solvent, usually an alcohol, preferably methanol or ethanol. In some embodiments, the second solvent or mixture of solvents is only partially miscible with the common solvent. In some embodiments, the second solvent or mixture of solvents is not miscible with the common solvent.

In some embodiments, the dispersion of polymer nanoparticles, active ingredient and herbicide safener in a common solvent is added to a second solvent to form a solution of nanoparticles of polymer-associated active ingredients and herbicide safener (optionally in aggregate form). The second solvent is typically miscible with the common solvent and is usually water, but in some embodiments, the second solvent can also be a mixture of water with a third solvent, usually an alcohol, preferably methanol or ethanol. In some embodiments, the second solvent or mixture of solvents is only partially miscible with the common solvent. In some embodiments, the second solvent or mixture of solvents is not miscible with the common solvent.

In various embodiments, the present invention provides formulations as high solids content dispersions of the active ingredient in water. These high concentration suspensions, which we call high-solids liquid suspensions (HSLSs), contain large amount of active ingredient associated with polymer nanoparticles in the concentrated formulations. The preparation of HSLS formulations was described extensively, above. The HSLS suspensions can be added to water in a spraying apparatus (e.g. spray tank), agitated and applied to the pestilent plant.

While these formulations look like traditional suspension concentrates available from active ingredient manufacturers, they are prepared using different procedures. We typically first manufacture the polymer nanoparticles, load them with active ingredient, and form the high-concentration liquid suspension either by drying the loaded polymer nanoparticles (with formulation agents if necessary) and re-suspending at the desired concentration. Alternatively, high concentration liquid suspensions with our polymer nanoparticles can be made by using water as the solvent during the loading process and removing water until the loaded polymer nanoparticles are at the desired concentration. Traditional suspension concentrates also require an anti-settling agent or thickener such as xanthan gum. The gum provides a polymer network that helps stabilize the micron-sized particles of active ingredient and prevent settling and coalescence. In our formulations, this is not required, because our particle size is smaller (nano vs. micro size) and hence settling and coalescence is less of a problem. In addition, without wishing to be limited by any theory, it is thought that the polymer nanoparticles themselves can help stabilize the formulation when dispersed at high concentration in water.

As discussed above many AOPPs, DIMs and triazolinone inhibitors of PPOs undergo hydrolysis. This susceptibility to hydrolysis renders some of these herbicides difficult to formulate into SCs using standard procedures. The present invention allows for the preparation of HSLS formulations of these active ingredients by avoiding milling of the active ingredient, which generates heat and in some cases may accelerate degradation (e.g. hydrolysis). Alternatively, the present invention allows for the preparation HSLS formulations by milling the active ingredient and polymer nanoparticle in the presence of other formulating agents. Alternatively, the present invention allows for the preparation HSLS formulations by milling nanoparticles of polymer-associated active ingredients and optionally herbicide safener in the presence of other formulating agents. Surprisingly, concentrated HSLS formulations can be produced using these milling methods without the decomposition or destabilization of the active ingredient that is associated with traditional suspension concentrate preparation procedures.

Without wishing to be limited by any theory, it is thought that the association of the active ingredient with the polymer nanoparticles provides stabilization against degradation during formulation.

In various embodiments, the present invention provides concentrated aqueous HSLS formulations of AOPPs, CHDs and triazolinone inhibitors of PPO that have enhanced storage and stability properties. In various embodiments, the present invention provides HSLS formulations of these active ingredients that display increased resistance to hydrolysis compared to the unformulated herbicide or commercially available suspension concentrates. In various embodiments, the present invention provides concentrated aqueous HSLS formulations of AOPPs, CHDs, triazolinone, and triazolinone inhibitors of PPO that are stable to temperature cycling. In some embodiments, the formulations suppress re-crystallization or phase separation of the active ingredient, even after repeated temperature cycling. Without wishing to be limited by any theory, it is thought that the association of the active ingredient with the polymer nanoparticles provides stabilization against degradation during storage and temperature cycling.

Efficacy and Application

As noted previously and in the Examples, in some embodiments, the invention provides formulations of herbicides that have improved efficacy against weeds (pestilent plants). In some embodiments, there is increased efficacy against grasses (e.g. green foxtail and corn seedlings). In some embodiments, there is a decrease in biomass of plants inoculated with formulations containing nanoparticles of polymer-associated active ingredients via spraying. In some embodiments, the increased efficacy corresponds to a decrease in the in the $GR_{50}$ of the formulation by between 1.25 times and 5 times, e.g., as compared to an emulsion concentrate (EC) formulation with the same active ingredient (e.g., Excel Super EC in the case of fenoxaprop-P-ethyl). In some embodiments, the increased efficacy corresponds to a decrease in the $GR_{50}$ of the formulation by between 1.25 times and 3 times. In some embodiments, the increased efficacy corresponds to a decrease in the $GR_{50}$ of the formulation by between 1.5 times and 5 times. In some embodiments, the increased efficacy corresponds to a decrease in the $GR_{50}$ of the formulation by between 2 times and 5 times. In some embodiments, the increased efficacy corresponds to a decrease in the $GR_{50}$ of the formulation by between 2.5 times and 5 times. In some embodiments, the increased efficacy corresponds to a decrease in the $GR_{50}$ of the formulation by between 3 times and 5 times. In some embodiments, the increased efficacy corresponds to a decrease in the $GR_{50}$ of the formulation by more than 5 times. In some embodiments, the increased efficacy corresponds to a decrease in the $GR_{50}$ of the formulation by between 2 times and 3 times.

Without wishing to be bound by any theory, it is thought that in some cases the increased efficacy is due to improved absorption of herbicides in formulations comprising nanoparticles of polymer-associated herbicides compared to standard commercial herbicide formulations. Without wishing to be bound by any theory, it is thought that in some cases the increased efficacy is due to increased resistance to hydrolysis of herbicides formulated as nanoparticles of polymer-associated herbicides (e.g. herbicides containing hydrolysable functional groups such as, but not limited to esters) compared to standard commercial herbicide formulations. Without wishing to be bound by any theory, it is thought that an increased resistance to hydrolysis of herbicides formulated as nanoparticles of polymer-associated herbicides could contribute to improved herbicide uptake. For example it is known that AOPPs (e.g. fenoxaprop-P-ethyl) are more plant-permeable and efficacious when applied as esters (e.g. alkyl esters, propargyl esters) than as acid derivatives, and are thus normally formulated as esters for end-use applications. Without wishing to be bound by any theory, in some cases, the increased efficacy is due to a combination of any of the aforementioned scenarios.

In some embodiments, there is increased efficacy against grass species (e.g. green foxtail) that have been inoculated with a formulation containing nanoparticles of polymer-associated herbicide via spraying at herbicide concentrations as low as about 5 parts per million. In some embodiments, there is increased efficacy against grass species (e.g. green foxtail) that have been inoculated with a formulation containing nanoparticles of polymer-associated herbicides via spraying with herbicide concentrations in the range of about 1 to about 1000 parts per million.

In general, different herbicides are typically applied at different effective rates between 0.01 and 1000 g/hectare depending on the efficacy of the herbicide (e.g., absolute potency of the active and retention at the site of activity), as well as the characteristics of non-target plants, leaf type, environmental conditions, the species of pestilent plant, infestation levels, and other factors. Some embodiments of the invention demonstrate improvements in efficacy over typical commercial formulation and therefore suggest that lower rates of effective application could be used. In some embodiments, rates according to the invention may range from 0.1-1000 g/hectare, preferably 0.1-600 g/hectare, 0.1-400 g/hectare, more preferably 0.1-200 g/hectare, more preferably 0.1-100 g/hectare, more preferably 0.1-10 g/hectare or more preferably 0.1-1 g/hectare. In some embodiments, rates according to the invention may range from 1-1000 g/hectare, preferably 1-600 g/hectare, more preferably 1-400 g/hectare, more preferably 1-200 g/hectare, more preferably 1-100 g/hectare, or more preferably 1-10 g/hectare. In some embodiments, concentrations according to the invention may range from 5-1000 g/hectare, preferably 5-600 g/hectare, more preferably 5-400 g/hectare, more preferably 5-200 g/hectare, more preferably 5-100 g/hectare, or more preferably 5-10 g/hectare.

A formulation of a given active ingredient prepared according to the present invention can be used to control any of the pestilent species currently controlled by commercially available formulations of the same active ingredient in any intended use of the commercially available formulation (e.g. in protection of a certain crop, such as sweet corn). This information can be obtained from commercial supplier labels, which are readily accessible and available.

In some embodiments, the formulations of the present invention can be used to control weeds in agricultural and non-agricultural uses. For example, depending on the active ingredient, weeds can be controlled in crops, ornamentals, tobacco, greenhouse crops, trees and in other applications in which current herbicide products are used to control weeds. The formulations can also be used in silviculture or horticulture (such as edibles and ornamentals).

In some embodiments, the AOPP formulations of the present invention can be used to control weeds in a variety of crops. Non-limiting examples of crops in which weeds can be controlled by AOPP formulations of the present invention include barley, beans, beets, cotton, flax, fodder beet, leaf vegetables, leguminous crops, oilseed rape, onions, peanuts, peas, potatoes, rye, soya beans, sugar beet, sunflowers, strawberries, triticale, vines, vegetables and wheat and other crops in which weeds are currently controlled by commercial formulations of AOPP. In some embodiments, the crop or crops in which weeds can be controlled by AOPP formulations of the present invention may depend on, among other variables, the active ingredient, inclusion of other components into the formulation (e.g. safeners), and the particular application. Common commercial formulations frequently include labels and instructions describing the compatibility of actives, safeners, particular applications as well as other variables. Such labels and instructions pertinent to the formulations of the present inventions are also contemplated as part of the present inventions.

In some embodiments, the CHD formulations of the present invention can be used to control weeds in a variety of crops. Non-limiting examples of crops in which weeds can be controlled by CHD formulations of the present invention include alfalfa, alliums, barley, beans, beets, brassicas, cotton, flax, fodder beet, oilseed rape, onions, peanuts, peas, potatoes, soya beans, sugar beet, sunflowers, strawberries, spinach, tobacco, vines, vegetables, wheat, and other crops currently protected by commercial formulations of CHDs. In some embodiments, the crop or crops in which weeds can be controlled by CHD formulations of the present invention may depend on, among other variables, the active ingredient, inclusion of other components into the formulation (e.g. safeners), and the particular application. Common commercial formulations frequently include labels and instructions describing the compatibility of actives, safeners, particular applications as well as other variables. Such labels and instructions pertinent to the formulations of the present inventions are also contemplated as part of the present inventions.

In some embodiments, the formulations of triazolinone inhibitors of PPO of the present invention can be used to control weeds in a variety of crops. Non-limiting examples of crops in which weeds can be controlled by triazolinone formulations of the present invention include cereals (e.g. wheat, barley, rice, maize), sugar cane, soya beans and tobacco, and other crops currently protected by commercial formulations of triazolinone inhibitors of PPO. In some embodiments, the crop or crops in which weeds can be controlled by triazolinone formulations of the present invention may depend on, among other variables, the active ingredient, inclusion of other components into the formulation (e.g. safeners), and the particular application. As mentioned above, common commercial formulations frequently include labels and instructions describing the compatibility of actives, safeners, particular applications as well as other variables. Such labels and instructions pertinent to the formulations of the present inventions are also contemplated as part of the present inventions.

In some embodiments, the sulfonamide formulations of the present invention can be used to control weeds in a variety of crops. Non-limiting examples of crops in which weeds can be controlled by sulfonamide formulations of the present invention include alfalfa, alliums, barley, beans, beets, brassicas, cotton, flax, fodder beet, oilseed rape, onions, peanuts, peas, potatoes, soya beans, sugar beet, sunflowers, strawberries, spinach, tobacco, vines, vegetables, wheat, and other crops currently protected by commercial formulations of sulfonamides. In some embodiments, the crop or crops in which weeds can be controlled by sulfonamide formulations of the present invention may depend on, among other variables, the active ingredient, inclusion of other components into the formulation (e.g. safeners), and the particular application. Common commercial formulations frequently include labels and instructions describing the compatibility of actives, safeners, particular applications as well as other variables. Such labels and instructions pertinent to the formulations of the present inventions are also contemplated as part of the present inventions.

In some embodiments, the sulfonylurea formulations of the present invention can be used to control weeds in a variety of crops. Non-limiting examples of crops in which weeds can be controlled by sulfonylurea formulations of the present invention include alfalfa, alliums, barley, beans, beets, brassicas, cotton, flax, fodder beet, oilseed rape, onions, peanuts, peas, potatoes, soya beans, sugar beet, sunflowers, strawberries, spinach, tobacco, vines, vegetables, wheat, and other crops currently protected by commercial formulations of sulfonylureas. In some embodiments, the crop or crops in which weeds can be controlled by sulfonylurea formulations of the present invention may depend on, among other variables, the active ingredient, inclusion of other components into the formulation (e.g. safeners), and the particular application. Common commercial formulations frequently include labels and instructions describing the compatibility of actives, safeners, particular applications as well as other variables. Such labels and instructions pertinent to the formulations of the present inventions are also contemplated as part of the present inventions.

In some embodiments, the invention provides methods of using formulations of nanoparticles of polymer-associated active ingredients. In some embodiments, the formulations are used to inoculate a plant. In some embodiments, the formulations are used to inoculate a part or several parts of the plant, e.g., the leaves, stem, roots, flowers, bark, buds, shoots, and/or sprouts.

In some embodiments, a formulation comprising nanoparticles of polymer-associated active ingredients and other formulating agents is added to water (e.g., in a spray tank) to make a dispersion that is about 10 to about 2,000 ppm in active ingredient. In some embodiments, the dispersion is about 10 to about 1,000 ppm, about 10 to about 500 ppm, about 10 to about 300 ppm, about 10 to about 200 ppm, about 10 to about 100 ppm, about 10 to about 50 ppm, about 10 to about 20 ppm, about 20 to about 2,000 ppm, about 20 to about 1,000 ppm, about 20 to about 500 ppm, about 20 to about 300 ppm, about 20 to about 200 ppm, about 20 to about 100 ppm, about 20 to about 50 ppm, about 50 to about 2,000 ppm, about 50 to about 1,000 ppm, about 50 to about 500 ppm, about 50 to about 300 ppm, about 50 to about 200 ppm, about 50 to about 100 ppm, about 100 to about 2,000 ppm, about 100 to about 1,000 ppm, about 100 to about 500 ppm, about 100 to about 300 ppm, about 100 to about 200 ppm, about 200 to about 2,000 ppm, about 200 to about 1,000 ppm, about 200 to about 500 ppm, about 200 to about 300 ppm, about 300 to about 2,000 ppm, about 300 to about 1,000 ppm, about 300 to about 500 ppm, about 500 to about 2,000 ppm, about 500 to about 1,000 ppm, about 1000 to about 2,000 ppm.

The formulations of the present invention can be used to control a variety of agronomically important weeds. As used herein, the term "weed" or "pestilent plant" includes undesirable crop species such as volunteer crops. The AOPP and CHD formulations of the present invention can be used, variously, for the post-emergence control of a variety of perennial and annual grass weeds. The triazolinone formulations of the present invention can be used, variously, depending on the active ingredient, for the control of grass and broadleaved weeds.

In some embodiments, a dispersion of active ingredient is produced that is applied for the control of pestilent plants (weeds) at less than 75% of the rate normally listed on the label of current herbicide products. In some embodiments, a dispersion of active ingredient is produced that is applied for the control of pestilent plants (weeds) at less than half the rate normally listed on the label of current herbicide products. In some embodiments, a dispersion of active ingredient is produced that is applied for the control of pestilent plants (weeds) at less than 25% of the rate normally listed on the label of current herbicide products. In some embodiments, a dispersion of active ingredient is produced that is applied for the control of pestilent plants (weeds) at less than 10% of the rate normally listed on the label of current herbicide products. In some embodiments, a dispersion of active ingredient is produced that is applied for the control of pestilent plants (weeds) at less than 5% of the rate normally listed on the label of current herbicide products. Herbicide labels can be referenced from current suppliers and are commonly available.

In some embodiments, the inoculation method is applied to individual pestilent plants or to large groups of pestilent plants. In some embodiments, the target weed is inoculated by means of dipping the target or part of the organism into a dispersion containing formulation. In some embodiments, the formulation is applied to the target pestilent plants by means of an aerosol spray. In some embodiments, the formulation is inoculated on the target by spraying the dispersion directly onto the leaves, stem, bud, shoot or flowers of the plant. In some embodiments the target plant is inoculated with the formulation, by pouring the dispersion directly onto the root zone of the plant.

Formulations with Improved Properties and Methods of Using these Formulations

Solubility

In some embodiments, the invention provides formulations of herbicides in which the herbicide is dispersed in water or aqueous systems (e.g. HSLSs) at a concentration that is higher that the solubility of the herbicide in water (pH 7 and 20° C.). In some embodiments, the herbicide is dispersed in water in an amount that is more than 1.5 times greater than its solubility in water. In some embodiments, the herbicide is dispersed in water in an amount that is more than 5 times greater than its solubility in water. In some embodiments, the herbicide is dispersed in water in an amount that is more than 10 times greater than its solubility in water. In some embodiments, the herbicide is dispersed in water in an amount that is more than 20 times greater than its solubility in water. In some embodiments, the herbicide is dispersed in water in an amount that is more than 50 times greater than its solubility in water. In some embodiments, the herbicide is dispersed in water in an amount that is more than 100 times greater than its solubility in water. In some embodiments, the herbicide is dispersed in water in an amount that is more than 500 times greater than its solubility in water. In some embodiments, the herbicide is dispersed in water in an amount that is more than 1000 times greater than its solubility in water. In some embodiments, the herbicide is dispersed in water in an amount that is more than 10,000 times greater than its solubility in water. In some embodiments, the herbicide is dispersed in water in an amount that is more than 50,000 times greater than its solubility in water. In some embodiments, the herbicide is dispersed in water in an amount that is more than 200,000 times greater than its solubility in water. In some embodiments, the herbicide is dispersed in water in an amount that is more than 500,000 times greater than its solubility in water. In some embodiments, the herbicide is dispersed in water in an amount that is more than 1,000,000 times greater than its solubility in water.

In some embodiments, the herbicide can be dispersed in water in an amount that is between about 1.5 and about 1,000,000 times greater than its solubility in water. In some embodiments, the herbicide can be dispersed at in amounts between about 5 times and about 1,000,000 times, about 10 times and about 1,000,000 times, about 50 times and about 1,000,000 times, about 100 times and about 1,000,000 times, about 1000 times and about 1,000,000 times, about 10,000 times and about 1,000,000 times, about 5 times and about 500,000 times, about 5 times and about 100,000 times, about 5 times and about 50,000 times, about 5 times and about 10,000 times, about 5 times and about 5,000 times, about 5 times and about 1000 times, about 5 times and about 500 times, about 5 times and about 100 times, about 50 times and about 1,000,000 times, about 50 times and about 500,000 times, about 50 times and about 100,000 times, about 50 times and about 50,000 times, about 50 times and about 10,000 times, about 50 times and about 1,000 times, about 50 times and 500 times, about 200 times and about 1,000,000 times, about 200 times and about 500,000 times, about 200 times and about 100,000 times, 200 times and about 10,000 times, 200 times and about 1000 times, about 500 times and about 1,000,000 times, about 500 times and about 500,000 times, about 500 times and about 100,000 times, 500 times and about 10,000 times, 500 times and about 1000 times, about 1000 times and about 1,000,000 times, about 1000 times and about 1000,000 times, about 1000 times and about 100,000 times, about 1000 times and about 10,000 times, about 10,000 times and about 1,000,000 times, and about 10,000 times or about 100,000 times greater than its solubility in water.

In some embodiments the solubility of the active ingredient in water can be adjusted by modifying pH or other solution conditions. In some embodiments, e.g. cases in which the solubility of the active ingredient is adjusted by changing solution conditions, the invention provides formulations in which the herbicide is dispersed in an amount corresponding to any of the values or ranges listed above in the Efficacy and Application section or in other parts of this disclosure.

In some embodiments, the present invention provides methods of dispersing an herbicide in water at a concentration that is higher that its solubility in water (pH 7 and 20° C.). In some embodiments, this involves associating the herbicide with pre-formed polymer nanoparticles according to the procedures described above. In some embodiments, this involves preparing formulations comprising nanoparticles of polymer-associated active ingredients and optionally herbicide safener, as described above, and dispersing them in water. In some embodiments, the present invention provides methods for dispersing the active ingredient in amounts that correspond to any of the values or ranges above in the Efficacy and Application section or in other parts of this disclosure.

Hydrolysis

In some embodiments, the present invention provides formulations of herbicides in which the herbicide is more resistant to hydrolysis as compared to the unformulated herbicide or the herbicide in commercially available formulations. In some embodiments, the herbicides are more resistant to hydrolysis in neutral, basic, or acidic media. In some embodiments, the present invention provides formulations of herbicides that are more resistant to hydrolysis at about pH 1, about pH 2, about pH 3, about pH 4, about pH 5, about pH 6, about pH 7, about pH 8, about pH 9, about pH 10, about pH 11, about pH 12 or about pH 13. In some embodiments, the present invention provides formulations of herbicides that are more resistant to hydrolysis between about pH 1 and pH 13, about pH 1 and about pH 11, about pH 1 and about pH 9, about pH 1 and about pH 7, about pH 1 and about pH 5, about pH 1 and about pH 3, about pH 3 and pH 13, about pH 3 and about pH 11, about pH 3 and about pH 9, about pH 3 and about pH 7, about pH 3 and about pH 5, about pH 5 and about pH 13, about pH 5 and about pH 11, about pH 5 and about pH 9, about pH 5 and about pH 7, about pH 7 and pH 13, about pH 7 and about pH 11, about pH 7 and about pH 9, about pH 9 and pH 13, about pH 9 and about pH 11, about pH 4 and about pH 8, about pH 4 and about pH 7, about pH 4 and about pH 6, about pH 4 and about pH 5, about pH 6 and about pH 8, about pH 6 and about pH 7, about pH 7 and about pH 8 or about pH 8 and about pH 9. The hydrolysis of the active ingredient was investigated using the procedures outlined in the "OECD Guidelines for the Testing of Chemicals 111: Hydrolysis as a Function of pH" or modifications of these procedures.

In some embodiments, the increased resistance to hydrolysis of the herbicide of formulations of the present invention corresponds to an increase in its $DT_{50}$ of about 1.25 times or more as compared to unformulated herbicide or the herbicide in commercially available formulations. In some embodiments, the increased resistance to hydrolysis corresponds to an increase in $DT_{50}$ of about 3 times or more. In some embodiments, the increased resistance to hydrolysis corresponds to an increase in $DT_{50}$ of about 5 times or more. In some embodiments, the increased resistance to hydrolysis corresponds to an increase in $DT_{50}$ of 10 times or more. In some embodiments, the increased resistance to hydrolysis corresponds to an increase in $DT_{50}$ of 20 times or more. In some embodiments, the increased resistance to hydrolysis corresponds to an increase in $DT_{50}$ of 50 times or more. In some embodiments, the increased resistance to hydrolysis corresponds to an increase in $DT_{50}$ of 100 times or more. In some embodiments, the increased resistance to hydrolysis corresponds to an increase in $DT_{50}$ of 500 times or more. In some embodiments, the increased resistance to hydrolysis corresponds to an increase in $DT_{50}$ of 1000 times or more.

In some embodiments, the increased resistance to hydrolysis of the herbicide corresponds to an increase in its $DT_{50}$ of between about 1.25 times and about 1000 times, e.g. between about 1.25 times and about 1000 times, between about 3 times and about 1000 times, between about 5 times and about 1000 times, between about 10 times and about 1000 times, between about 20 times and about 1000 times, between about 50 times and about 1000 times, between about 100 times and about 1000 times, between about 500 times and about 1000 times, between about 1.25 times and about 500 times, between about 3 times and about 500 times, between about 5 times and about 500 times, between about 10 times and about 500 times, between about 20 times and about 500 times, between about 50 times and about 500 times, between about 100 times and about 500 times, between about 1.25 times and about 100 times, between about 3 times and about 100 times, between about 5 times and about 100 times, between about 10 times and about 100 times, between about 20 times and about 100 times, between about 50 times and about 100 times, between about 1.25 times and about 50 times, between about 3 times and about 50 times, between about 5 times and about 50 times, between about 10 times and about 50 times, between about 20 times and about 50 times, between about 1.25 times and about 20 times, between about 3 times and about 20 times, between about 5 times and about 20 times, between about 10 times and about 20 times, between about 1.25 times and about 10 times, between about 3 times and about 10 times, between about 5 times and about 10 times, between about 1.25 times and about 5 times, between about 3 times and about 5 times, or between about 1.25 times and about 3 times.

In some embodiments, the present invention provides methods of increasing the resistance of an herbicide to hydrolysis. In some embodiments, this involves associating the herbicide with pre-formed polymer nanoparticles according to the procedures described above. In some embodiments, this involves preparing formulations comprising nanoparticles of polymer-associated herbicides and optionally herbicide safener, as described above. In some embodiments, the present invention provides methods for increasing the resistance of an herbicide to hydrolysis in neutral, basic, or acidic media e.g. at any of the pHs or ranges of pH noted above. In some embodiments, the increased resistance to hydrolysis corresponds to an increase in the $DT_{50}$ of any of the values or ranges of values noted above.

In some embodiments, the hydrolytic stability of the active ingredient of formulations of the present invention depends on the nature of the pre-formed polymer nanoparticles. As described in the examples, in some embodiments, different powder formulations were prepared using polymer nanoparticles of various compositions, and the hydrolysis of the active ingredient in these formulations (e.g. fenoxaprop-P-ethyl) was analyzed via thin layer chromatography. Hydrolysis products were observed in some but not all of the formulations. Without wishing to be limited by any theory, it is thought that the interaction between polymer nanoparticles and active ingredients can lead to increased resistance to hydrolysis, that these interactions will differ depending on the composition of the nanoparticle, and that nanoparticles of different compositions will thus provide different levels of stabilization. In some embodiments, the hydrolytic stability of the active ingredient of formulations of the present invention depends on the formulation process (e.g. nature of association step).

Increased Resistance to Photolysis

In some embodiments, the present invention provides formulations herbicides in which the herbicide is more resistant to photolysis as compared to the unformulated herbicide or the herbicide in commercially available formulations. In some embodiments, the herbicide is more resistant to hydrolysis in neutral, basic, or acidic media. In some embodiments, the present invention provides formulations of herbicides that are more resistant to photolysis at about pH 1, about pH 2, about pH 3, about pH 4, about pH 5, about pH 6, about pH 7, about pH 8, about pH 9, about pH 10, about pH 11, about pH 12 or about pH 13. In some embodiments, the present invention provides formulations of herbicides that are more resistant to photolysis between about pH 1 and pH 13, about pH 1 and about pH 11, about pH 1 and about pH 9, about pH 1 and about pH 7, about pH 1 and about pH 5, about pH 1 and about pH 3, about pH 3 and pH 13, about pH 3 and about pH 11, about pH 3 and about pH 9, about pH 3 and about pH 7, about pH 3 and about pH 5, about pH 5 and about pH 13, about pH 5 and about pH 11, about pH 5 and about pH 9, about pH 5 and about pH 7, about pH 7 and pH 13, about pH 7 and about pH 11, about pH 7 and about pH 9, about pH 9 and pH 13, about pH 9 and about pH 11, about pH 4 and about pH 8, about pH 4 and about pH 7, about pH 4 and about pH 6, about pH 4 and about pH 5, about pH 6 and about pH 8, about pH 6 and about pH 7, about pH 7 and about pH 8 or about pH 8 and about pH 9. The photolytic degradation of the active ingredient was investigated using the procedures outlined in the "OECD Guidelines for the Testing of Chemicals 316: Phototransformation of Chemicals in Water—Direct Photolysis" or modifications of these procedures.

In some embodiments, the increased resistance to photolytic degradation of the herbicide of formulations of the present invention corresponds to an increase in its $DT_{50}$ of about 1.25 times or more. In some embodiments, the increased resistance to photolysis corresponds to an increase in $DT_{50}$ of about 3 times or more. In some embodiments, the increased resistance to photolysis corresponds to an increase in $DT_{50}$ of about 5 times or more. In some embodiments, the increased resistance to photolysis corresponds to an increase in $DT_{50}$ of 10 times or more. In some embodiments, the increased resistance to photolysis corresponds to an increase in $DT_{50}$ of 20 times or more. In some embodiments, the increased resistance to photolysis corresponds to an increase in $DT_{50}$ of 50 times or more. In some embodiments, the increased resistance to photolysis corresponds to an increase in $DT_{50}$ of 100 times or more. In some embodiments, the increased resistance to photolysis corresponds to an increase in $DT_{50}$ of 500 times or more. In some embodiments, the increased resistance to photolysis corresponds to an increase in $DT_{50}$ of 1000 times or more.

In some embodiments, the increased resistance to photolysis of the herbicide corresponds to an increase in its $DT_{50}$ of between about 1.25 times and about 1000 times, e.g. between about 1.25 times and about 1000 times, between about 3 times and about 1000 times, between about 5 times and about 1000 times, between about 10 times and about 1000 times, between about 20 times and about 1000 times, between about 50 times and about 1000 times, between about 100 times and about 1000 times, between about 500 times and about 1000 times, between about 1.25 times and about 500 times, between about 3 times and about 500 times, between about 5 times and about 500 times, between about 10 times and about 500 times, between about 20 times and about 500 times, between about 50 times and about 500 times, between about 100 times and about 500 times, between about 1.25 times and about 100 times, between about 3 times and about 100 times, between about 5 times and about 100 times, between about 10 times and about 100 times, between about 20 times and about 100 times, between about 50 times and about 100 times, between about 1.25 times and about 50 times, between about 3 times and about 50 times, between about 5 times and about 50 times, between about 10 times and about 50 times, between about 20 times and about 50 times, between about 1.25 times and about 20 times, between about 3 times and about 20 times, between about 5 times and about 20 times, between about 10 times and about 20 times, between about 1.25 times and about 10 times, between about 3 times and about 10 times, between about 5 times and about 10 times, between about 1.25 times and about 5 times, between about 3 times and about 5 times, or between about 1.25 times and about 3 times.

In some embodiments, the present invention provides herbicides in which the herbicide is more resistant to hydrolysis as compared to the unformulated herbicide or commercially available formulations of the same active ingredient when cast onto a mi microscope slide and exposed to a solar simulator (Fade Test UV simulator, model 16S-300-003; Solar Light Co, Glenside, Pa. USA) for different periods of time (5 mins-240 mins) as determined by thin layer chromatography (TLC).

In various embodiments, the present invention provides herbicide formulations that do not include a UV blocker.

In some embodiments, the present invention provides methods of increasing the resistance of an herbicide to photolysis. In some embodiments, this involves associating the herbicide with pre-formed polymer nanoparticles according to the procedures described above. In some embodiments, this involves preparing formulations comprising nanoparticles of polymer-associated herbicides and optionally herbicide safeners, as described above. In some embodiments, the present invention provides methods for increasing the resistance of an herbicide to photolysis in neutral, basic, or acidic media e.g. at any of the pHs or ranges of pH noted above. In some embodiments, the increased resistance to photolysis corresponds to an increase in the $DT_{50}$ of any of the values or ranges of values noted above.

Improved Foliar Uptake

In some embodiments, the invention provides formulations that improve the foliar uptake of the active ingredient as compared to the unformulated herbicide or commercially available formulations of the same active ingredient. In some embodiments, pestilent plants (weeds) are inoculated with formulations of the present invention or commercially available formulations of the same active ingredient. After a specific amount of time, the samples are collected, and the foliar uptake of the herbicide from each of the formulations is assessed by washing the samples with solvent and quantifying the amount of herbicide residue in the washings and in the plant (by for example, using HPLC analysis or quantifying radioactivity of a radiolabeled active). In some embodiments, a smaller amount of herbicide residue is found in the washings of plants inoculated with formulations of the present invention as compared to plants inoculated with commercial formulations of the same active ingredient. In some embodiments, less than about 5% of the herbicide is found in washings of plants inoculated with formulations of the current invention. In some embodiments, less than about 10% of the herbicide is found in washings of plants inoculated with formulations of the current invention. In some embodiments, less than about 15% of the herbicide is found in washings of plants inoculated with formulations of the current invention. In some embodiments, less than about 20% of the herbicide is found in washings of plants inoculated with formulations of the current invention. In some embodiments, less than about 25% of the herbicide is found in washings of plants inoculated with formulations of the current invention. In some embodiments, less than about 30% of the herbicide is found in washings of plants inoculated with formulations of the current invention. In some embodiments, less than about 35% of the herbicide is found in washings of plants inoculated with formulations of the current invention. In some embodiments, less than about 40% of the herbicide is found in washings of plants inoculated with formulations of the current invention. In some embodiments, less than about 45% of the herbicide is found in washings of plants inoculated with formulations of the current invention. In some embodiments, less than about 50% of the herbicide is found in washings of plants inoculated with formulations of the current invention. In some embodiments, less than about 55% of the herbicide found in washings of plants inoculated with formulations of the current invention. In some embodiments, less than about 60% of the herbicide found in washings of plants inoculated with formulations of the current invention. In some embodiments, less than about 65% of the herbicide found in washings of plants inoculated with formulations of the current invention. In some embodiments, less than about 70% of the herbicide is found in washings of plants inoculated with formulations of the current invention. In some embodiments, less than about 75% of the herbicide is found in washings of plants inoculated with formulations of the current invention. In some embodiments, less than about 80% of the herbicide is found in washings of plants inoculated with formulations of the current invention. In some embodiments, less than about 85% of the herbicide is found in washings of plants inoculated with formulations of the current invention. In some embodiments, less than about 90% of the herbicide is found in washings of plants inoculated with formulations of the current invention. In some embodiments, less than about 95% of the herbicide is found in washings of plants inoculated with formulations of the current invention.

High Salt Solutions

In some embodiments, the formulations of the present invention were mixed with a concentrated/high salt solution. Traditional solid or liquid formulations are not stable under conditions of high ionic (i.e., a high salt solution) strength. Sources of increased ionic strength can include, for example, mineral ions that are present in the water that a formulation is dispersed in. For example, in many cases the water that is available to a farmer is taken from a high-salt ("hard water") source such as a well or aquifer. Water that a grower uses can be variably hard and is normally measured as $Ca^{2+}$ equivalents. Ranges of water salinity can be from ~0 ppm $Ca^{2+}$ equivalent (deionized water) to 8000 ppm $Ca^{2+}$ or more.

Other sources of increased ionic strength can include, for example, other chemicals or materials that dispersed in the spray tank water before or after the addition of the pesticide formulation. Examples of this include mineral additives such as micronutrients (which can include e.g. B, Cu, Mn, Fe, Cl, Mo, Zn, and S) or traditional N—P—K fertilizers where the nitrogen, phosphorus, or potassium source is in an ionic form. The fertilizer can include e.g. ammonium phosphate or ammonium thiosulphate.

In some cases, the formulations of the present invention can be applied simultaneously with a high-salt solution such as a micronutrient solution or a fertilizer (e.g. in furrow application). Other potential additives that might be added into a spray tank that are charged and can decrease the stability of an agrochemical formulation include charged surfactants or polymers, inert ingredients such as urea, charged active ingredients or formulations of active ingredients (e.g. charged herbicides) that are tank mixed with a formulation of the current invention, or other similar ingredients. As mentioned above, most traditional formulations produce solid particles (floc) or a precipitate when mixed in with high salt, hard water or fertilizer solutions. Surprisingly, a dispersed solid formulation of herbicide of the present invention was stable (e.g. components, herbicide and the salt, remained dissolved, i.e., no visible precipitate or floc) when mixed with a concentrated/high salt solution (e.g. hard water, buffer, concentrated fertilizer formulation). This was true even for waters with ionic strength as high as 8000 ppm $Mg^{2+}$ (a.k.a. CIPAC "G" hard water). For comparison, a commercially available solid formulation was also redispersed in the same manner but started to form flocs when mixed with the high salt solution within ten minutes. It is important to note that for such a mixture to be useful for the end user, the mixture should remain stable (i.e. no formation of sediments and/or flocs) within at least about 30-40 minutes—which is the time it takes for the mixture to be applied. It is surprising that the formulations of the present invention are stable in such high-salt conditions. Because the polymers that are used in the nanoparticles of the present invention are negatively charged, a practitioner of the art would expect the formulations of the present invention to flocculate when mixed with such a high amount of divalent salt. Without being limited by theory, it is believed that the increased stability of the formulations of the present invention arises from the use of nanoparticulate polymers as the delivery system and that if standard non-nanoparticle polymers were used then flocculation would occur.

In some embodiments, the present invention provides compositions of a formulation of nanoparticles of polymer-associated active ingredients optionally herbicide safeners that are redispersible in solutions with high ionic strength. In some embodiments, the present invention also provides compositions of a formulation of nanoparticles of polymer-associated active ingredients and optionally herbicide safeners that can be redispersed in water, have a high salt solution or solid salt added to the dispersion, and maintain their stability. In some embodiments, the formulations of the present invention are stable when dispersed in or dispersed in water and then mixed with solutions with ionic strength corresponding to $Ca^{2+}$ equivalents of about 0 to about 1 ppm, about 0 to about 10 ppm, about 0 to about 100 ppm, about 0 to about 342 ppm, about 0 to about 500 ppm, about 0 to about 1000 ppm, about 0 to about 5000 ppm, about 0 to about 8000 ppm, about 0 to about 10000 ppm, about 1 to about 10 ppm, about 1 to about 100 ppm, about 1 to about 342 ppm, about 1 to about 500 ppm, about 1 to about 1000 ppm, about 1 to about 5000 ppm, about 1 to about 8000 ppm, about 1 to about 10000 ppm, about 10 to about 100 ppm, about 10 to about 342 ppm, about 10 to about 500 ppm, about 10 to about 1000 ppm, about 10 to about 5000 ppm, about 10 to about 8000 ppm, about 10 to about 10000 ppm, about 100 to about 342 ppm, about 100 to about 500 ppm, about 100 to about 1000 ppm, about 100 to about 5000 ppm, about 100 to about 8000 ppm, about 100 to about 10000 ppm, about 342 to about 500 ppm, about 342 to about 1000 ppm, about 342 to about 5000 ppm, about 342 to about 8000 ppm, about 342 to about 10000 ppm, about 500 to about 1000 ppm, about 500 to about 5000 ppm, about 500 to about 8000 ppm, about 500 to about 10000 ppm, about 1000 to about 5000 ppm, about 1000 to about 8000 ppm, about 1000 to about 10000 ppm, about 5000 to about 8000 ppm, about 5000 to about 10000 ppm, about 8000 to about 10000 ppm.

EXAMPLES

Notes and Abbreviations pyroxsulam: technical grade, ~85% purity (by weight)

RO water: water purified via reverse osmosis; DMF: N,N-dimethyl-formamide

Monomer Abbreviations—MAA: methacrylic acid; EA: ethyl acrylate;

Formation of Polymer Nanoparticles and Formulations

Example 1: Preparation of 1 g of Polymer Nanoparticles from poly(methacrylic acid-co-ethyl acrylate) (p(MAA-co-EA))

1 g of polymer nanoparticles derived from p(MAA-co-EA) was made as follows. Briefly, in various iterations of this process MAA:EA ratio was approx. 90:10, approx. 80:20 or approx. 60:40, with MW=450K-800K, however, the process as described was the same. 1 g solid p(MAA-co-EA) was dissolved in 500 mL of deionized water in a 3 L beaker using an overhead stirrer, and pH was maintained at ~7 with 1M NaOH. The solution was stirred overnight to fully dissolve the solid. The next day, 500 mL of 3M NaCl was added to the solution under vigorous stirring. After addition, the solution was left to stir at 500 rpm for another hour. At this stage, the solution viscosity drops indicating the formation of collapsed polymers. The solution was then transferred to a 3 L recrystallization dish equipped with a magnetic stir bar. This solution was exposed to 4-254 nm UV germicidal lamps (G25T8) for 2 hours under constant stirring. After 2 hours, the solution was removed from the UV source and the ions were removed using diafiltration. The resulting retentate was then freeze dried to obtain a powder of the polymer nanoparticles. Alternatively, the retentate could also be spray dried to obtain a powder of the polymer nanoparticles. A particle size of 20-50 nm was measured via dynamic light scattering of a solution of either the collected freeze-dried or spray dried solid re-dispersed in 0.1M NaCl solution, pH adjusted to ~6.8 and stirred overnight.

The polarity of the microenvironment of the nanoparticles was investigated according to the method outlined in *Photochem. Photobiol.* 1982, 35:17. Briefly, 10 µL of a 0.1 mg/mL solution of pyrene in $CH_2Cl_2$ was placed in a 20 ml scintillation vial and the liquid was swirled around to coat the bottom of the vial. The solvent was allowed to evaporate under a fume hood. 10 ml of a 1 mg/mL dispersion of polymer nanoparticles in deionized water (pH adjusted to ~4.5) was added in to the vial with the dried out pyrene solution and was stirred for 48 hours in the dark. Emission spectra were then measured on a Perkin Elmer LS 55 Luminescence Spectrometer using an excitation wavelength of 340 nm, having slit widths for both excitation and emission at 2.5 nm. The emission intensity of the first ($I_1$, ~373 nm) and third ($I_3$, ~384 nm) vibronic bands were recorded and the ratio ($I_1/I_3$) calculated giving a ratio of ~1.18 indicating that the polymer nanoparticles prepared according to Example 1 has a microenvironment similar to the polarity/hydrophobicity of methanol (see table in *Photochem. Photobiol.* 1982, 35:17 for a complete tabulation of the ratios of $I_1/I_3$ and the corresponding microenvironment polarity.)

The same procedure was used to make polymer nanoparticles from different polyelectrolyte co-polymers and polyelectrolyte homopolymers. Examples of other polyelectrolyte copolymers: poly(methacrylic acid (MAA)-co-styrene(S)) (MAA:S=90:10, MW 450K-800K), poly(methacrylic acid (MAA)-co-butylmethacrylate (BUMA)) (MAA:BUMA=75:25, MW 450K-800K).

Example 2: Formation of a Solid Formulation (WP) of Nanoparticles or Aggregates of Nanoparticles of Polymer-Associated Fenoxaprop-P-Ethyl and Mefenpyr-Diethyl Via Spray Drying Directly from a Common Solvent System 2.5 g of polymer nanoparticles derived from p(MAA-co-EA) (MAA:EA=approx. 90:10) were made according to the procedure outlined in Example 1 and dispersed in ~125 mL of methanol. The dispersion was centrifuged at 3000 rpm for 30 minutes and the supernatant was decanted to remove the insoluble fraction. 1.873 g of fenoxaprop-P-ethyl and 0.628 g of mefenpyr-diethyl safener were dissolved in 20 mL of ethyl acetate and added to the dispersion of nanoparticles. The mixture was stirred for 1 hour, then spray dried on a Buchi mini Spray dryer B290 with inlet temperature set at 170° C., aspirator gas flow rate of approximately 35 $m^3/h$, feed rate of approximately 7 mL/min and air flow of 601 L/hr. DSC measurements of the powder revealed no endothermic melting peak corresponding to the pure crystalline active.

Example 3: Formation of a Solid Formulation (WP) of Nanoparticles or Aggregates of Nanoparticles of Polymer-Associated Fenoxaprop-P-Ethyl Via Spray Drying Directly from a Common Solvent System with Nanoparticles of p(MAA-co-EA) [MAA: EA=Approx. 90:10]

5 g of polymer nanoparticles derived from p(MAA-co-EA) (MAA:EA=approx. 90:10) were prepared according to the procedure outlined in Example 1, dispersed in 250 mL of methanol in a 500 mL Nalgene container and stirred for 10 minutes. 5 g of fenoxaprop-P-ethyl was dissolved in 50 mL of ethyl acetate in a 120 mL Nalgene container and stirred for 20 minutes. The solution of fenoxaprop-p-ethyl was then slowly added to the dispersion of nanoparticles (addition rate of approximately 20 mL/min) using a plastic dropper. The resulting dispersion was stirred for an additional 30 minutes and then spray dried on a Yamamoto ADL 311S spray dryer/GAS410 organic solvent recovery unit (inlet temperature of 182° C., outlet temperature of 90° C., aspirator gas flow rate of 0.12 $m^3/min$, feed rate of 17.5 mL/min and atomizing air flow of 10 L/min. The product was recovered as a powder.

Example 4: Formation of a Solid Formulation (WP) of Nanoparticles or Aggregates of Nanoparticles of Polymer-Associated Fenoxaprop-P-Ethyl Via Spray Drying Directly from a Common Solvent System with Nanoparticles of p(MAA-co-EA) [MAA: EA=Approx. 75:25]

5 g of polymer nanoparticles derived from p(MAA-co-EA) (MAA:EA=approx. 75:25) were prepared according to the procedure outlined in Example 1, dispersed in 250 mL of methanol in a 500 mL Nalgene container and stirred for 10 minutes. 5 g of fenoxaprop-P-ethyl was dissolved in 50 mL of ethyl acetate in a 120 mL Nalgene container and stirred for 20 minutes. The solution of fenoxaprop-p-ethyl was then slowly added to the dispersion of nanoparticles (addition rate of approximately 20 mL/min) using a plastic dropper. The resulting dispersion was stirred for an additional 30 minutes and then spray dried on a Yamamoto ADL 311S spray dryer/GAS410 organic solvent recovery unit (inlet temperature of 141-2° C., outlet temperature of 98-100° C., aspirator gas flow rate of 0.43 $m^3/min$, feed rate of 17.5 mL/min and atomizing air flow of 10 L/min. The product was recovered as a powder.

Example 5: Preparation of a Solid Formulation (WP) of Nanoparticles or Aggregates of Nanoparticles of Polymer-Associated Fenoxaprop-P-Ethyl Via Ball Milling 2 g of polymer nanoparticles derived from p(MAA-co-EA) (MAA:EA=approx. 90:10) were prepared according to the procedure outlined in Example 1. The nanoparticles and 2 g of fenoxaprop-P-ethyl were placed in an 80 mL stainless steel milling jar (EQ-MJ-3-80SS, MTI Corporation, Calif., USA) along with 50 g of stainless steel balls (¼"-½" diameter). The jar was sealed and its contents were milled using a desk-top high speed ball mill (MSK-SFM-3, MTI Corporation, Calif., USA) for 8 minutes. The jar was then cooled in an ice bath for 5 minutes and its contents were milled for additional 8 minutes. The jar was cooled for an additional 10 minutes, opened and the resulting powder was collected.

Example 6: Formation of a Solid Formulation (WP) of Nanoparticles or Aggregates of Nanoparticles of Polymer-Associated Pyroxsulam Via Freeze Drying from Water with Nanoparticles of p(MAA-co-EA) [MAA:EA=Approx. 90:10]

Pyroxsulam formulations with theoretical active ingredient contents of 50% (though elemental analysis showed actual weight contents of 40% and 30% for 2A and 2B) by weight were prepared. These two formulation are referred to as CROP 2A and CROP 2B, respectively, below.

CROP 2A: 3.05 g of nanoparticles produced according to Example 1 were mixed in 100 mL of methanol. 3.03 g of pyroxsulam was dissolved in 250 mL of acetone. The methanol solution was added to the acetone solution under constant stirring. The mixture of two solution was then added, dropwise, to 2 L of water. During the addition, the pH was adjusted to 5.4 by addition of 0.1N NaOH solution. The organic solvents were removed by evaporated in a rotary evaporator, then the resulting mixture was freeze-dried to give a powder.

CROP 2B: 540 mL of a solution containing 3.7 g/L of nanoparticles produced according to Example 1, was added dropwise to a solution of 2.15 g pyroxsulam in 2.2 L methanol under constant stirring. The solution was left stirring open in a fume hood to allow the methanol to partially evaporate. An additional 300 mL water was then added, and the solution was partially evaporated by a rotary evaporator. After the evaporation the volume of the solution was about 850 mL, to this volume 150 mL of RO water was added, and the solution was again partially evaporated in a rotary evaporator. When 600 mL of solution remained, evaporation was stopped and the remaining solution was freeze-dried to yield the final product.

Example 7: Formation of a Solid Formulation (WP) of Nanoparticles or Aggregates of Nanoparticles of Polymer-Associated Pyroxsulam Via Freeze Drying from Water with Nanoparticles of p(MAA-Co-EA) [MAA:EA=Approx. 90:10]

A pyroxsulam formulation with a theoretical active ingredient content of 30% by weight was prepared. 2 mg sodium dodecylbenzene sulfonate and 10 mg Reax 88B were dissolved in 15.9 mL of a 6.3 g/L solution of dialyzed nanoparticle solution, (100 mg of nanoparticles total). The nanoparticles were prepared according to Example 1. This aqueous solution was added dropwise to a solution of 100 mg pyroxsulam in 100 mL methanol under constant stirring. The solution was left stirring open in a fume hood to allow the methanol to partially evaporate. An additional 35 mL water was then added, and the remaining methanol was evaporated from the solution by a rotary evaporator. The solution was freeze-dried to yield the final product.

Example 8: Formation of a Solid Formulation (WP) of Nanoparticles or Aggregates of Nanoparticles of Polymer-Associated Pyroxsulam Via Freeze Drying from Water with Nanoparticles of p(MAA-Co-EA) [MAA:EA=Approx. 90:10]

A pyroxsulam formulation with a theoretical active ingredient content of 47% by weight was prepared. 5 mg sodium dodecylbenzene sulfonate and 25 mg Reax 88B, 250 mg of nanoparticles with a MAA:EA ratio of approx. 90:10 prepared according to Example 1, were dissolved in 35 mL of water. The solution was adjusted to a pH of 7 and then filtered through filter paper to remove any insoluble portions. Then aqueous solution was added dropwise to a solution of 250 mg pyroxsulam in 250 mL methanol under constant stirring. The solution was left stirring open in a fume hood to allow the methanol to partially evaporate. 215 mL of additional water was then added. The solution was partially evaporated in a rotary evaporator remove the remaining methanol resulting in a remaining volume of about 200 mL. The solution was freeze-dried to yield the final product, 476 mg of powder.

Example 9: Formation of a Solid Formulation (WP) of Nanoparticles or Aggregates of Nanoparticles of Polymer-Associated Pyroxsulam Via Freeze Drying from Water with Nanoparticles of p(MAA-Co-EA) [MAA:EA=Approx. 60:40]

A pyroxsulam formulation with a theoretical active ingredient content of 47% by weight was prepared. 5 mg sodium dodecylbenzene sulfonate and 25 mg Reax 88B, 250 mg of nanoparticles with a MAA:EA ratio of approx. 60:40 prepared according to Example 1, were dissolved in 35 mL of water. The pH of the solution was adjusted to 6.5 to dissolve the polymer. This aqueous solution was added dropwise to a solution of 250 mg pyroxsulam in 250 mL methanol under constant stirring. The solution was left stirring open in a fume hood to allow the methanol to partially evaporate. 215 mL of additional water was then added. The solution was partially evaporated in a rotary evaporator remove the remaining methanol resulting in a remaining volume of about 200 mL. The solution was freeze-dried to yield the final product, 483 mg of powder.

Example 10: Formation of a Solid Formulation (WP) of Nanoparticles or Aggregates of Nanoparticles of Polymer-Associated Pyroxsulam Via Freeze Drying from Water with Nanoparticles of p(MAA-Co-EA) [MAA:EA=Approx. 90:10]

A pyroxsulam formulation with a theoretical active ingredient content of 48% by weight was prepared. 7.5 mg Geropon T-77 and 7.5 mg Morwet D-425, 250 mg of nanoparticles with a MAA:EA ratio of approx. 90:10 prepared according to Example 1, were dissolved in 35 mL of water. This aqueous solution was added dropwise to a solution of 250 mg pyroxsulam in 250 mL methanol under constant stirring. The pH of the solution was adjusted to 7 to fully dissolve the polymer, and then filtered through filter paper to remove any insoluble portion. The solution was left stirring open in a fume hood to allow the methanol to partially evaporate. 215 mL of additional water was then added. The solution was partially evaporated in a rotary evaporator remove the remaining methanol resulting in a remaining volume of about 200 mL. The solution was freeze-dried to yield the final product, 473 mg of powder.

Example 11: Formation of a Solid Formulation (WP) of Nanoparticles or Aggregates of Nanoparticles of Polymer-Associated Pyroxsulam Via Freeze Drying from Water with Nanoparticles of p(MAA-Co-EA) [MAA:EA=Approx. 60:40]

A pyroxsulam formulation with a theoretical active ingredient content of 48% by weight was prepared. 7.5 mg Geropon T-77 and 7.5 mg Morwet D-425, 250 mg of nanoparticles with a MAA:EA ratio of approx. 60:40 prepared according to Example 1, were dissolved in 35 mL of water. This aqueous solution was added dropwise to a solution of 250 mg pyroxsulam in 250 mL methanol under constant stirring. The pH of the solution was adjusted to 6.5 to fully dissolve the polymer. The solution was left stirring open in a fume hood to allow the methanol to partially evaporate. 215 mL of additional water was then added. The solution was partially evaporated in a rotary evaporator remove the remaining methanol resulting in a remaining volume of about 200 mL. The solution was freeze-dried to yield the final product, 377 mg of powder.

Example 12: Formation of a Solid Formulation (WP) of Nanoparticles or Aggregates of Nanoparticles of Polymer-Associated Pyroxsulam Via Freeze Drying from Water with Nanoparticles of p(MAA-Co-EA) [MAA:EA=Approx. 90:10]

A pyroxsulam formulation with a theoretical active ingredient content of 48% by weight was prepared. 7.5 mg Reax 88B, 250 mg of nanoparticles with a MAA:EA ratio of approx. 90:10 prepared according to Example 1, were dissolved in 35 mL of water. This aqueous solution was added dropwise to a solution of 250 mg pyroxsulam in 250 mL methanol with 12.5 mg of Activator 90 (a non-ionic surfactant) under constant stirring. The solution was left stirring open in a fume hood to allow the methanol to partially evaporate. 215 mL of additional water was then added. The solution was partially evaporated in a rotary evaporator remove the remaining methanol resulting in a remaining volume of about 200 mL. The solution was freeze-dried to yield the final product, 471 mg of powder.

Example 13: Formation of a Solid Formulation of Nanoparticles or Aggregates of Nanoparticles of Polymer-Associated Pyroxsulam Via Spray Drying Directly from Water with Nanoparticles of p(MAA-Co-EA) [MAA:EA=Approx. 90:10]

A pyroxsulam formulation with a theoretical active ingredient content of 22.5% by weight was prepared. 4 batches were prepared as follows. 11.25 g of polymer nanoparticles derived from p(MAA-co-EA) (MAA:EA=approx. 90:10) prepared according to the procedure outlined in Example 1, dispersed with 3.75 g pyroxsulam in 1.675 L of RO water and stirred overnight. The pH of the solution was adjusted to 7. The solution of was then spray dried with an inlet temperature of 150° C. and an outlet temperature of 90° C., atomizing gas flow rate of 10 L/min, feed rate of about 10.5 mL/min (varied from a minimum of 5.5 mL/min to a maximum of 15 mL/min) and aspirator air flow of 730 L/min. The product was recovered as a powder. The four batches of powder were mixed. 45 g of the mixed batch powder were mixed with 2.5 g Reax 88B, 1.5 g polyvinyl alcohol and 0.5 g of sodium dodecylbenzene sulfonate in an IKA analytical mill.

Example 14: Formation of a Solid Formulation of Nanoparticles or Aggregates of Nanoparticles of Polymer-Associated Pyroxsulam Via Spray Drying Directly from Water with Nanoparticles of p(MAA-Co-EA) [MAA:EA=Approx. 90:10]

Six batches of a solid formulation of nanoparticles or aggregates of nanoparticles of polyer-associated pyroxsulam were prepared by spray draying as follows: 9 g of polymer nanoparticles derived from p(MAA-co-EA) (MAA:EA=approx. 90:10) were prepared according to the procedure outlined in Example 1, dispersed with 3 g pyroxsulam in 2 L of RO water and stirred for 2 hours. The pH of the solution was adjusted to 6.7. The solution of was then spray dried with an inlet temperature of 115° C., outlet temperature starting at 60° C. and decreased to 50° C. (The temperature was decreased after power product was first produced. The lower outlet temperature was used for subsequent batches) Atomizing air flow rate of 10 L/min, feed rate of 17.5 mL/min (constant) and aspirator air flow of 730 L/min. The product was recovered as a powder with a moisture content of 14.1%. The six batches of powder were mixed. 61.32 g of the mixed batch powder was further mixed with 3.41 g of Reax 88B, 2.73 g of polyvinyl alcohol and 0.68 g of sodium dodecylbenzene sulfonate in an IKA analytical mill. The mixture was assayed to contain 12.7% water, 19.3% pyroxsulam, 5% Reax 88B, 4% polyvinyl alcohol, 1% SDBS and 58.0% polymer nanoparticles. The resulting formulation was then dried at 40° C. in a vacuum oven for 6 days, until the total moisture was about 5%, giving a final theoretical active ingredient content of 21% by weight.

Formulation Testing

Example 15: Comparison of a Commercially Available Herbicide Formulation with Nano-Formulation of the Same Herbicide General Materials and Methods (Plant Preparation and Herbicide Application)

Green foxtail (*Setaria viridis*), volunteer corn (*Zea mays*) and common oat seedlings were grown in pots containing a commercial peat mixture, Promix PGX (Premier Brands, Brampton, Canada. Plants were grown in a controlled environment growth room maintained at 25/20±1° C. day/night temperature, 16-h photoperiod and an average relative humidity of 75%. Light intensity was constant at 200 $\mu m^{-2} s^{-1}$. Plants were grown as a single plant per pot (450 ml), and watered daily with water-soluble fertilizer (20% N, 20% $P_2O_5$, 20% $K_2O$ and micronutrients, 0.25 g/l) to promote optimal growth. Green foxtail, corn and oat seedlings at the $3^{rd}$ expanded leaf stage were used for all dose-response studies. Plants were sprayed with a track sprayer (Mandel Scientific Crop., Guelph, Canada) equipped with a single 8002E flat-fan nozzle, mounted 45 cm above the top of the plant canopy, set to deliver 210 L $ha^{-1}$ at 276 KPa.

At approximately 14 days after treatment (DAT), shoots were clipped at the soil surface. All plant material was oven dried at 80° C. to a constant weight. Green foxtail, corn and oat biomass data were expressed as the percentage of the untreated control. Dose-response curves were generated using the method describe by Seefeldt et al. (Weed Tech. 1995). This method utilizes a log-logistic curve with four parameters (y=c+{d−c}/1+exp[b(log x−log $GR_{50}$)]), where $GR_{50}$ is the dose providing 50% growth reduction, the upper limit is d, the lower limit is c, and parameter b denotes the relative slope around the $GR_{50}$.

Experiments 6a and 6b. Determining the Dose of the Standard Formulation of Fenoxaprop-p-Ethyl Required to Reduce Green Foxtail, Corn and Oat Seedling Growth by 50% ($GR_{50}$) Under Controlled Environment Conditions Previous experience has shown that weeds are generally more sensitive to herbicides when grown in growth-room conditions that provide relatively high moisture, fertility and moderate temperature and light compared to field conditions. It was expected that the $GR_{50}$ dose for control of green foxtail, corn and oat seedlings grown under controlled environment conditions would likely be significantly lower than the label dose of 54 g ai/ha. Therefore, the objective of the first trial determined the $GR_{50}$ dose for green foxtail, corn and oat for the standard commercial formulation of fenoxaprop-p-ethyl (Excel Super) under growth room conditions.

Estimated $GR_{50}$ doses of 3 g ai/ha for green foxtail (Heap and Morrison, 1996) and 58.5 g ai/ha for oat (Lefsrud and Hall, 1989) were used as the basis for the initial dose ranges for these species. This experiment was established as a completely randomized design with five replications and was conducted twice over time (experiments 6a and 6b), approximately 2 weeks apart which allowed for dose modification as required. The initial dose range of the standard formulation of fenoxaprop-p-ethyl was 0, 1, 2, 4, 6, 8 and 12 g ai/ha for green foxtail; 0, 5, 10, 15, 20, 25, and 30 g ai/ha for corn; and 0, 20, 40, 60, 80, 100 and 120 g ai/ha for oat. Results of this experiment are presented in Appendix 1a. The experiment was repeated and refined using $GR_{50}$ doses of 3.0, 6.0 and 30.0 g ai/ha of the standard formulation of fenoxaprop-P-ethyl for green foxtail, corn and oat, respectively and applied at 0, 0.4, 0.6, 0.8, 1.0, 1.2, 1.4, 1.6 and 2.0× the $GR_{50}$ dose. Results of this experiment are presented in Appendix 1b.

Experiment 6c. To Determine the Dose of the Standard and Nano Formulations of Fenoxaprop-p-Ethyl Required to Reduce Green Foxtail, Corn and Oat Seedling Growth by 50% ($GR_{50}$) Under Controlled Environment Conditions Estimated $GR_{50}$ doses of the standard fenoxaprop-p-ethyl formulation for green foxtail, corn and oat determined previously in experiments (6a, b) were used as the basis for the dose ranges to compare the efficacy of standard and nano-formulations of fenoxaprop-P-ethyl. The experiment was conducted using $GR_{50}$ doses of 3.0, 6.0 and 25.0 g ai/ha of the standard and nano-formulations of fenoxaprop-p-ethyl for green foxtail, corn and oat, respectively. Both formulations were applied at 0, 0.4, 0.6, 0.8, 1.0, 1.2, 1.4, 1.6 and 2.0× the $GR_{50}$ dose. Non-ionic surfactant (Agral 90) at 0.25% volume/spray volume was included with all treatments of the nano-formulation of fenoxaprop-P-ethyl. The experiment was established as a completely randomized design with five replications and was conducted twice over time (experiments 2a and 2b). Experimental conditions and procedures were similar to those previously described. Standard and nano-formulations of fenoxaprop-P-ethyl were applied when green foxtail, corn and oat seedlings were at the 3$^{rd}$ expanded leaf stage.

Results

The nanoformulation of fenoxaprop-P-ethyl had greater efficacy consistently on green foxtail and corn than the standard formulation in both experimental runs. For green foxtail and corn, the $GR_{50}$ dose and average plant biomass was reduced by ~50% with the nano-formulation compared to the standard formulation of fenoxaprop-P-ethyl.

Figure 2:
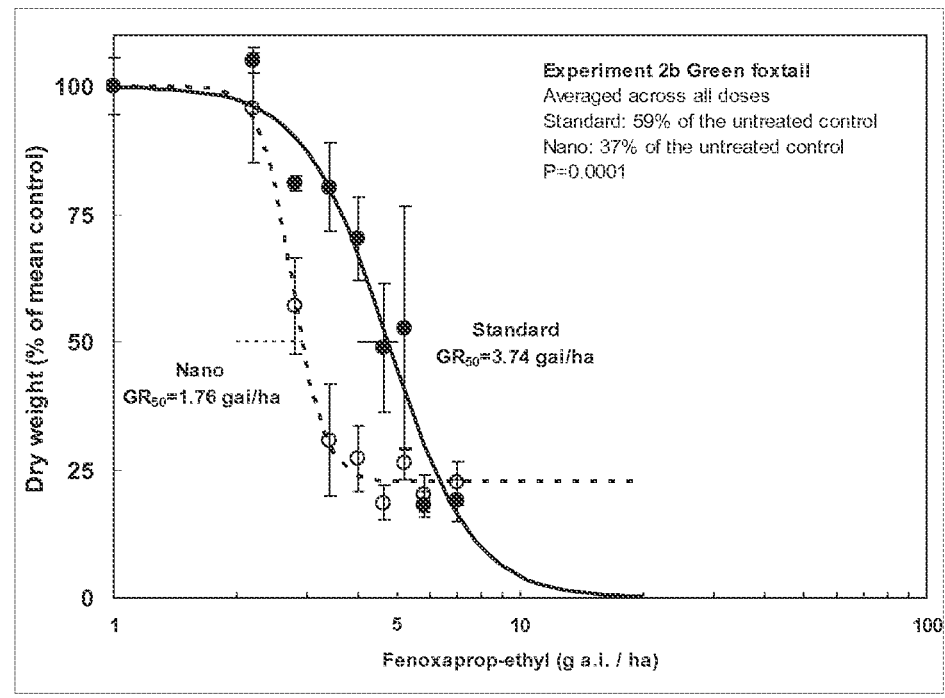
Figure 7:
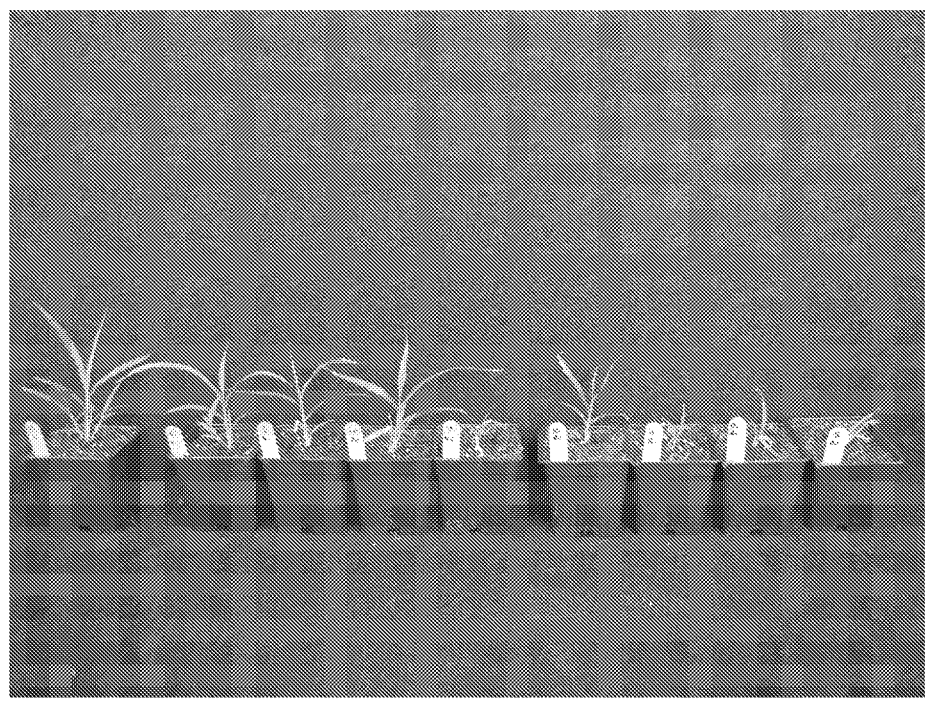
FIG. 7: Green foxtail plants treated with a commercial formulation of fenoxaprop-P-ethyl (Excel® Super EC; 80.5 g ai/L) and WP formulation of fenoxaprop-P-ethyl prepared according to the present invention. Pot 1: untreated green foxtail control. Pots 2-5: green foxtail plants inoculated with the commercial formulation at doses of 1.8, 2.4, 3.0 and 4.8 g ai/ha (left to right). Pots 6-9: green foxtail plants inoculated with a formulation prepared according to the present invention at doses of 1.8, 2.4, 3.0 and 4.8 g ai/ha (left to right).

For green foxtail the nano-formulation had a $GR_{50}$ dose of 1.49 and 1.76 g ai/ha compared to 3.38 and 3.74 g a.i./ha for the standard formulation, in the two runs of the experiment, respectively (FIGS. 1 & 2). Similarly, green foxtail biomass was 18% and 37% of the untreated with the nano-formulation averaged across all doses, compared to 52%% and 59% with the standard formulation. Green foxtail plants inoculated with the commercial formulation and the nano-formulation of the present invention at various doses of fenoxaprop-P-ethyl are shown in FIG. 7 (see figure description for rates).

Figure 3:
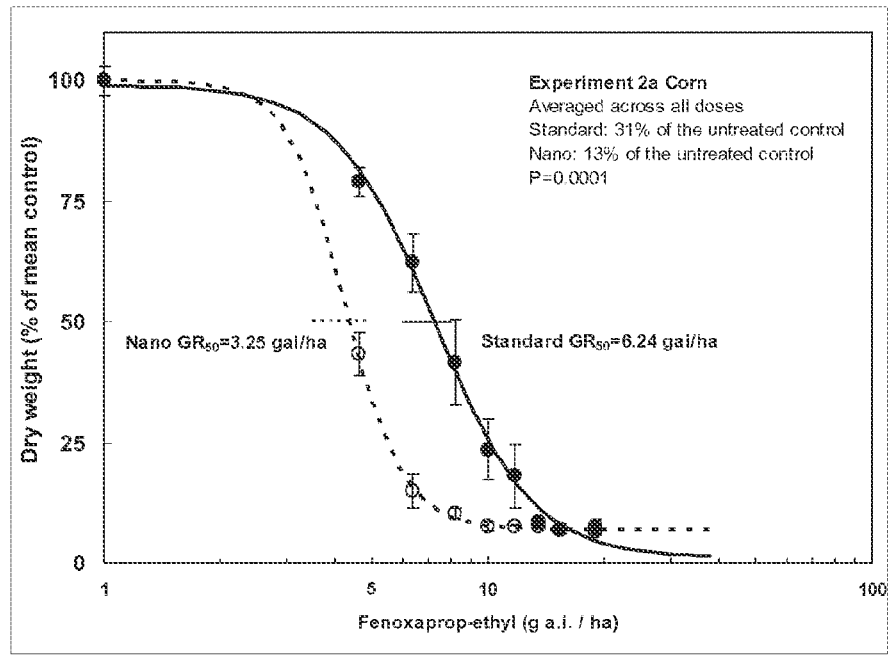
FIGS. 3 (upper) & 4 (lower): Dose response and $GR_{50}$ (50% growth reduction) of corn with standard and nano-formulations of fenoxaprop-P-ethyl. Averaged across all herbicide doses the standard and nano-formulations reduced dry wt. of corn to 31 and 13% of the untreated control, respectively in FIG. 3, and 33 and 17%, respectively in FIG. 4.
Figure 4:
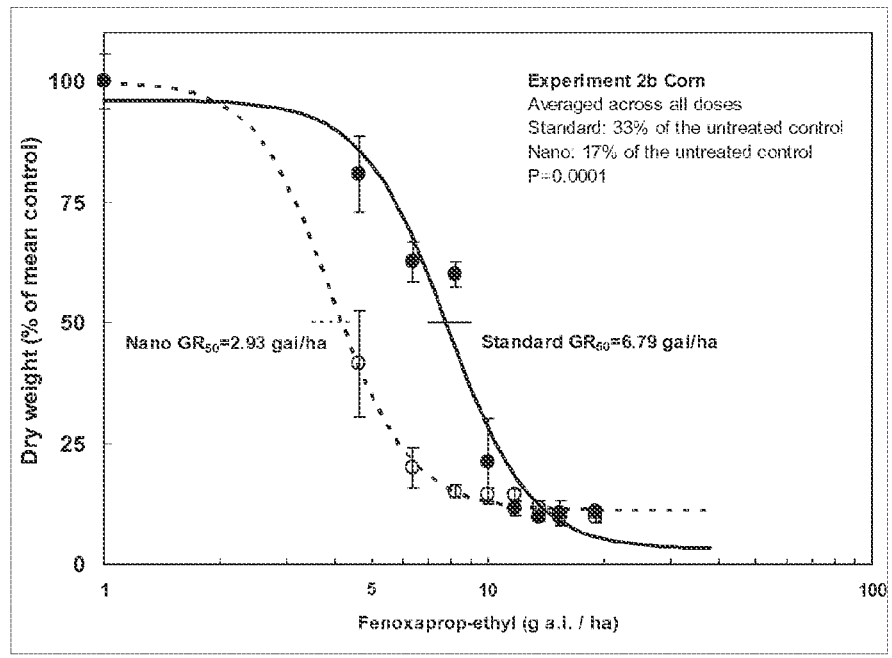
Figure 8:
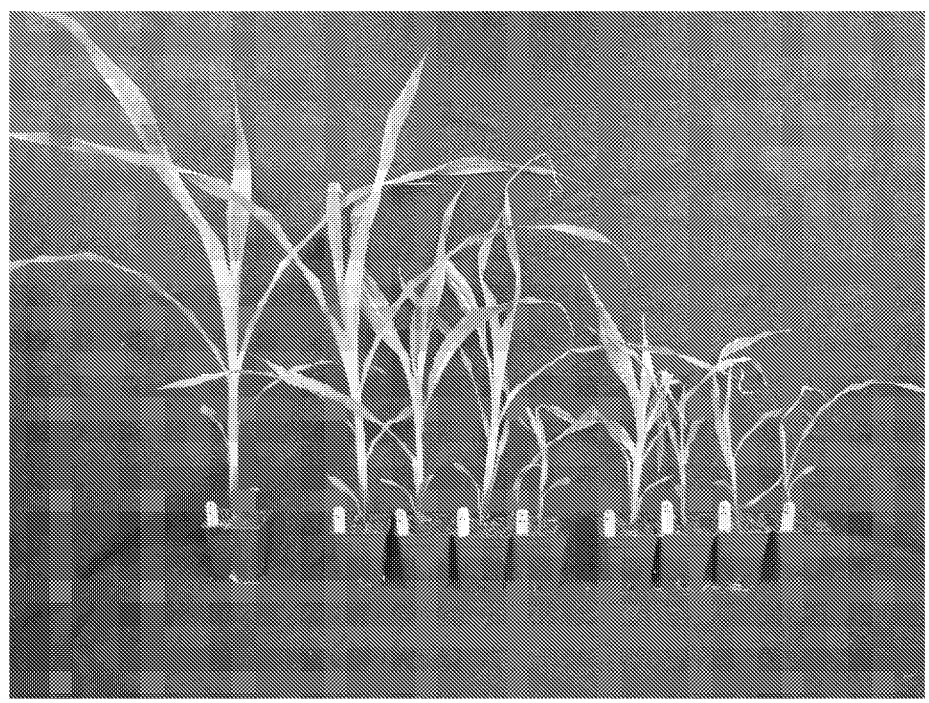
FIG. 8: Volunteer Corn plants treated with a commercial formulation of fenoxaprop-P-ethyl (Excel® Super EC; 80.5 g ai/L) and WP formulation of fenoxaprop-P-ethyl prepared according to the present invention. Pot 1: untreated volunteer corn control. Pots 2-5: volunteer corn plants inoculated with the commercial formulation at doses of 3.6, 5, 4, 7.2 and 9 g ai/ha (left to right). Pots 6-9: volunteer corn plants inoculated with the commercial formulation at increasing doses of doses of 3.6, 5.4, 7.2 and 9 g ai/ha (left to right).

For corn the nano-formulation had a $GR_{50}$ dose of 3.25 and 2.93 g ai/ha compared to 6.24 and 6.79 g ai/ha for the standard formulation, in the two runs of the experiment, respectively (FIGS. 3 & 4). Similarly, corn biomass was 13% and 17% of the untreated control with the nano-formulation averaged across all doses, compared to 31% and 33% with the standard formulation. Corn plants inoculated with the commercial formulation and the nano-formulation of the present invention at various doses of fenoxaprop-P-ethyl are shown in FIG. 8 (see the figure description for rates).

Figure 5:
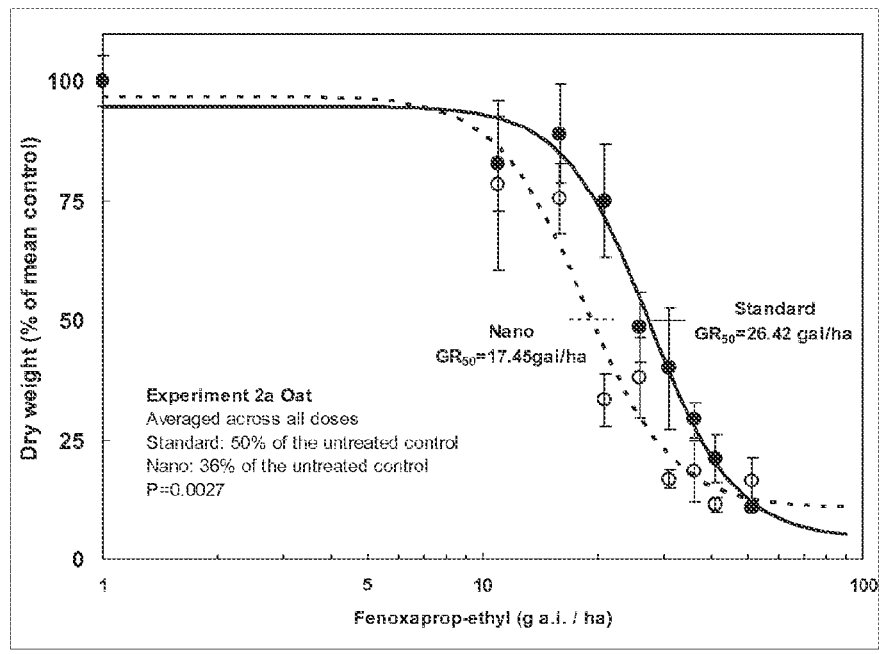
FIGS. 5 (upper), 6 (lower): Dose response and $GR_{50}$ (50% growth reduction) of oat with standard and nano-formulations of fenoxaprop-P-ethyl. Averaged across all herbicide doses the standard and nano-formulations reduced dry wt. of oat to 50 and 36% of the untreated control, respectively in FIG. 5, and 38 and 42%, respectively in FIG. 6.
Figure 6:
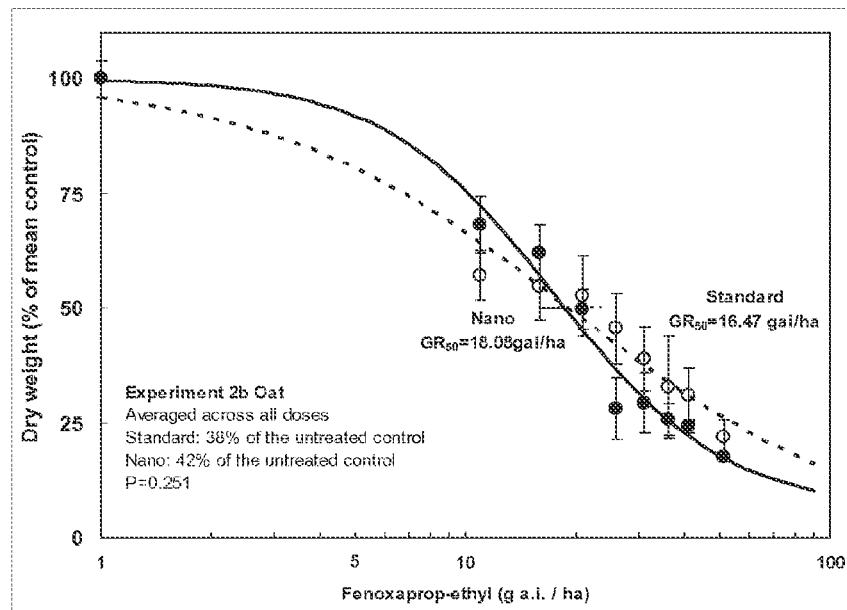
Figure 9:
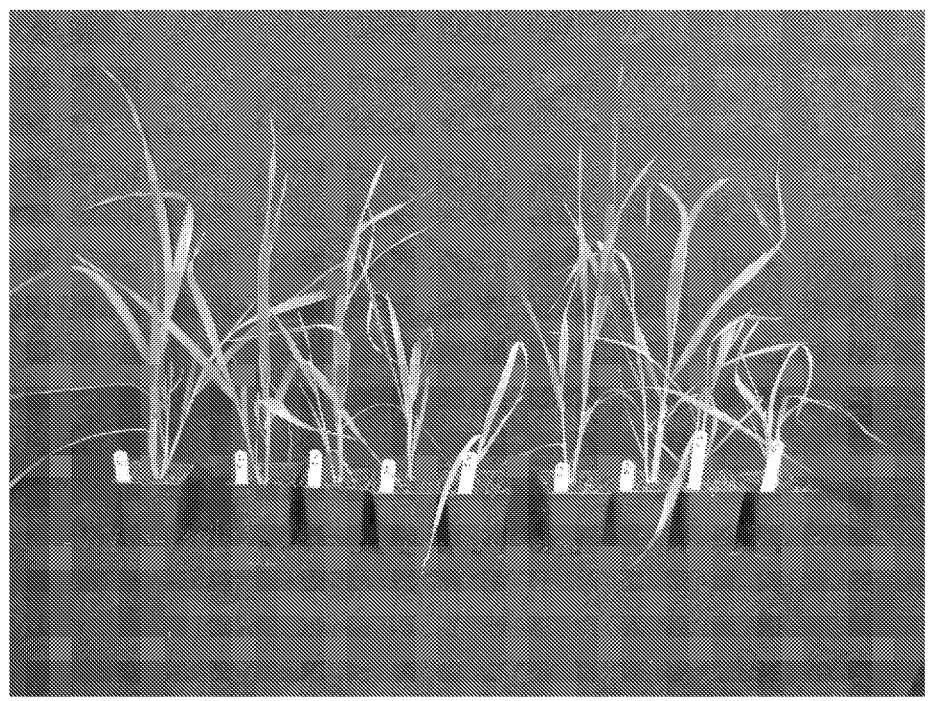
FIG. 9: Common oat treated with a commercial formulation of fenoxaprop-P-ethyl (Excel® Super EC; 80.5 g ai/L) and WP formulation of fenoxaprop-P-ethyl prepared according to the present invention. Pot 1: untreated wild oat control. Pots 2-5: common oat inoculated with the commercial formulation at doses of 15, 25, 35 and 50 g ai/ha (left to right). Pots 6-9: green foxtail plants inoculated with a formulation prepared according to the present invention at doses of 15, 25, 35 and 50 g ai/ha (left to right).

Oat exhibited greater tolerance to fenoxaprop-p-ethyl and results were not consistent across the two runs of the experiment. In the first run, the nano-formulation had greater efficacy than the standard formulation but in the second run both formulations had similar efficacy. In the first run, the nano-formulation had a $GR_{50}$ dose of 17.45 g ai/ha, compared to 26.42 g ai/ha with standard formulation and oat biomass was 36% of the untreated with the nano-formulation averaged across all doses, compared to 50% with the standard formulation (FIGS. 5 & 6). In the second run of the experiment, the nano-formulation had a $GR_{50}$ dose of 18.08 g ai/ha, which was similar to the first run. However, the standard formulation had a $GR_{50}$ dose of 16.47 g ai/ha, which was less than in the first run. The reason for the improved efficacy of the standard formulation in the second run of the experiment on oats may be attributed to genetic variability in tolerance to fenoxaprop-P-ethyl. Further research is required to evaluate the efficacy of the nano formulation of fenoxaprop-P-ethyl under field conditions. Oat plants inoculated with the commercial formulation and the nano-formulation of the present invention at various doses of fenoxaprop-P-ethyl are shown in FIG. 9 (see the figure description for rates).

In sum, the nano-formulations of fenoxaprop-p-ethyl demonstrated greater efficacy consistently on green foxtail and corn than the standard formulations. For green foxtail and corn, the dose required of the nano-formulation to reduce plant biomass by 50% (GR50) was approximately 50% of the commercial formulation of fenoxaprop-p-ethyl. In addition, the nano-formulated fenoxaprop-p-methyl was equal to or better for the control of the more tolerant oat species compared to the standard commercial formulation.

Example 16: Qualitative Analysis of Formulation-Dependent Hydrolysis of WP Formulations of Fenoxaprop-P-Ethyl Prepared Via Spray Drying Various WP formulations of fenoxaprop-P-ethyl were prepared via spray drying according to the procedures outlined in Example 2-Example 4. After spray drying, hydrolysis of fenoxaprop-P-ethyl was analyzed via TLC (thin layer chromatography). For each of the WP formulations, 10 mg of the collected powder was dispersed in 1 mL of technical grade acetonitrile and sonicated for 5 minutes. The sample was then spotted on a TLC plate to check for the presence of hydrolysis products (mobile phase: 80% hexanes/20% ethyl acetate). The results of the analyses are presented in the table, below.

TABLE 10

TLC analysis of fenoxaprop-P-ethyl hydrolysis
in spray dried formulations

| Pre-formed Nanoparticle Composition | Result | Notes |
|---|---|---|
| p(MAA-co-EA) (MAA:EA = 90:10) | Hydrolysis product observed by TLC | Powder formulation contains mefenpyr-diethyl safener |
| p(MAA-co-EA) (MAA:EA = 90:10) | Hydrolysis product observed by TLC | |
| p(MAA-co-EA) (MAA:EA = 75:25) | Hydrolysis product observed by TLC | |

Example 17: Qualitative Analysis of Polymer-Dependent Hydrolysis of WP Formulations of Fenoxaprop-P-Ethyl Prepared Via Ball Milling Various WP formulations of fenoxaprop-P-ethyl were prepared via ball milling according to the procedure outlined in Example 5 with nanoparticles derived from different polymers. The nanoparticles were prepared according to procedure analogous described in Example 1. Immediately after formulation, hydrolysis of fenoxaprop-P-ethyl was analyzed via TLC (thin layer chromatography). For each of the WP formulations, 10 mg of the collected powder was dispersed in 1 mL of technical grade acetonitrile and sonicated for 5 minutes. The sample was then spotted on a TLC plate to check for the presence of hydrolysis products (mobile phase: 80% hexanes/20% ethyl acetate). The results of the analyses are presented in the table, below.

TABLE 11

TLC analysis of fenoxaprop-P-ethyl hydrolysis
in ball-milled formulations

| ntry | Pre-formed Nanoparticle Composition | Result |
|---|---|---|
| | PAA | No hydrolysis product observed by TLC |
| | p(MAA-co-EA) (MAA:EA = 90:10) | No hydrolysis product observed by TLC |
| | p(MAA-co-EA) (MAA:EA = 75:25) | No hydrolysis product observed by TLC |
| | p(MAA-co-styrene) (MAA:styrene = 75:25) | Hydrolysis product observed by TLC |
| | poly(methacrylic acid-co-butyl methacrylate) | Hydrolysis product observed by TLC |
| | p(MAA-co-BUMA) (MAA:BUMA = 75:25) | |

Example 18: Increasing Resistance to Hydrolysis Fenoxaprop-P-Ethyl Formulated According to the Present Invention The stability of a formulation of nanoparticles or aggregates of nanoparticles of polymer associated fenoxaprop-P-ethyl is compared to a commercial formulation of the same active ingredient. A formulation of fenoxaprop-P-ethyl is prepared according to Example 2 and dispersed in water and the medium is adjusted to pH 9. Similarly, the commercial formulation is diluted with water to obtain a dispersion of the same concentration and adjusted to the same pH. The hydrolysis of fenoxaprop-P-ethyl for both formulations is monitored and quantified using the procedures outlined in OECD Guidelines for the Testing of Chemicals 111: Hydrolysis as a Function of pH, or modifications of these procedures.

Example 19: Increasing Resistance to Photolysis of a CHD Formulated According to the Present Invention The stability of a formulation of nanoparticles or aggregates of nanoparticles of polymer associated CHD is compared to a commercial formulation of the same active ingredient. A formulation of CHD is prepared according to the current invention. The nanoparticles are dispersed in water to produce a dispersion that is 2 mg/mL in active ingredient. Similarly, the commercial formulation is diluted with water to obtain a solution that is 2 mg/mL in CHD. A solution containing surfactant and technical grade CHD is also prepared at the same active ingredient concentration (2 mg/mL). The aqueous photolysis of the CHD is investigated using the procedures outlined in the "OECD Guidelines for the Testing of Chemicals 316: Phototransformation of Chemicals in Water—Direct Photolysis" or modifications of these procedures.

Example 20: Increasing Resistance to Photolysis of a CHD Formulated According to the Present Invention (TLC Analysis)

The stability of a formulation of nanoparticles or aggregates of nanoparticles of polymer associated CHD is compared to a commercial formulation of the same active ingredient. A formulation of CHD is prepared according to the current invention. The nanoparticles are dispersed in water to produce a dispersion that is 2 mg/mL in CHD. Similarly, the commercial formulation is diluted with water to obtain a solution that is 2 mg/mL in CHD. A solution containing surfactant and technical grade CHD is also prepared at the same active ingredient concentration (2 mg/mL). A thin film of each solution is then cast on a microscope slide, and is exposed to a solar simulator (Fade Test UV simulator, model 16S-300-003; Solar Light Co, Glenside, Pa. USA) for different periods of time (5 mins-240 mins). The amount of non-photo degraded CHD is assayed by extracting the active from the thin film after exposure using thin layer chromatography (TLC) to determine the extent of photo degradation.

Additional Formulations, Dissolution and Biological Tests

Example 21: Preparation of a HSLS Formulation of Nanoparticles of Polymer-Associated Fenoxaprop-P-Ethyl 2 g of a solid formulation of fenoxaprop-P-ethyl is prepared according to the procedure outlined in Example 2. In a 20 mL vial, this solid is then dispersed in 7 mL water containing: mg of Reax88B dispersant; 33 mg sodium dodecylbenzene sulfonate; 165 mg of glycerol, mg of xanthan gum (from a 0.1 weight % solution in water) and 1.9 mg 1,2-benzisothiazalin-3-one preservative (Proxel GXL, Arch Chemicals, Inc.). The solution is mixed well with a stir bar. The HSLS formulation is stable over a period of 2 weeks at 55° C., showing no visible formation of crystallites or caking. If settling occurred, the solution is agitated to restore its initial consistency.

Example 22: Preparation of a Wettable Granule (WG) Formulation from a Solid Formulation of Nanoparticles of Polymer-Associated Herbicide Approximately 20 g of a solid formulation of herbicide is prepared according to the procedure outlined in Example 2 for the preparation of a solid formulation of fenoxaprop-P-ethyl. In a beaker, 17.6 g of lactose, 2 g of Reax88B, and 400 mg of sodium dodecylbenzene sulfonate is added along with 10-12 g of water. The mixture is stirred very well and heated slightly (~60° C.) to fully disperse all of the solids. Once the solids disperse, the resulting solution is allowed to cool to room temperature. The solid formulation of herbicide is then immediately added to the cooled water solution containing the filler, dispersant and wetter. The resulting slurry is mixed very well with a spatula until the mixture had a dough-like consistency. The dough-like mixture is then extruded into strips though the orifice of a disposable hypodermic syringe. The strips are allowed to dry for approximately 1 hour and are then cut into small 2-5 mm granules. The WG formulation had minimal dustiness and is stable to several freeze thaw cycles (−5° C. to 30° C.) No phase separation of the active ingredient occurs after several temperature cycles between 25° C. and 54° C.

Example 23: Improved Foliar Uptake of Herbicide in Formulations Prepared According to the Current Invention Separate plants are treated with either an herbicide formulation prepared according to the current invention, or a commercially available formulation of the same active ingredient at the same rate of active ingredient. After a certain amount of time, the samples are collected, and the foliar uptake of the herbicide from each of the formulations is assessed by washing the samples with solvent and quantifying the amount of herbicide residue in the washings and in the plant.

Example 24: High-Salt Stability/Compatibility of Herbicide Formulations Prepared According to the Current Invention An herbicide formulation prepared according to the current invention is dispersed in tap water. To this of a high salt, concentrated fertilizer (10-34-0 fertilizer at 11.7 lb/gal (sp gr 1.403 g/L) is added. A milky dispersion formed immediately after mixing, and no settling of flocs is observed within a three hour period. A commercially available WP or SC formulation of the same herbicide is dispersed in the same amount of tap water is also mixed with the same amount of the high salt, concentrated fertilizer composition. A milky dispersion formed and settling of flocs is observed within 10 minutes.

Example 25: Formation of a Solid Formulation of Nanoparticles or Aggregates of Nanoparticles of Polymer-Associated Herbicide from an Aqueous Dispersion Containing Phosphate Buffered Saline (PBS)

Polymer nanoparticles derived from poly(methacrylic acid (MAA)-co-ethyl acrylate(EA)) (MAA:EA=90:10) are prepared according to the procedure outlined in Example 1. The solid is dispersed in technical 15 mL of grade methanol in a glass beaker until a clear dispersion is formed, and is then filtered through coarse filter paper to remove any undispersed solids. 300 mg of herbicide is then added to the filtered dispersion. The resulting solution is clear, and is stirred at 500 rpm using a magnetic stir bar on a stirred hot plate for one hour. 1 L of PBS buffer (Invitrogen, 1×, pH 7.4 which contains: 137 mM NaCl; 2.7 mM KCl; 10 mM $Na_2HPO_4$; 2 mM $KH_2PO_4$) is then placed in a 2 L glass beaker and is stirred at 500 rpm using an overhead mixer. The methanol dispersion containing the nanoparticles and herbicide is then slowly fed into the stirred buffer at a rate of ~1-2 mL/min using a peristaltic pump. The feeding tube is submerged under the buffer during the entire addition process. After all the methanol had been added, the resulting milky solution is left to mix for another 20 mins. The solution is then concentrated by removing water/solvent using a rotary evaporator to about ½ its initial volume. The concentrated dispersion is then freeze dried to obtain a solid formulation of herbicide. The solid is redispersible in water at a concentration of ~200 ppm active ingredient. A volume average particles size is measured by DLS for the solid re-dispersed in deionized water at 400 ppm total solids.

Example 26: High-Salt Stability/Compatibility of an Herbicide Formulation Prepared According to the Current Invention The compatibility/dispersibility of an herbicide formulation prepared according to the current invention is tested in CIPAC (Collaborative International Pesticides Analytical Council) standard water G (8000 ppm hardness, pH 7.0-7.0, $Mg^{2+}$ only). CIPAC standard water G is prepared according to MT 18 in CIPAC handbook F, p 59. To prepare a 200 ppm herbicide dispersion, 8-10 mg of a solid formulation prepared according to the current invention is placed in a 20 mL scintillation vial. To this, 20 mL of CIPAC standard water G is added. After the addition of liquid, the solid formulation is allowed to wet for a few minutes, and the vial is then covered and tipped 20 times to fully disperse the formulation. A milky dispersion is formed immediately after mixing, and no settling of flocs is observed over a three hour period. Dispersion, Greenhouse and Field Trials with Pyroxsulam Example 27: Evaluation of Dissolution/Dispersion Properties of Formulation of Example 6

Figure 10:
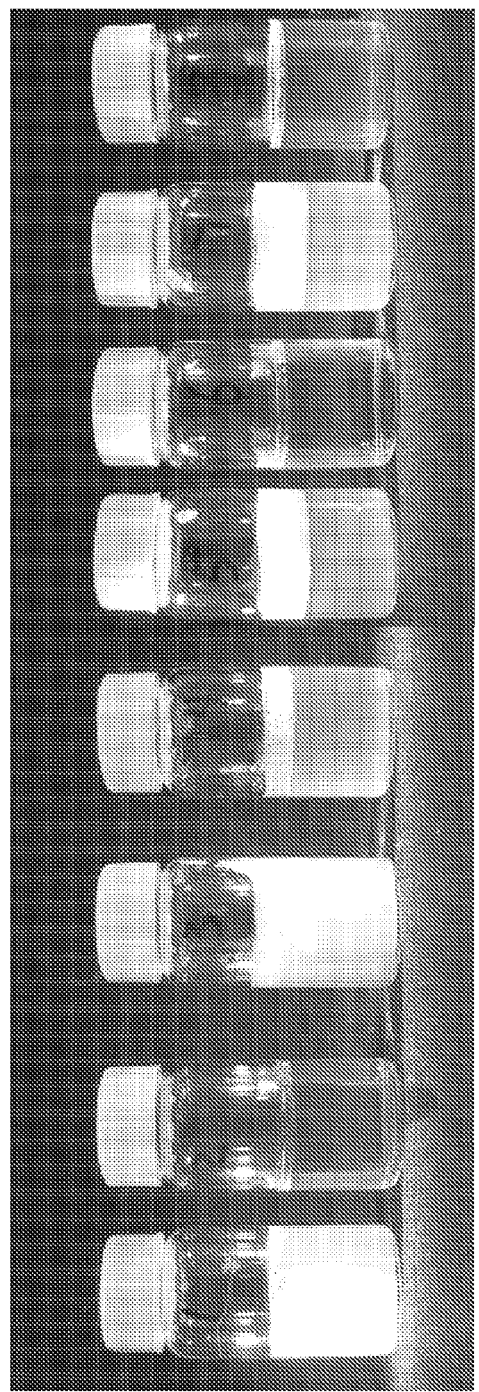
FIG. 10 is a photograph of diluted samples of the formulation prepared in Example 6. Two samples of the formulation were each diluted to 1 wt. % and 0.1 wt. % of active ingredient in both deionized water and CIPAC-D water with a hardness of 342 ppm.

The formulation prepared according to Example 6 was dispersed in deionized water ("DI") and CIPAC D water with a hardness of 342. The formulations were diluted to concentrations of 1.0 wt. % and 0.1 wt. % active ingredient. Two samples of the formulation of Example 6 were used. The first sample, labeled Crop 2A (as noted in FIG. 10) was assayed to contain 43 wt. % active ingredient, the second sample, label Crop 2B was assayed to contain 26.2 wt. % active ingredient.

Particle size measurements of each sample, diluted to 0.1 g a.i./L were taken. Measurements were taken immediately after the dilution sample was prepared (i.e., Fresh) and 3 hours after dilution was prepared. The particle size measurements are presented in the Tables below:

TABLE 12

Particle size measures for sample 2A diluted to 0.1 g a.i./L

| Crop 2A - Fresh - DI Water | | | Crop 2A - 3 hrs - DI Water | | |
| --- | --- | --- | --- | --- | --- |
| Peak | Diameter (nm) | % mass | Peak | Diameter (nm) | % mass |
| 1 | 22.0 | 6.3 | 1 | 15 | 1.7 |
| 2 | 112.0 | 7 | 2 | 89.4 | 1.3 |
| 3 | 3474.0 | 86.7 | 3 | 1505 | 7.4 |
| | | | 4 | 16440 | 89.6 |

| Crop 2A - Fresh - 342 ppm | | | Crop 2A - 3 hrs - 342 ppm | | |
| --- | --- | --- | --- | --- | --- |
| Peak | Diameter (nm) | % mass | Peak | Diameter (nm) | % mass |
| 1 | 13.8 | 3.3 | 1 | 13.6 | 1 |
| 2 | 246.2 | 4.8 | 2 | 271.4 | 3.2 |
| 3 | 5397 | 92 | 3 | 8708 | 95.8 |

TABLE 13

Particle size measures for sample 2B diluted to 0.1 g a.i./L

| Crop 2B - Fresh - DI Water | | | Crop 2B - 3 hrs - DI Water | | |
| --- | --- | --- | --- | --- | --- |
| Peak | Diameter (nm) | % mass | Peak | Diameter (nm) | % mass |
| 1 | 10.6 | 7 | 1 | 8.4 | 9.3 |
| 2 | 116 | 10.5 | 2 | 161.1 | 8.5 |
| 3 | 3408 | 82.5 | 3 | 7710 | 82.2 |

| Crop 2B - Fresh - 342 ppm | | | Crop 2B - 3 hrs - 342 ppm | | |
| --- | --- | --- | --- | --- | --- |
| Peak | Diameter (nm) | % mass | Peak | Diameter (nm) | % mass |
| 1 | 9.3 | 19.2 | 1 | 15.8 | 9.2 |
| 2 | 125.5 | 5.8 | 2 | 279.2 | 4.1 |
| 3 | 4337 | 75 | 3 | 12283 | 86.7 |

The particle size measurements indicate some particle growth after 3 hours, and larger particle size when CIPAC D water was used for dilution, although particle size appears more stable in CIPAC D water.

Example 28: Evaluation of Dissolution/Dispersion Properties of Formulation of Example 7

Figure 11:
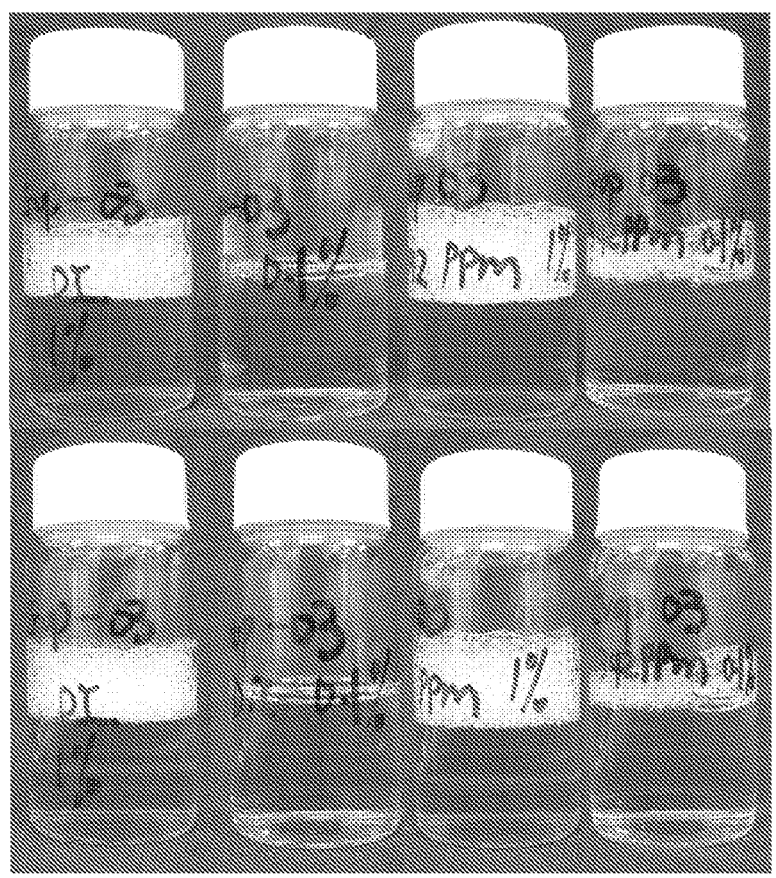
FIG. 11 is a photograph of diluted sample of the formulation prepared in Example 7. The formulation was diluted to 1 wt. % and 0.1 wt. % of active ingredient in both deionized water and CIPAC-D water with a hardness of 342 ppm. The dilutions were performed in duplicate.

A sample of the formulation prepared according to Example 7 (labeled CROP 3 in FIGS. 11 and 12) was also diluted to concentrations of 1.0 wt. % and 0.1 wt. % active ingredient in both deionized water (DI) and CIPAC-D water with a hardness of 342 ppm. Only one sample from Example 7 was used, but the dilutions were performed in duplicate. Photographs of the diluted samples taken immediately after dilution are shown in FIG. 11. Each diluted sample was easy to disperse within 30 inversions of the sample jar. An initial assay indicated that the formulation, prior to dilution, contained 23.3 wt. % of active ingredient.

Figure 12:
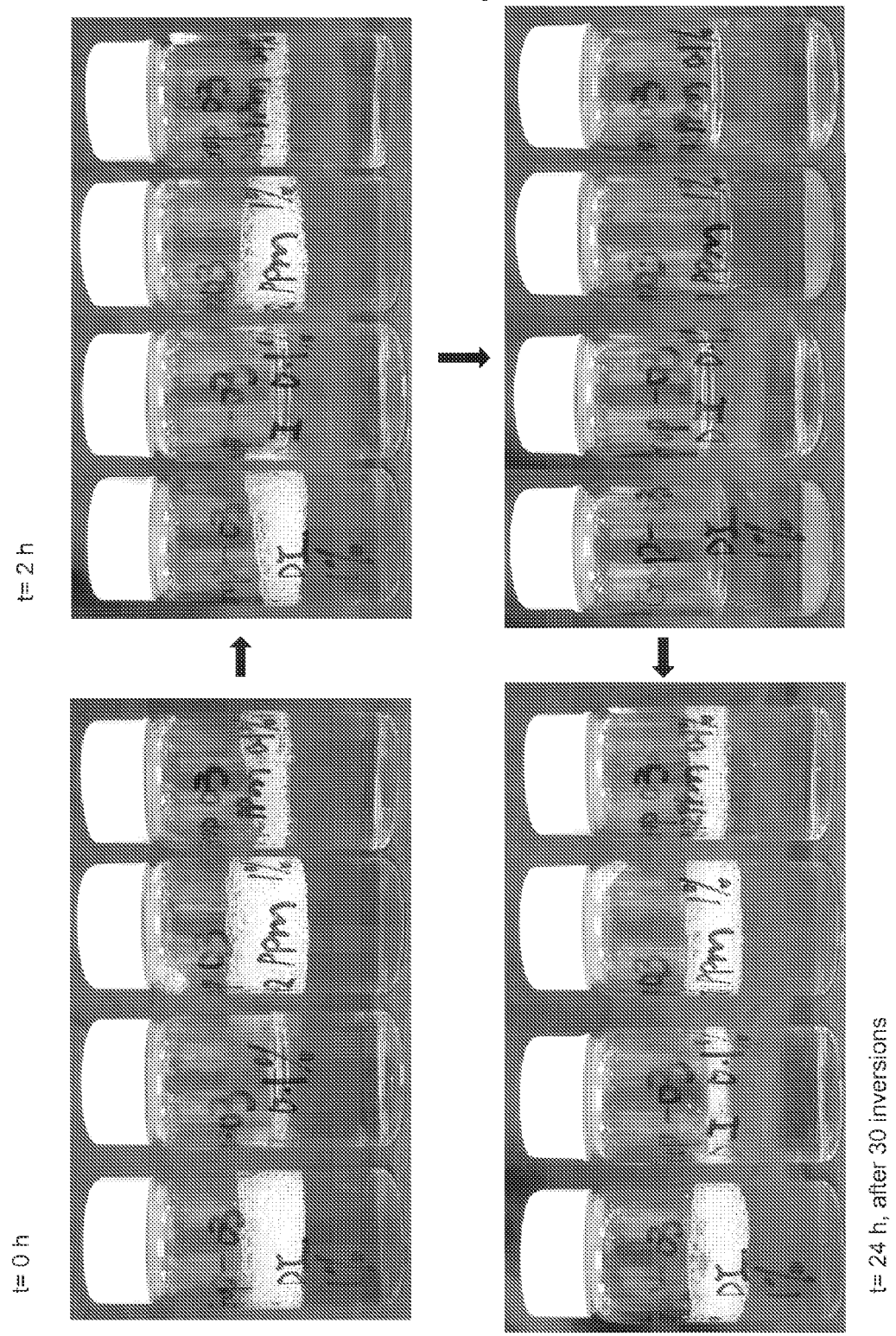
FIG. 12 is a series of photographs showing the stability of the sample of the Example 7 formulation immediately after dilution (upper left), two hours after dilution (upper right), 24 hours after dilution (lower right) and 24 hours after dilution and after 30 inversions of the vial (lower left).

The samples were allowed to stand and photographs of the diluted samples were taken after 2 hours, after 24 hours, and after 30 inversions after standing for 24 hours. The photographs are shown in FIG. 12. Overall, the formulation was easy to disperse and did not produce visible sediment when diluted to 0.1 wt. %.

A further sample of the formulation prepared according to Example 7 was diluted to a concentration of 0.1 g a.i./L in both DI water and CIPAC-D (342 ppm hardness). The particle size for each diluted sample was measured immediately after dilution and again 3 hours after dilution. Particle size results are shown in the tables below. Although the diluted samples contained some micron sized particles, it appears that they dissolved over time, as indicated by the decreasing mass percent values of the largest sized particles in the tables below.

TABLE 14

Particle Size Measurements dilute sample of the formulation of Example 7 in DI water

| Peak | R (nm) | % mass |
| --- | --- | --- |
| Crop 3 - Fresh - DI | | |
| 1 | 7.8 | 0.8 |
| 2 | 109.4 | 0.3 |
| 3 | 814.0 | 0.5 |
| 4 | 7670 | 2.6 |
| 5 | 271268 | 95.9 |
| Crop 3 - 3 hours - DI | | |
| 1 | 10.8 | 0.7 |
| 2 | 127.6 | 0.7 |
| 3 | 2273 | 3.1 |
| 4 | 91283 | 95.6 |

TABLE 15

Particle Size Measurements dilute sample of the formulation of Example 7 in CIPAC-D water

| Peak | R (nm) | % mass |
| --- | --- | --- |
| Crop 3 - Fresh - 342 ppm | | |
| 1 | 6.5 | 10.5 |
| 2 | 181.2 | 1 |
| 3 | 6022 | 11.6 |
| 4 | 150800 | 76.9 |
| Crop 3 - 3 hours - 342 ppm | | |
| 1 | 6.5 | 26 |
| 2 | 97.5 | 1.2 |
| 3 | 366.3 | 1.3 |
| 4 | 4541 | 31.4 |
| 5 | 52881 | 40.2 |

Example 29: Greenhouse Tests of Formulations from Example 6

Figure 13:
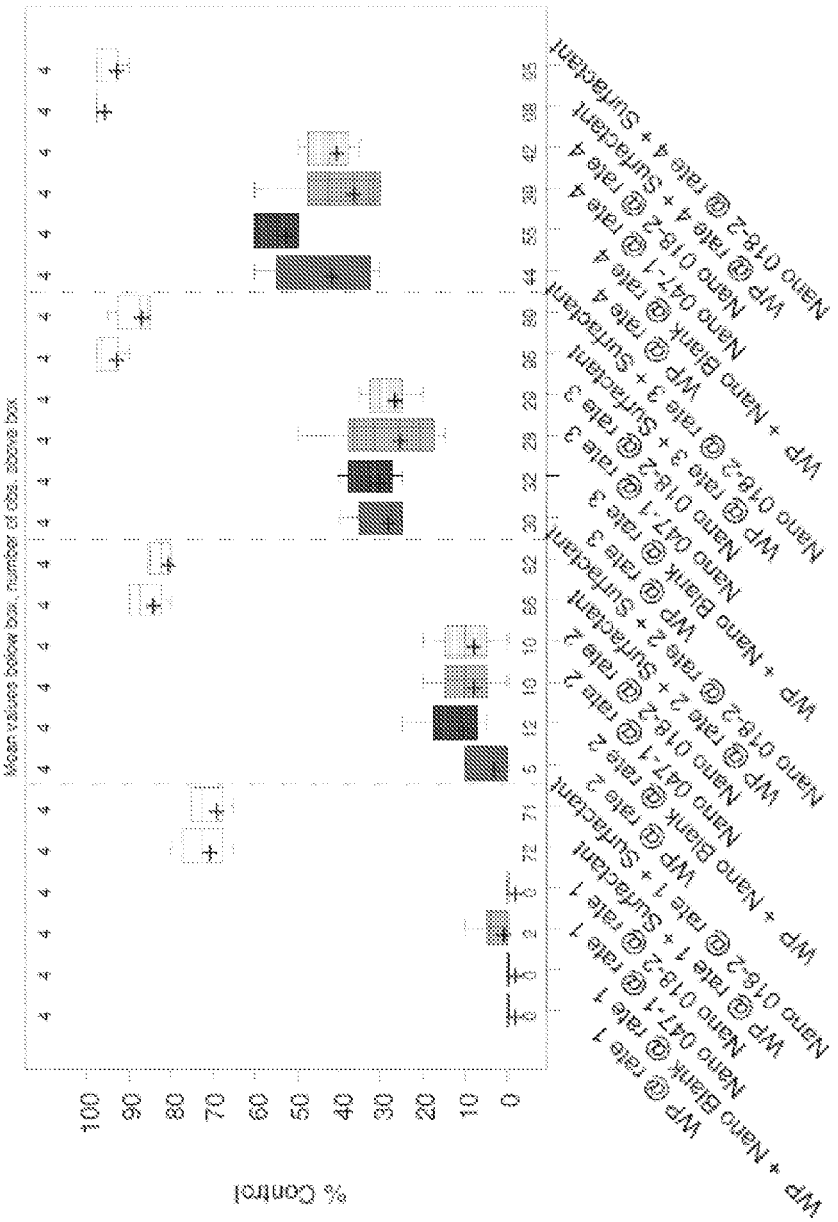
FIG. 13 is a graph comparing rates of control of four different weed species for the formulation of Example 6 at four different rates of application in a green-house trial, described in Example 29. The formulation and control were applied with and without a surfactant. A commercially available herbicide was also used as a comparison. The rates of control are taken 14 days after application.
Figure 14:
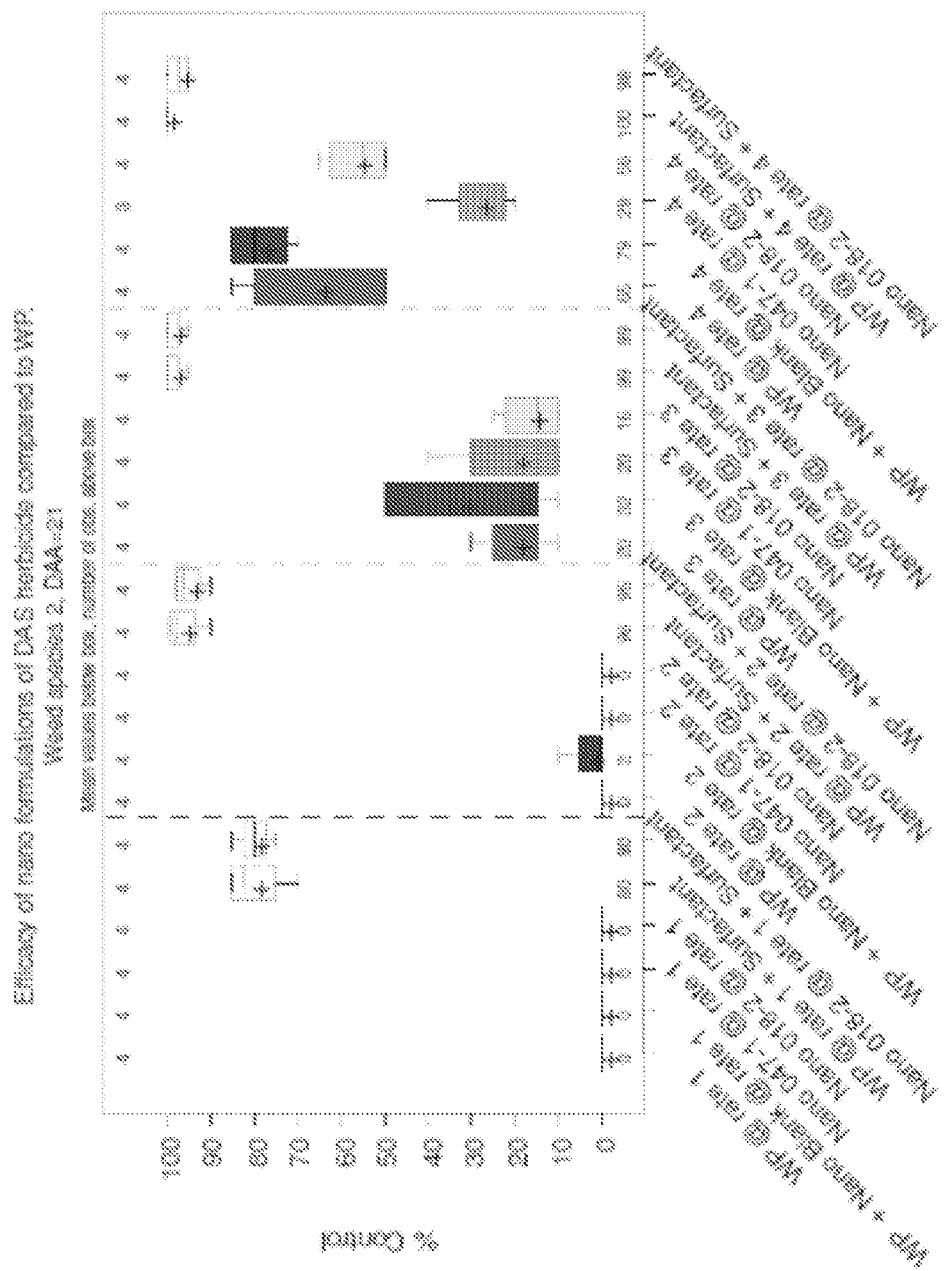
FIG. 14 is a graph comparing rates of control of different weed species as described in Example 29, evaluated 21 days after application.
Figure 15:
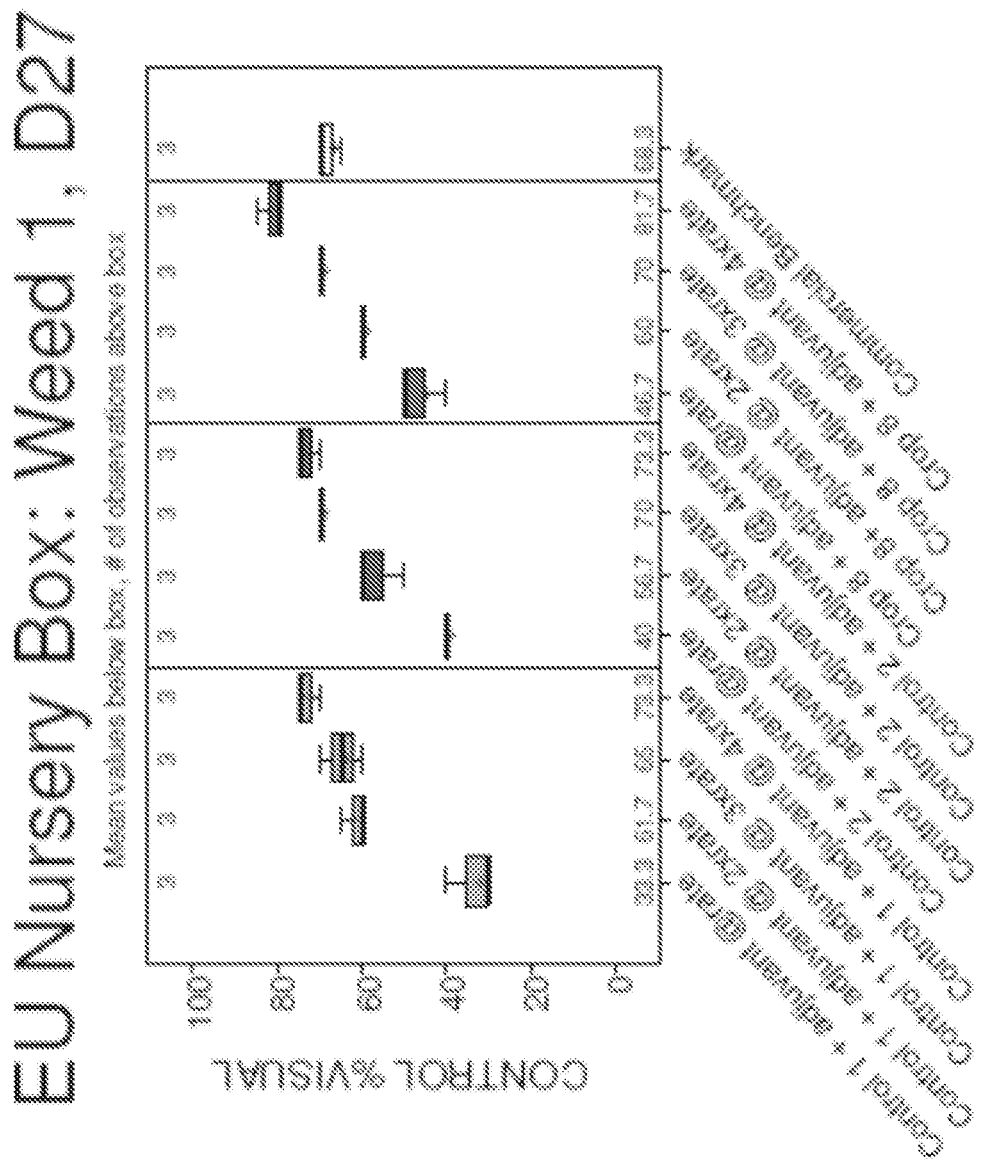
FIGS. 15-24 are graphs comparing the rates of control of different weed species with different herbicide formulations. The formulation of Example 14 was tested against two control herbicides. Four different rates of application were used in testing each formulation against each weed.
Figure 16:
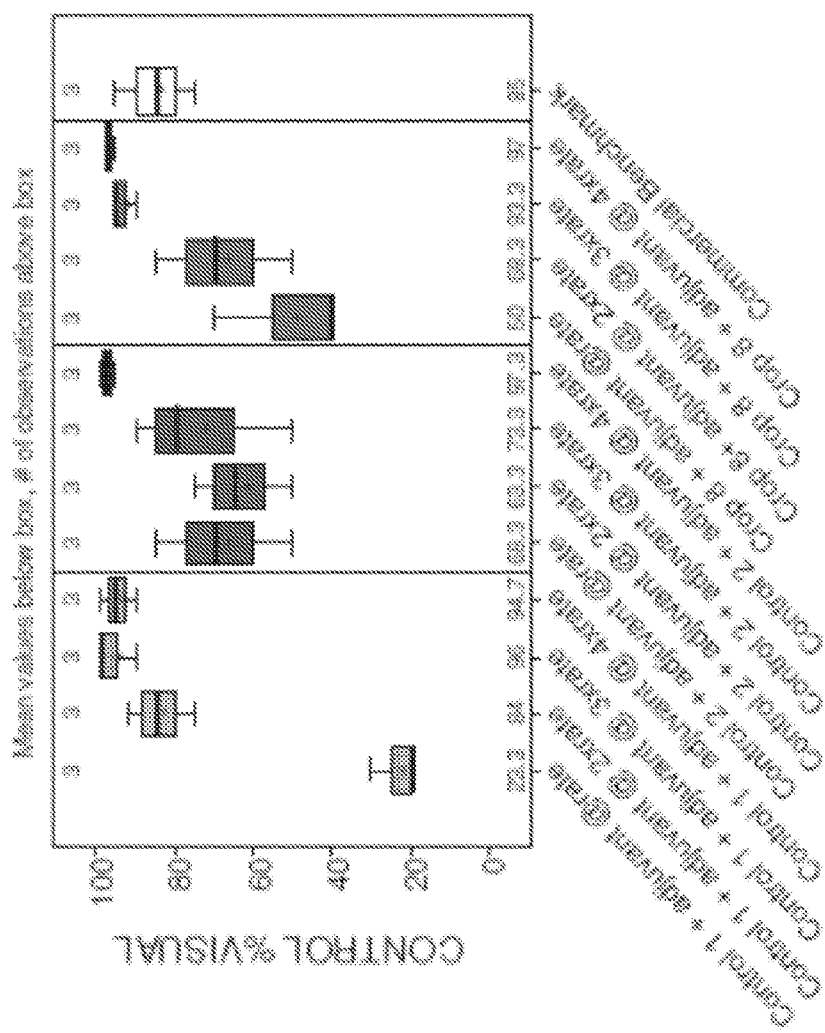
Figure 17:
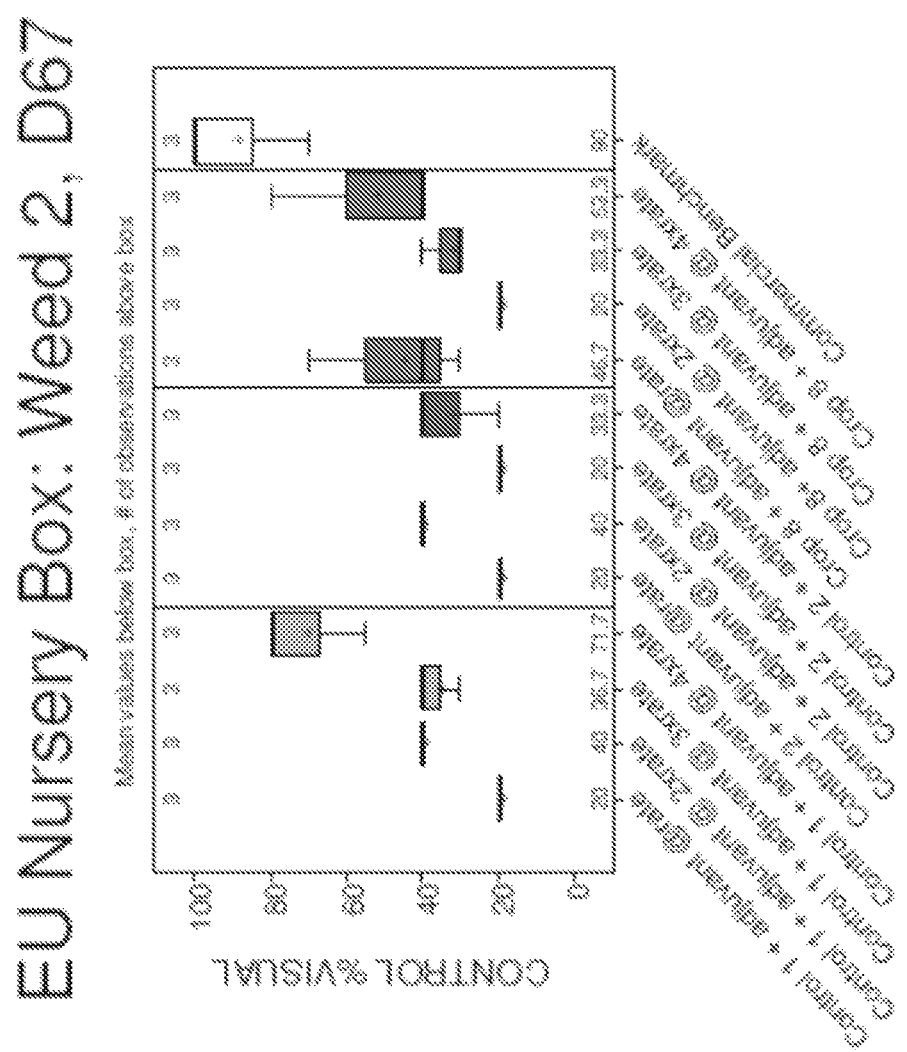
Figure 18:
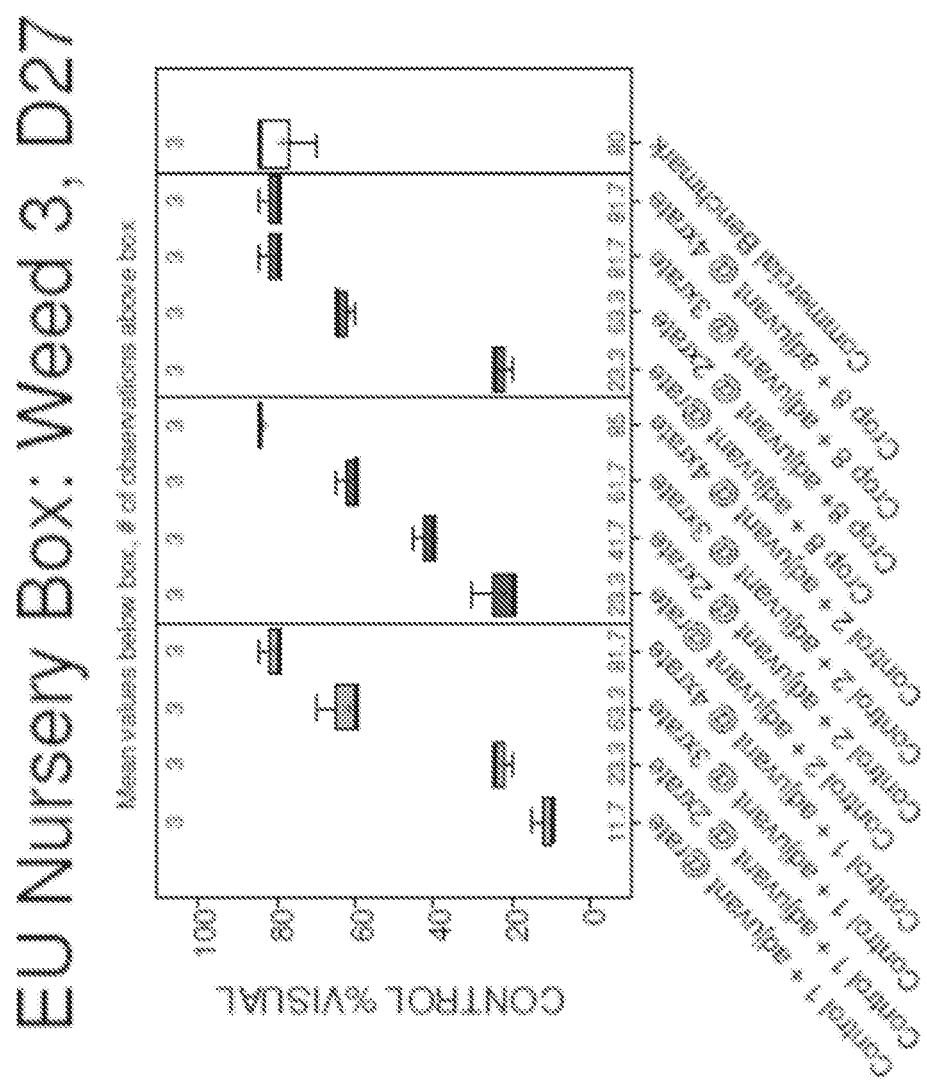
Figure 19:
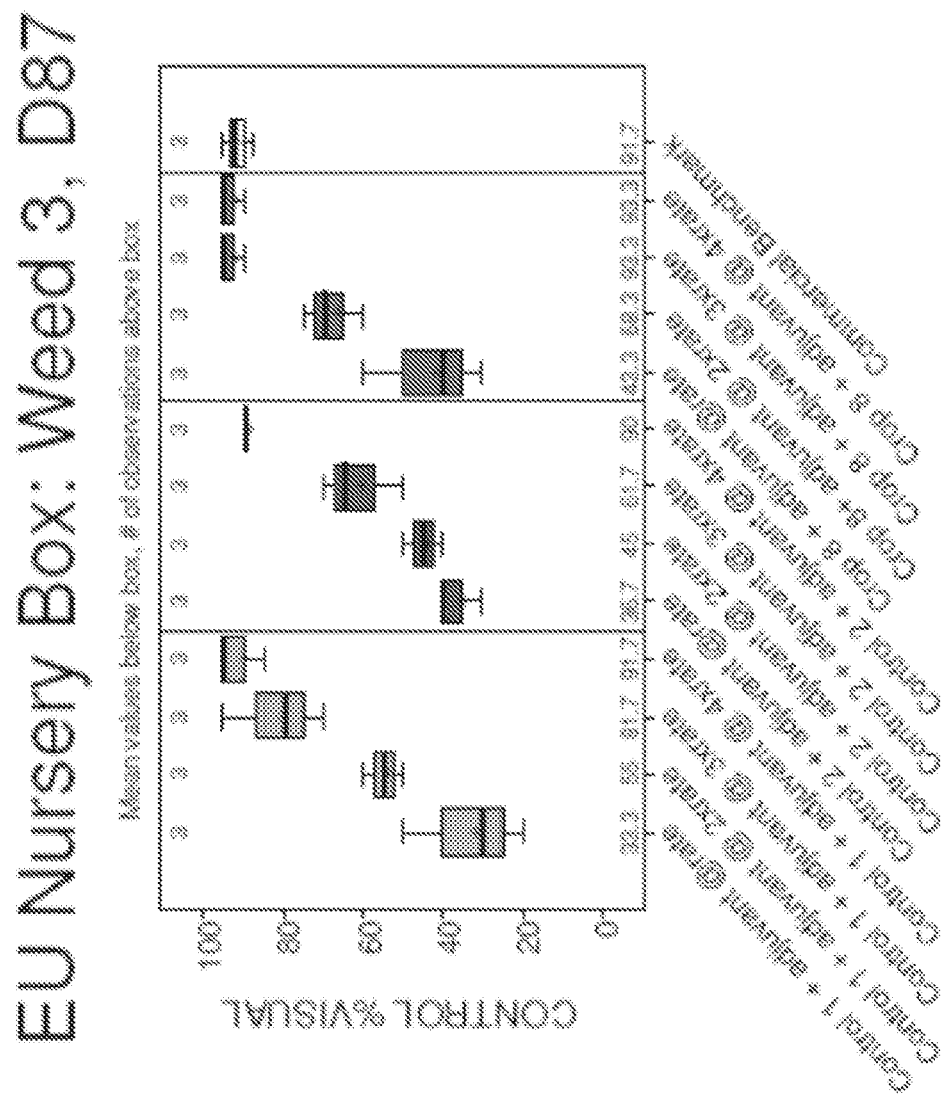
Figure 20:
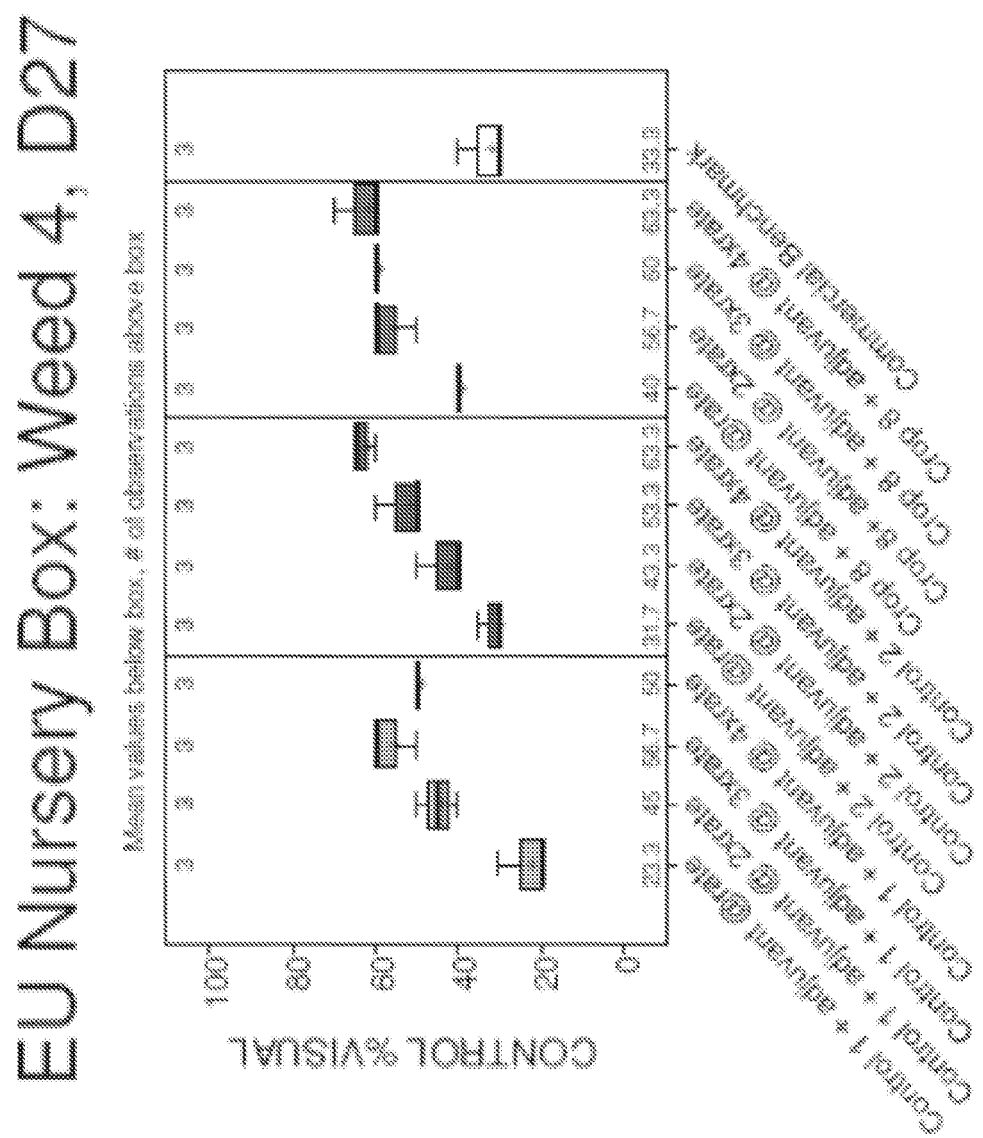
Figure 21:
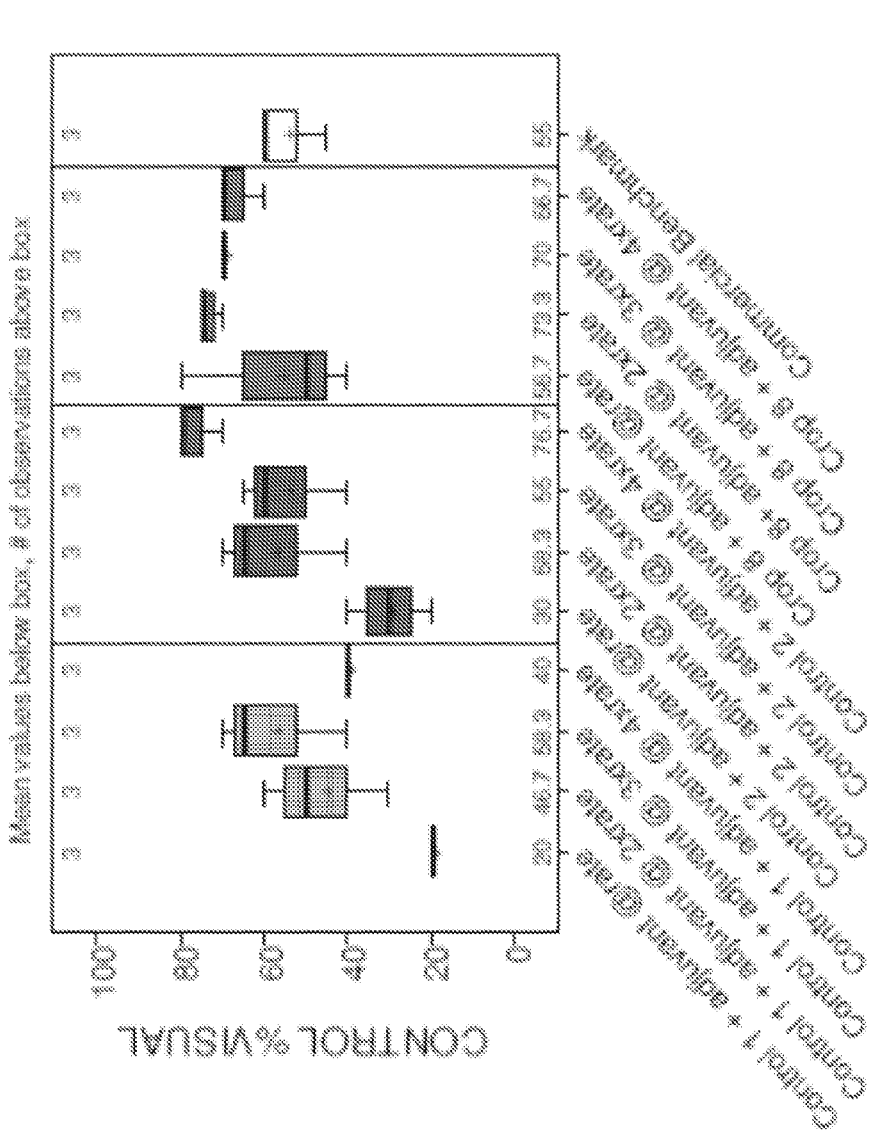
Figure 22:
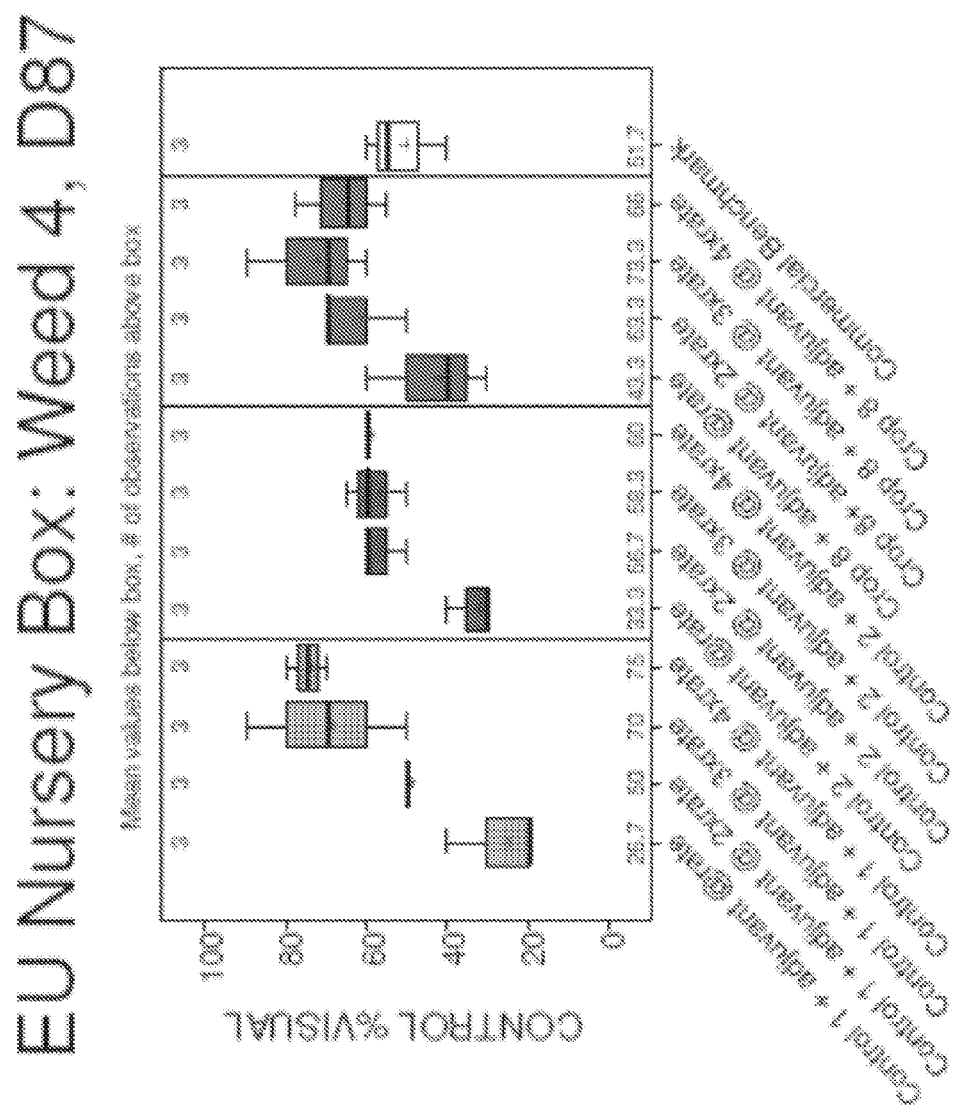
Figure 23:
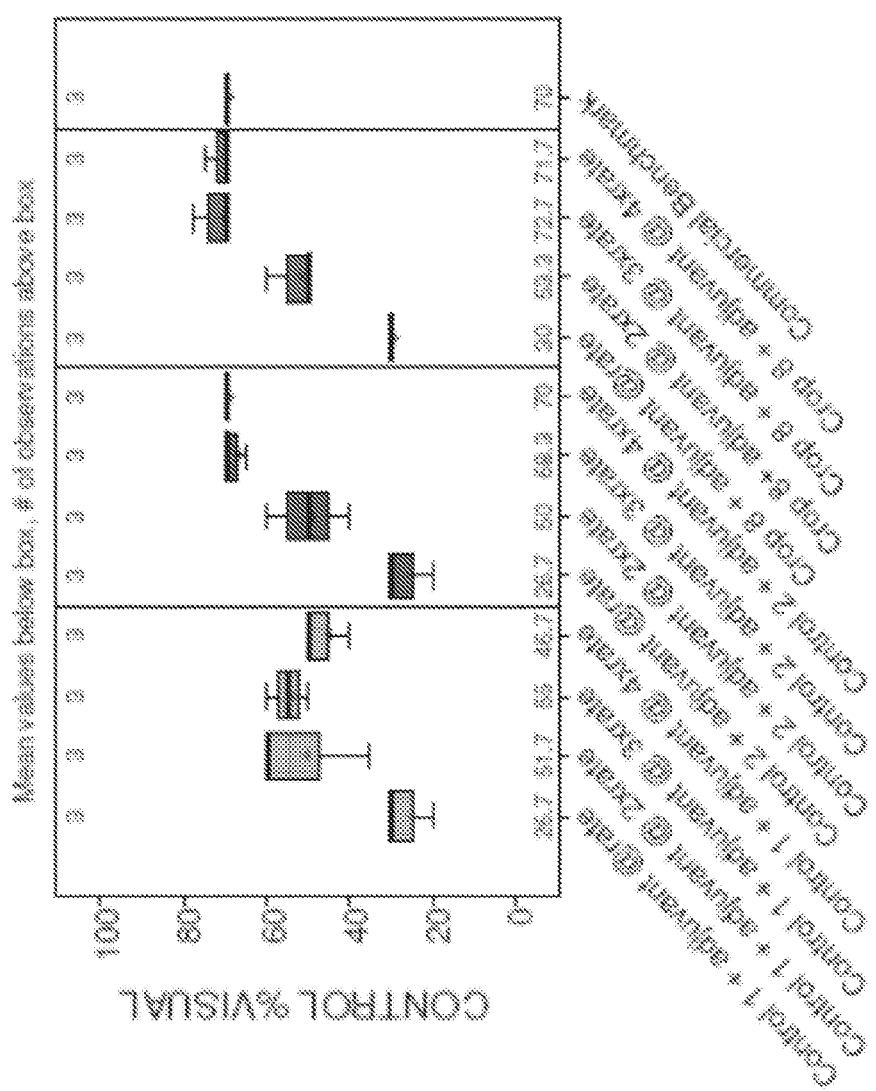
Figure 24:
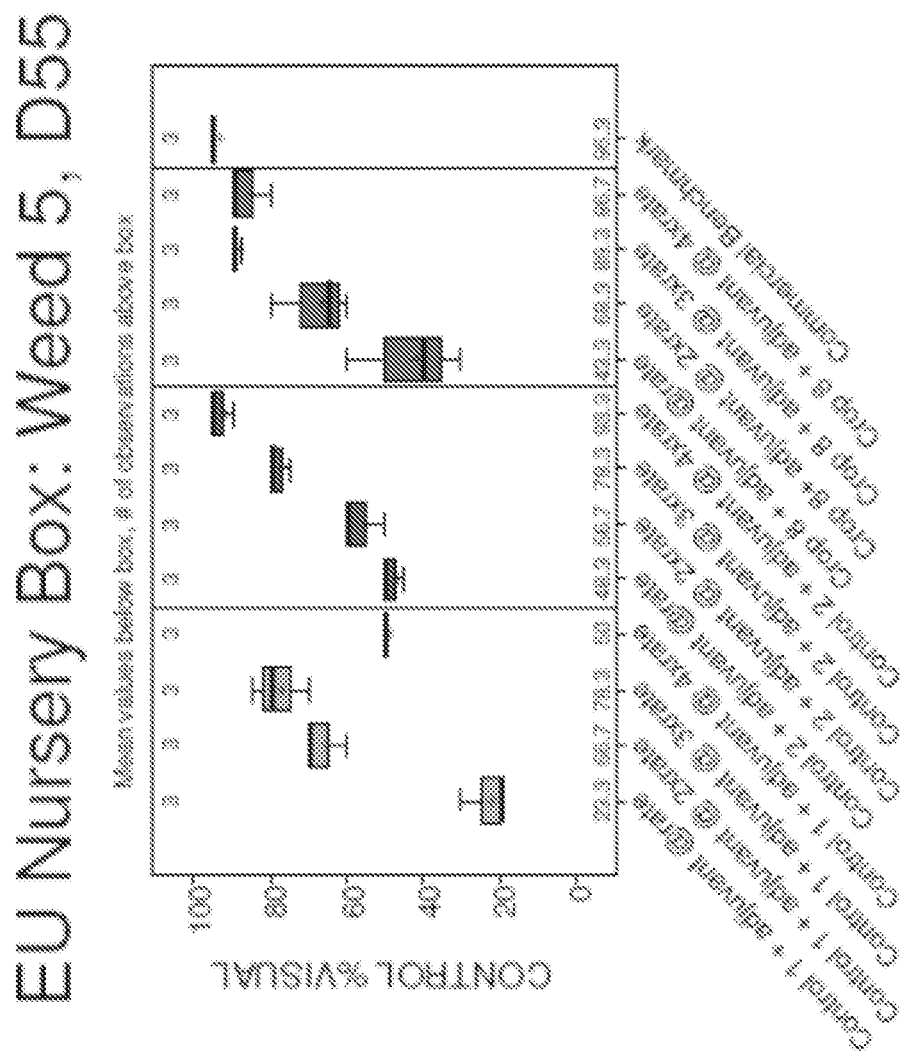

Greenhouse trials for two samples of the formulation from Example 6 were conducted. The formulation samples were applied to at four different application rates (amount of active applied) to four different weed species. The two samples are Crop 2A and Crop 2B from Example 6, which also were labeled Nano-047-1 for 2A and Nano-018-2 in FIGS. 13 & 14. The samples of the formulation were prepared with and without a surfactant. Further, two controls were also prepared and applied. The first control used a wettable powder of a commercially available herbicide. The second control used nanoparticles prepared according to Example 1, without any active ingredient incorporated, but mixed with the commercially available wettable powder herbicide. FIGS. 13 and 14 show percent control of weed species 2, 14 days after application (FIG. 13) and 21 days after application (FIG. 14). Six solutions were applied at four different active ingredient application rates. The six solutions include a wettable powder of a commercially available herbicide, the wettable powder of commercially available herbicide mixed with a solution of nanoparticles prepared according to Example 1, Crop 2A (Nano 047-1) sample prepared according to Example 6, Crop 2B (Nano 18-2) prepared according to Example 6, Crop 2A (Nano 047-1) with an added surfactant, and the commercially available wettable powder with an added surfactant.

The Crop 2A and 2B formulations provided efficacy similar to the commercially available herbicide for all weeds (including weed 2 as shown in FIGS. 13 & 14) though Crop 2B provided improved results when applied at a high rate, with or without added surfactant when applied to weed 4.

Example 30: Greenhouse Tests of Formulations from Example 7-Example 12

Formulations as prepared in Example 7-Example 12 were prepared for greenhouse tests. Each formulation was tested against five weed species (labeled weed 1-weed 5) at four different application rates. The ability of each formulation to control each weed was evaluated 21 days after application. The control was a formulation with pyroxsulam as the active ingredient. All applications were applied by foliar spray.

TABLE 16

Control Rates in Initial Greenhouse Tests for Different Formulations (Weeds 1 & 2)

| | Weed 1 | | | | Weed 2 | | | |
|---|---|---|---|---|---|---|---|---|
| | rate 1 | rate 2 | rate 3 | rate 4 | rate 1 | rate 2 | rate 3 | rate 4 |
| Example 7 | 65% | 73% | 99% | 99% | 23% | 48% | 70% | 94% |
| Example 8 | 38% | 77% | 92% | 99% | 32% | 42% | 83% | 95% |
| Example 9 | 52% | 72% | 98% | 99% | 43% | 50% | 81% | 83% |
| Example 10 | 52% | 63% | 96% | 100% | 32% | 52% | 67% | 94% |
| Example 11 | 70% | 98% | 100% | 100% | 35% | 40% | 67% | 96% |
| Example 12 | 62% | 80% | 94% | 97% | 32% | 38% | 72% | 85% |
| Control | 63% | 93% | 99% | 100% | 47% | 50% | 705 | 94% |

TABLE 17

Control Rates in Initial Greenhouse Tests for Different Formulations (Weeds 3, 4, and 5)

| | Weed 3 | | | | Weed 4 | | | | Weed 5 | | | |
|---|---|---|---|---|---|---|---|---|---|---|---|---|
| | rate 1 | rate 2 | rate 3 | rate 4 | rate 1 | rate 2 | rate 3 | rate 4 | rate 1 | rate 2 | rate 3 | rate 4 |
| Example 7 | 43% | 53% | 93% | 97% | 55% | 62% | 81% | 92% | 12% | 37% | 94% | 96% |
| Example 8 | 30% | 78% | 83% | 97% | 28% | 43% | 58% | 72% | 7% | 67% | 88% | 97% |
| Example 9 | 50% | 72% | 78% | 95% | 35% | 63% | 62% | 73% | 2% | 55% | 95% | 97% |
| Example 10 | 37% | 68% | 73% | 97% | 30% | 43% | 63% | 89% | 7% | 72% | 95% | 97% |
| Example 11 | 47% | 65% | 92% | 94% | 35% | 52% | 62% | 90% | 25% | 53% | 97% | 97% |
| Example 12 | 38% | 58% | 77% | 93% | 58% | 62% | 55% | 88% | 5% | 32% | 93% | 98% |
| Control | 57% | 70% | 74% | 90% | 48% | 55% | 60% | 58% | 3% | 81% | 99% | 98% |

Example 31: Greenhouse Tests of Formulations from Example 7, Example 11, and Example 12

Formulations as prepared in Example 7, Example 11, Example 12 were prepared for further greenhouse tests. Each formulation was tested against five weed species (labeled weed 2-weed 6) at two or five different application rates depending on the weed species. The ability of each formulation to control each weed was evaluated 21 days after application. The control was a formulation with pyroxsulam as the active ingredient. All applications were applied by foliar spray.

TABLE 18

Control Rates in Second Greenhouse Tests for Different Formulations (Weeds 2 & 3)

| | Weed 2 | | | | Weed 3 | | | | |
|---|---|---|---|---|---|---|---|---|---|
| | rate 1 | rate 2 | rate 3 | rate 4 | rate 1 | rate 2 | rate 3 | rate 4 | rate 5 |
| Example 7 | N/A | 73% | 94% | N/A | 18% | 38% | 75% | 92% | 97% |
| Example 11 | N/A | 83% | 83% | N/A | 8% | 40% | 58% | 83% | 96% |
| Example 12 | N/A | 83% | 93% | N/A | 35% | 47% | 75% | 83% | 92% |
| Control | N/A | 89% | 88% | N/A | 32% | 58% | 80% | 90% | 97% |

TABLE 19

Control Rates in Second Greenhouse Tests for Different Formulations
(Weeds 4, 5, and 6)

| | Weed 4 | | | | | Weed 5 | | | | | Weed 6 | | | | |
|---|---|---|---|---|---|---|---|---|---|---|---|---|---|---|---|
| | rate 1 | rate 2 | rate 3 | rate 4 | rate 5 | rate 1 | rate 2 | rate 3 | rate 4 | rate 5 | rate 1 | rate 2 | rate 3 | rate 4 | rate 5 |
| Example 7 | 48% | 67% | 72% | 83% | 82% | 13% | 13% | 47% | 62% | 77% | 73% | 91% | 100% | 100% | 100% |
| Example 11 | 43% | 57% | 72% | 77% | 92% | 15% | 20% | 43% | 67% | 70% | 89% | 99% | 99% | 100% | 100% |
| Example 12 | 53% | 67% | 72% | 77% | 81% | 20% | 40% | 43% | 63% | 72% | 88% | 100% | 100% | 100% | 100% |
| Control | 52% | 65% | 74% | 77% | 83% | 7% | 47% | 57% | 62% | 73% | 83% | 99% | 99% | 100% | 100% |

Example 32: Field Trials of a Formulation According to Example 14

A field trial of the formulation prepared in Example 14 was conducted. The formulation was used to control five different weeds. The formulation was applied at four different rates, a base rate, double the base rate, triple the base rate and four times the base rate. The highest application rate (four times the base rate) was equivalent to the suggested application rate provided on the label of a pyroxsulam herbicide for the particular weed. The base rate is 25% of the commercially labeled application rate. All applications were applied by foliar spray.

The formulations from Example 14 (labeled Crop 8 in the Figures) were compared to a commercial benchmark and two controls. The controls were different formulations both with pyroxsulam as the active ingredient. The commercial benchmark is a based on the label application rate of an herbicide with a different mode of action and from a different chemical class as pyroxsulam.

The invention claimed is:

1. A formulation comprising:
nanoparticles comprising polymer-associated herbicide compound comprising a polymer and a herbicide compound with an average diameter of between about 1 nm and about 500 nm,
wherein the polymer is a polyelectrolyte copolymer comprised of between 50 weight percent and 95 weight percent methacrylic acid monomers and between 50 weight percent and 5 weight percent ethyl acrylate or styrene monomers, and the polymer-associated herbicide compound makes up between about 20 weight percent and about 50 weight percent of the formulation;
between about 0.5 weight percent and about 5 weight percent of a dispersant;
between about 0.5 weight percent and about 5 weight percent of a wetting agent;
between about 0.01 weight percent and about 0.2 weight percent of a preservative;
between about 0.05 weight percent and about 5 weight percent of an anti-foaming agent; and
water.

2. The formulation of claim 1, wherein the herbicide compound is selected from the group consisting of aryloxyphenoxypopionates, cyclohexanediones, triazolinone inhibitors of PPO, and ALS inhibitors.

3. The formulation of claim 1, further comprising a herbicide safener associated with the polymer.

4. The formulation of claim 3, wherein the herbicide safener is selected from the group consisting of mefenpyr-diethyl, isoxadifen-ethyl, cloquintocet-mexyl and combinations thereof.

5. The formulation of claim 4, wherein a ratio of a weight percent of the herbicide safener to a weight percent of the herbicide compound is between about 100:1 and about 1:100.

6. The formulation of claim 3, wherein the herbicide safener is between about 1 weight percent and about 20 weight percent of the formulation.

7. The formulation of claim 1, wherein the nanoparticles have an average diameter of between about 1 nm and about 100 nm.

8. The formulation of claim 1, wherein the nanoparticles have an average diameter of between about 1 nm and about 20 nm.

9. The formulation of claim 1, wherein the nanoparticles are in an aggregate and the aggregate has a diameter of between about 10 nm and about 5000 nm.

10. The formulation of claim 1, wherein a ratio of a weight percent of the herbicide compound to a weight percent of the polymer within the nanoparticles is between about 10:1 and about 1:10.

11. The formulation of claim 1, wherein the herbicide compound is fenoxaprop-P-ethyl or pyroxsulam.

12. The formulation of claim 1, wherein the polymer is a random copolymer.

13. The formulation of claim 1, wherein the dispersant or the wetting agent is selected from the group consisting of lignosulfonates, organosilicones, methylated seed oils, ethoxylates, sulfonates, sulfates and combinations thereof.

14. The formulation of claim 1, further comprising between about 0.05 weight percent and about 5 weight percent of a thickener.

15. The formulation of claim 14, wherein the thickener is selected from the group consisting of guar gum, locust bean gum, xanthan gum, carrageenan, alginates, methyl cellulose, sodium carboxymethyl cellulose, hydroxyethyl cellulose, modified starches, polysaccharides, other modified polysaccharides, polyvinyl alcohol, glycerol alkyd and combinations thereof.

16. The formulation of claim 1, wherein the preservative is selected from the group consisting of tocopherol, ascorbyl palmitate, propyl gallate, butylated hydroxyanisole (BHA), butylated hydroxytoluene (BHT), propionic acid and its sodium salt; sorbic acid and its sodium or potassium salts; benzoic acid and its sodium salt; p-hydroxy benzoic acid sodium salt; methyl p-hydroxy benzoate; 1,2-benzisothiazalin-3-one, and combinations thereof.

17. The formulation of claim 1, further comprising between about 0.05 weight percent and about 10 weight percent of an anti-freezing agent.

18. The formulation of claim 17, wherein the anti-freezing agent is selected from the group consisting of ethylene glycol, propylene glycol, urea and combinations thereof.

19. The formulation of claim 1, further comprising between about 1 weight percent and about 20 weight percent of a non-ionic surfactant.

* * * * *

UNITED STATES PATENT AND TRADEMARK OFFICE
CERTIFICATE OF CORRECTION

PATENT NO.         : 9,961,900 B2
APPLICATION NO.    : 14/406855
DATED              : May 8, 2018
INVENTOR(S)        : Darren J. Anderson et al.

It is certified that error appears in the above-identified patent and that said Letters Patent is hereby corrected as shown below:

In the Claims

• Column 67, Line 38 Claim 1, insert --a-- after "nanoparticles comprising".

Signed and Sealed this
Tenth Day of July, 2018

Andrei Iancu
*Director of the United States Patent and Trademark Office*